US011077185B2

(12) United States Patent
Zagury

(10) Patent No.: US 11,077,185 B2
(45) Date of Patent: *Aug. 3, 2021

(54) VACCINE TO PATHOGENIC IMMUNE ACTIVATION CELLS DURING INFECTIONS

(71) Applicant: 21C Bio, Paris (FR)

(72) Inventor: Daniel Zagury, Paris (FR)

(73) Assignee: 21C Bio, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/825,727

(22) Filed: Mar. 20, 2020

(65) Prior Publication Data

US 2020/0297837 A1 Sep. 24, 2020

Related U.S. Application Data

(63) Continuation-in-part of application No. 16/360,876, filed on Mar. 21, 2019, now Pat. No. 10,632,186.

(60) Provisional application No. 62/821,774, filed on Mar. 21, 2019.

(30) Foreign Application Priority Data

Jul. 31, 2019 (EP) .................................... 19189405

(51) Int. Cl.
| | |
|---|---|
| *A61K 39/395* | (2006.01) |
| *A61K 38/00* | (2006.01) |
| *A61K 39/00* | (2006.01) |
| *C07K 16/00* | (2006.01) |
| *C07K 16/42* | (2006.01) |
| *A61K 39/21* | (2006.01) |
| *A61K 38/21* | (2006.01) |
| *C12N 7/00* | (2006.01) |
| *A61K 39/09* | (2006.01) |
| *A61P 31/18* | (2006.01) |
| *A61K 45/06* | (2006.01) |

(52) U.S. Cl.
CPC ............ *A61K 39/21* (2013.01); *A61K 38/212* (2013.01); *A61K 38/217* (2013.01); *A61K 39/092* (2013.01); *A61P 31/18* (2018.01); *C12N 7/00* (2013.01); *A61K 45/06* (2013.01); *A61K 2039/5254* (2013.01)

(58) Field of Classification Search
CPC ............... A61K 2300/00; A61K 38/00; A61K 2039/505; A61P 35/00; A61P 43/00
See application file for complete search history.

(56) References Cited

U.S. PATENT DOCUMENTS

| | | |
|---|---|---|
| 5,168,062 A | 12/1992 | Stinski |
| 5,385,839 A | 1/1995 | Stinski |
| 2003/0138404 A1 | 7/2003 | Maroun |
| 2010/0142823 A1 | 6/2010 | Wang et al. |
| 2013/0136768 A1 | 5/2013 | Picker et al. |
| 2014/0141038 A1 | 5/2014 | Picker et al. |

FOREIGN PATENT DOCUMENTS

| | | |
|---|---|---|
| WO | 2011/028257 A1 | 3/2011 |
| WO | 2012/137071 A2 | 10/2012 |
| WO | 2014/052545 A2 | 4/2014 |
| WO | 2014/138209 A1 | 9/2014 |
| WO | 2016/130693 A1 | 8/2016 |
| WO | 2018/006067 A1 | 1/2018 |
| WO | 2018/075591 A1 | 4/2018 |

OTHER PUBLICATIONS

Jiang et al., "HIV-1 DNA vaccine efficacy is enhanced by coadminsitration with plasmid encoding IFN-alpha", Journal of Virological Methods, 2007, 146:266-273.*
Wei Lu, et al., "Suppression of HIV Replication by CD8+ Regulatory T-Cells in Elite Controllers", Frontiers in Immunology, vol. 7, Article 134, Apr. 2016, pp. 1-10 (10 pp.).
Scott G. Hansen, et al., "Cytomegalovirus Vectors Violate CD8+ T Cell Epitope Recognition Paradigms", NIH Public Access Author Manuscript, Science, May 24, 2013, vol. 340(6135), pp. 1-34 (34 pp.), doi:10.1126/science.1237874.
Scott G. Hansen, et al., "Broadly targeted CD8+ T cell responses restricted by major histocompatibility complex-E", HHS Public Access Author manuscript, Science, Feb. 12, 2016, vol. 351(6274), pp. 714-720 (16 pp.), doi:10.1126/science.aac9475.
Wei Lu, et al., "Induction of CD8+ Regulatory T Cells Protects Macaques against SIV Challenge", Cell Reports 2, Dec. 27, 2012, pp. 1736-1746 (11 pp.), http://dx.doi.org/10.1016/j.celrep.2012.11.016.
Jean-Marie Andrieu, et al., "Mucosal SIV vaccines comprising inactivated virus particles and bacterial adjuvants induce CD8+ T-regulatory cells that suppress SIV-positive CD4+ T-Cell activation and prevent SIV infection in the macaque model", Frontiers in Immunology, vol. 5, Article 297, Jun. 30, 2014, pp. 1-11 (11 pp.), doi: 10.3389/fimmu.2014.00297.
Jin H. Felgner, et al., "Enhanced Gene Delivery and Mechanism Studies with a Novel Series of Cationic Lipid Formulations*", The Journal of Biological Chemistry, vol. 269, No. 4, Jan. 28, 1994, pp. 2550-2561 (12 pp).
Jeffrey B. Ulmer, et al., "Heterologous Protection Against Influenza by Injection of DNA Encoding a Viral Protein", Science, vol. 259, Mar. 19, 1993, pp. 1745-1749 (5 pp.).
Allan J. Masterson, et al., "MUTZ-3, a human cell line model for the cytokine-induced differentiation of dendritic cells from CD34+ precursors", Blood, vol. 100, No. 2, Jul. 15, 2002, pp. 701-703 (3 pp.).

(Continued)

*Primary Examiner* — Barry A Chestnut
(74) *Attorney, Agent, or Firm* — Maier & Maier, PLLC

(57) ABSTRACT

In the present invention, the Applicant provides a novel method for preventing or treating an infectious disease in a subject in need thereof. In particular said method comprise the administration of a combination, pharmaceutical combination, medicament or kit-of-parts comprising a first part comprising a CD8 vaccine specific for at least one infectious disease-related antigen, optionally a second part comprising an interferon alpha blocking agent, and a third part comprising a type III interferon and/or an agent stimulating the production of type III interferon.

18 Claims, 11 Drawing Sheets

Specification includes a Sequence Listing.

(56) References Cited

OTHER PUBLICATIONS

Cathy Steel, et al., "Helminth Antigens Selectively Differentiate Unsensitized CD45RA +CD4+ Human T cells in Vitro", The Journal of Immunology, 1998, vol. 160, pp. 351-360 (11 pp.), http://www.jimmunol.org/content/160/1/351.

X Tao, et al., "Induction of IL-4-producing CD4+ T cells by antigenic peptides altered for TCR binding", The Journal of Immunology, 1997, vol. 158, pp. 4237-4244 (9 pp.), http://www.jimmunol.org/content/158/9/4237.

Igor Dozmorov, et al., "In Vitro Production of Antigen-Specific T Cells from Unprimed Mice: Role of Dexamethasone and Anti-IL-10 Antibodies", Cellular Immunology, vol. 178, Article No. CI971134, 1997, pp. 187-196 (10 pp.).

Kayo Inaba, et al., "Direct Activation of CD8+ Cytotoxic T Lymphocytes by Dendritic Cells", J. Exp. Med., vol. 166, Jul. 1987, pp. 182-194 (13 pp.).

Steven E. Macatonia, et al., "Primary Stimulation by Dendritic Cells Induces Antiviral Proliferative and Cytotoxic T Cell Responses in Vitro", J. Exp. Med., vol. 169, Apr. 1989, pp. 1255-1264 (10 pp.).

Marloes L. H. De Bruijn, et al., "Mechanisms of induction of primary virus-specific cytotoxic T lymphocyte responses*'", Eur. J. Immunol., 1992, vol. 22, pp. 3013-3020 (8 pp.).

Stefanie André, et al., "Increased Immune Response Elicited by DNA Vaccination with a Synthetic gp120 Sequence with Optimized Codon Usage", Journal of Virology, vol. 72, No. 2, Feb. 1998, pp. 1497-1503 (7 pp.).

Nicolas Noel, et al., "Interferon-associated therapies toward HIV control: The back and forth", Cytokine and Growth Factor Reviews, Elsevier, 2018, vol. 40, pp. 99-112 (47 pp.), 10.1016/j.cytogfr.2018.03.004, pasteur-01969821.

Krystelle Nganou-Makamdop, et al., "Type I IFN signaling blockade by a PASylated antagonist during chronic SIV infection suppresses specific inflammatory pathways but does not alter T cell activation or virus replication", PLoS Pathogens, Aug. 24, 2018, vol. 14, No. 8, e1007246, pp. 1-20 (20 pp.); https://doi.org/10.1371/journal.ppat.1007246.

Simon J. Waddell, et al., "Dissecting Interferon-Induced Transcriptional Programs in Human Peripheral Blood Cells", PLoS One, www.plosone.org, Mar. 2010, vol. 5, Issue 3, e9753, pp. 1-12 (13 pp.).

M. H. Lampen, et al., "CD8+ T Cell Responses against TAP-Inhibited Cells Are Readily Detected in the Human Population", The Journal of Immunology, Oct. 27, 2010, vol. 185, No. 11, pp. 6508-6517 (11 pp.), doi: 10.4049/immunol.1001774, http://www.jimmunol.org/content/185/11/6508.

Klaus Früh, et al., "CD8+ T cell programming by cytomegalovirus vectors: applications in prophylactic and therapeutic vaccination", HHS Public Acces Author manuscript, Curr Opin Immunol., available in PMC Aug. 1, 2018, Curr Opin Immunol, 2017, Aug. 2017, vol. 47, pp. 52-56 (10 pp.), doi:10.1016/j.coi.2017.06.010.

Zara Hannoun, et al., "Identification of novel HIV-1-derived HLA-E-binding peptides", Immunology Letters, vol. 202, 2018, pp. 65-72 (8 pp.).

J.P. Coulaud, et al., "A placebo controlled clinical phase I trial with combined anti-HIV-1 and anti-interferon-alpha immunization", AIDS, 1997, vol. 11, No. 7, pp. 937-938 (3 pp.).

R. C. Gallo, et al., "Targeting Tat and IFNα as a Therapeutic AIDS Vaccine", DNA and Cell Biology, vol. 21, No. 9, 2002, pp. 611-618 (8 pp.).

Diane Carnathan, et al., "Reduced Chronic Lymphocyte Activation following Interferon Alpha Blockade during the Acute Phase of Simian Immunodeficiency Virus Infection in Rhesus Macaques", Journal of Virology, vol. 92, Issue 9, May 2018, pp. 1-14 (14 pp.)., e01760-17.

Anjie Zhen, et al., "Targeting type I interferon-mediated activation restores immune function in chronic HIV infection", The Journal of Clinical Investigation, 2017, vol. 127, No. 1, pp. 260-268 (10 pp.), https://doi.org/10.1172/JCI89488.

Qi-Jian Su, et al., "IFN-λ4 inhibits HIV infection of macrophages through signalling of IFN-λR1/IL-10R2 receptor complex", Scandinavian Journal of Immunology, Experimental Immunology, 2018, vol. 88, No. 5, pp. 1-5 (6 pp.), e12717.

N. Ank, et al., "Lambda Interferon (IFN-λ), a Type III IFN, Is Induced by Viruses and IFNs and Displays Potent Antiviral Activity against Select Virus Infections in Vivo", Journal of Virology, vol. 80, No. 9, May 2006, pp. 4501-4509 (9 pp.).

Wenzheng Jiang, et al., "HIV-1 DNA vaccine efficacy is enhanced by coadministration with plasmid encoding IFN-α", Journal of Virological Methods, vol. 146, 2007, pp. 266-273 (8 pp.), available online at www.sciencedirect.com.

* cited by examiner

SEQUENCE LISTING

```
<160> NUMBER OF SEQ ID NOS: 17

<210> SEQ ID NO 1
<211> LENGTH: 9
<212> TYPE: PRT
<213> ORGANISM: Artificial Sequence
<220> FEATURE:
<223> OTHER INFORMATION: MHCIb/E-binding antigen

<400> SEQUENCE: 1

Arg Met Tyr Ser Pro Val Ser Ile Leu
1               5

<210> SEQ ID NO 2
<211> LENGTH: 9
<212> TYPE: PRT
<213> ORGANISM: Artificial Sequence
<220> FEATURE:
<223> OTHER INFORMATION: MHCIb/E-binding antigen

<400> SEQUENCE: 2

Pro Glu Ile Val Ile Tyr Asp Tyr Met
1               5

<210> SEQ ID NO 3
<211> LENGTH: 9
<212> TYPE: PRT
<213> ORGANISM: Artificial Sequence
<220> FEATURE:
<223> OTHER INFORMATION: MHCIb/E-binding antigen

<400> SEQUENCE: 3

Thr Ala Leu Ser Glu Gly Ala Thr Pro
1               5

<210> SEQ ID NO 4
<211> LENGTH: 9
<212> TYPE: PRT
<213> ORGANISM: Artificial Sequence
<220> FEATURE:
<223> OTHER INFORMATION: MHCIb/E-binding antigen

<400> SEQUENCE: 4

Arg Ile Arg Thr Trp Lys Ser Leu Val
1               5
```

```
<210> SEQ ID NO 5
<211> LENGTH: 9
<212> TYPE: PRT
<213> ORGANISM: Artificial Sequence
<220> FEATURE:
<223> OTHER INFORMATION: CMV-derived peptide

<400> SEQUENCE: 5

Val Met Ala Pro Arg Thr Leu Ile Leu
1               5

<210> SEQ ID NO 6
<211> LENGTH: 9
<212> TYPE: PRT
<213> ORGANISM: Artificial Sequence
<220> FEATURE:
<223> OTHER INFORMATION: CMV-derived peptide

<400> SEQUENCE: 6

Val Met Ala Pro Arg Thr Leu Val Leu
1               5

<210> SEQ ID NO 7
<211> LENGTH: 15
<212> TYPE: PRT
<213> ORGANISM: Artificial Sequence
<220> FEATURE:
<223> OTHER INFORMATION: HLA-DR-restricted p24 antigen

<400> SEQUENCE: 7

Gln Gly Gln Met Val His Gln Ala Ile Ser Pro Arg Thr Leu Asn
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: HLA-DR-restricted p24 antigen

<400> SEQUENCE: 8

Gly Glu Ile Tyr Lys Arg Trp Ile Ile Leu Gly Leu Asn Lys Ile
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: HLA-DR-restricted p24 antigen

<400> SEQUENCE: 9

Lys Arg Trp Ile Ile Leu Gly Leu Asn Lys Ile Val Arg Met Tyr
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: HLA-DR-restricted RT antigen

<400> SEQUENCE: 10

Phe Arg Lys Tyr Thr Ala Phe Thr Ile Pro Ser Ile Asn Asn Glu
1               5                   10                  15

<210> SEQ ID NO 11
```

```
<211> LENGTH: 6
<212> TYPE: PRT
<213> ORGANISM: Artificial Sequence
<220> FEATURE:
<223> OTHER INFORMATION: Claudin 4-binding peptide

<400> SEQUENCE: 11

Cys Thr Gly Lys Ser Cys
1               5

<210> SEQ ID NO 12
<211> LENGTH: 4
<212> TYPE: PRT
<213> ORGANISM: Artificial Sequence
<220> FEATURE:
<223> OTHER INFORMATION: Claudin 4-binding peptide

<400> SEQUENCE: 12

Leu Arg Val Gly
1

<210> SEQ ID NO 13
<211> LENGTH: 9
<212> TYPE: PRT
<213> ORGANISM: Artificial Sequence
<220> FEATURE:
<223> OTHER INFORMATION: Claudin 4-binding peptide

<400> SEQUENCE: 13

Cys Lys Ser Thr His Pro Leu Ser Cys
1               5

<210> SEQ ID NO 14
<211> LENGTH: 9
<212> TYPE: PRT
<213> ORGANISM: Artificial Sequence
<220> FEATURE:
<223> OTHER INFORMATION: EBV derived peptide

<400> SEQUENCE: 14

Ser Gln Ala Pro Leu Pro Cys Val Leu
1               5

<210> SEQ ID NO 15
<211> LENGTH: 9
<212> TYPE: PRT
<213> ORGANISM: Artificial Sequence
<220> FEATURE:
<223> OTHER INFORMATION: MBt derived peptide

<400> SEQUENCE: 15

Val Met Ala Thr Arg Arg Asn Val Leu
1               5

<210> SEQ ID NO 16
<211> LENGTH: 9
<212> TYPE: PRT
<213> ORGANISM: Artificial Sequence
<220> FEATURE:
<223> OTHER INFORMATION: HIV-1 Pol derived peptide

<400> SEQUENCE: 16

Pro Glu Ile Val Ile Tyr Asp Tyr Met
1               5

<210> SEQ ID NO 17
<211> LENGTH: 9
```

```
<212> TYPE: PRT
<213> ORGANISM: Artificial Sequence
<220> FEATURE:
<223> OTHER INFORMATION: HIV-1 Pol derived peptide

<400> SEQUENCE: 17

Arg Ile Arg Thr Trp Lys Ser Leu Val
1               5
```

VACCINE TO PATHOGENIC IMMUNE ACTIVATION CELLS DURING INFECTIONS

FIELD OF INVENTION

In the present invention, the Applicant provides a novel method for preventing or treating an infectious disease in a subject in need thereof. In particular said method comprise the administration of a combination, pharmaceutical combination, medicament or kit-of-parts comprising a first part comprising a CD8 vaccine specific for at least one infectious disease-related antigen, optionally a second part comprising an interferon alpha blocking agent, and a third part comprising a type III interferon and/or an agent stimulating the production of type III interferon.

BACKGROUND OF INVENTION

Soon after the initial discovery of human immunodeficiency virus (HIV) as the cause of acquired immune deficiency syndrome (AIDS), a very small group of HIV-infected patients has been identified to remain AIDS-free for several decades. These so-called HIV elite controllers (EC) usually have relatively high $CD4^+$ T cell counts and are able to maintain clinically undetectable plasma HIV-1 RNA level (HIV RNA<50 copies/mL) during a prolonged period of time in the absence of any antiretroviral treatment (ART). During recent years, extensive research has been made to define mechanisms by which these rare individuals control HIV.

Interestingly, the EC status suggests a low activation profile of T cells and the existence of a unique MHC-1b/E-restricted $CD8^+$ T cell population able to suppress the early activation of pathogenic HIV antigen-presenting CD4+ T cells (Lu et al. (2016) Front. Immunol. 7:134). Furthermore, recent advances in the field of SIV vaccinology also have highlighted the role of MHC-1b/E-restricted $CD8^+$ T cell responses in controlling SIV infection in rhesus macaques (Hansen et al. (2013) Science 24; 340(6135):1237874; Hansen et al. (2016) Science; 351(6274), 714-20; Lu et al. (2012) Cell Rep. 2(6), 1736-46; Andrieu et al. (2014) Front Immunol. 5:297). These observations have suggested alternative strategies for developing an HIV vaccine.

Indeed, since an activated state of the $CD4^+$ T cell is a prerequisite for productive HIV infection also in vivo, and thus replication in quiescent $CD4^+$ T cells is essentially nonproductive and generally abortive, it has been hypothesized that it might be possible to suppress viral replication by interfering with the $CD4^+$ T cell activation. Therefore, several groups have tempted to suppress virus-specific $CD4^+$T cell activation with vaccines that induce MHC-1b/E-restricted $CD8^+$ cells.

For example, Andrieu et al. have developed a vaccine able to induce MHC-1b/E-restricted $CD8^+$ T cells in macaques. This vaccine consisted of inactivated simian immunodeficiency virus (SIV) particles associated with a tolerogenic adjuvant, such as, for example, *Lactobacillus plantarum*. Although this vaccine strategy effectively immunized and induced suppressive MHC-1b/E-restricted $CD8^+$ T cells in Chinese macaques, macaques of Indian origin that were immunized with the same adjuvanted vaccine were not protected.

Hansen et al., by modifying cytomegalovirus (CMV) vectors determinants that control unconventional T cell priming, have shown that it was possible to uniquely tailor the $CD8^+$ T cell response in order to maximize prophylactic or therapeutic protection. Specifically, it was found that the use of such rhesus cytomegalovirus vectors expressing SIV protein in rhesus macaques (RMs) induces post-challenge sterile protection against SIV. However, this protection was effective in only 50% of vaccinated RMs.

Globally, these results have expanded the current paradigm from one focused on a preventive HIV vaccine to one in which an immunotherapy for HIV/AIDS can be an essential part of the fight against this pandemic. Thus, in addition to a preventive vaccine, there remains a need for an effective therapy to treat individuals living with HIV-1.

Based on the discovery of new biological properties of type III interferon (IFN-III), the inventors propose to improve existing vaccine (i.e., induction of a suppressive MHC-1b/E-restricted $CD8^+$ T cell population) strategies for preventing or treating HIV and others infectious diseases.

In particular, the Applicant demonstrates that type III interferon may greatly potentiate existing CD8 suppressive vaccines. Indeed, on the contrary of type I interferons, type III interferons appear to have a more specialized role in innate antiviral defense and do not inhibit the initiation of the adaptive immune reaction after HIV infection. In particular, IFN-III can prevent or limit virus replication without inhibiting the proliferation of $CD4^+$ T cells that respond to HIV infection.

The Applicant further demonstrates that the blockade of interferon alpha (IFN-α) as a supplement to a CD8 suppressive vaccine might potentiate type III interferon and thus greatly improve the vaccine efficacy. Indeed, IFN-α is a paradoxical type I interferon cytokine that can prevent or limit virus replication while promoting a deleterious chronic immune activation. Because chronic immune activation is necessary for HIV replication, IFN-α thus can play a deleterious role during HIV infection. Moreover, as demonstrated by the inventors, IFN-α has an anti-proliferative activity that inhibits the proliferation of $CD4^+$ T cells, and therefore leads to immune decline, virus replication and AIDS in infected patients. Thus, by the blockade of IFN-α, the Applicant aims to potentiate type III interferon activities, therefore promoting a lower chronic immune activation and a better response of $CD4^+$ T cells.

In the present invention, the Applicant thus provides a novel method for preventing or treating an infectious disease in a subject in need thereof comprising administering to the subject:

1) a CD8 vaccine specific for at least one infectious disease-related antigen,
2) optionally an interferon alpha blocking agent, and
3) a type III interferon and/or an agent stimulating the production of type III interferon.

SUMMARY

The present invention relates to a method for preventing or treating acquired immune deficiency syndrome (AIDS) in a subject in need thereof, comprising administering to the subject:

1) a CD8 vaccine specific for at least one human immunodeficiency virus (HIV) antigen,
2) optionally interferon-alpha blocking agent, and
3) a type III interferon and/or an agent stimulating the production of type III interferon.

In one embodiment, the type III interferon comprises at least one IFN-λ selected from the group of IFN-λ1, IFN-λ2 IFN-λ3 and IFN-λ4, and wherein the agent stimulating the production of type III interferon comprises at least one TLR ligand, RIG-I ligand, and/or MDA5 ligand.

In one embodiment, the interferon-alpha blocking agent is selected from the group of: an agent neutralizing circulating alpha interferon, an agent blocking interferon-alpha signaling, an agent depleting IFN-α producing cells, and/or an agent blocking IFN-α production, wherein the agent neutralizing circulating alpha interferon is selected from the group comprising active anti-IFN-α vaccine including antiferon or passive anti-IFN-α vaccine including anti-IFN-α antibodies or anti-IFN-α hyper-immune serum, wherein the blocking agent of interferon-alpha signaling is selected from the group of anti-type I interferon R1 or R2 antibodies or from interferon-alpha endogenous regulators including SOSC1 or aryl hydrocarbon receptors, wherein the agent depleting IFN-α producing cells is an agent depleting plasmacytoid dendritic cells (pDCs), and wherein the agent blocking IFN-α production is an agent blocking the production of IFN-α by pDCs.

In one embodiment, the CD8 vaccine elicits or comprises suppressor MHC-1b/E-restricted CD8$^+$ T cells.

In one embodiment, the CD8 vaccine elicits or comprises suppressor MHC-1b/E-restricted CD8$^+$ T cells, and wherein the suppressor MHC-1b/E-restricted CD8$^+$ T cells are generated by ex vivo or in vivo induction of HLA-1a-deprived dendritic cells.

In one embodiment, the CD8 vaccine elicits or comprises suppressor MHC-1b/E-restricted CD8$^+$ T cells, wherein the suppressor MHC-1b/E-restricted CD8$^+$ T cells are generated by ex vivo or in vivo induction of HLA-1a-deprived dendritic cells, and wherein the HLA-1a-deprived dendritic cells are obtained by an agent inhibiting TAP expression or activity.

In another embodiment, the CD8 vaccine is an active vaccine, wherein the CD8 vaccine is a live viral vector comprising at least one HIV antigen, and wherein the live viral vector is selected from the group of cytomegalovirus, lentivirus, vaccinia virus, adenovirus or plasmid.

In one embodiment, the CD8 vaccine is an active vaccine, and wherein the CD8 vaccine is a cytomegalovirus (CMV) vector comprising:
  a first nucleic acid sequence encoding at least one HIV antigen,
  optionally a second nucleic acid sequence comprising a first microRNA recognition element (MRE) operably linked to a CMV gene that is essential or augmenting for CMV growth, wherein the MRE silences expression in the presence of a microRNA that is expressed by a cell of endothelial lineage;
and wherein the CMV vector does not express an active UL128 protein or ortholog thereof; does not express an active UL130 protein or ortholog thereof; does not express an active UL146 or ortholog thereof; does not express an active UL147 protein or ortholog thereof,
and wherein the CMV vector expresses at least one active UL40 protein or an ortholog thereof; expresses at least one active US27 protein or an ortholog thereof and/or expresses at least one active US28 protein or an ortholog thereof.

In one embodiment, the CD8 vaccine is a cytomegalovirus (CMV) vector, and wherein the CMV vector is a human CMV (hCMV).

In another embodiment, the CD8 vaccine is an active vaccine, and wherein the CD8 vaccine comprises at least one HIV antigen and a non-pathogenic bacterium.

In one embodiment, the CD8 vaccine comprises at least one HIV antigen and a non-pathogenic bacterium, wherein the HIV antigen is selected from the group of virus, virus particles, virus-like particles, recombinant virus, recombinant virus particles, conjugate viral proteins and concatemer viral proteins, and wherein said virus, virus particles or said recombinant virus particles are attenuated or inactivated.

In one embodiment, the CD8 vaccine comprises at least one HIV antigen and a non-pathogenic bacterium, wherein the non-pathogenic bacterium is living, and wherein said non-pathogenic bacterium is selected from attenuated or inactivated pathogenic bacteria.

In one embodiment, the CD8 vaccine comprises at least one HIV antigen and a non-pathogenic bacterium, and wherein the non-pathogenic bacterium is a *Lactobacillus bacterium*.

In one embodiment, the CD8 vaccine comprises at least one HIV antigen and a non-pathogenic bacterium, and wherein the non-pathogenic bacterium is *Lactobacillus plantarum*.

In another embodiment, the CD8 vaccine is an active vaccine, and wherein the CD8 vaccine is an ex vivo generated dendritic, natural killer or B cell population presenting MHC-1b/E-restricted and MHC-II restricted antigens, and wherein the MHC-1b/E-restricted antigen is an HIV antigen.

In another embodiment, the CD8 vaccine is a passive vaccine, and wherein the CD8 vaccine is an ex vivo generated autologous MHC-1b/E-restricted CD8$^+$ T cell population, and wherein the MHC-1b/E-restricted CD8$^+$ T cell population recognizes an MHC-1b/E-restricted HIV antigen.

In one embodiment, the HIV antigen is derived from any HIV strain, and wherein the HIV antigen is selected from the group consisting of HIV gag, HIV env, HIV rev, HIV tat, HIV nef, HIV pol, and HIV vif antigens.

In one embodiment, the HIV antigen is an HIV-derived HLA-E-binding antigen.

In one embodiment, the HIV antigen is a HIV-derived HLA-E-binding antigen, and wherein the HIV-derived HLA-E-binding antigen is selected from the antigens of SEQ ID NO: 1 to SEQ ID NO: 4.

In one embodiment, the method is for preventing acquired immune deficiency syndrome (AIDS) in a subject in need thereof.

In one embodiment, the method is for prophylactically treating acquired immune deficiency syndrome (AIDS) in a subject in need thereof.

Definitions

In the present invention, the following terms have the following meanings:
  "About" preceding a figure encompasses plus or minus 10%, or less, of the value of said figure. It is to be understood that the value to which the term "about" refers is itself also specifically, and preferably, disclosed.
  As used herein, the term "adjuvant" refers to a compound or combination of compounds that helps and enhances the pharmacological effect of a drug or a vaccine, or increases an immunogenic response, including a CD8$^+$ immune response (e.g., an immune response characterized by a high percentage of the CD8$^+$ T cell response being restricted by MHC-Ib/E used in an infectious disease treatment).
  The term "administering" means either directly administering a compound or composition of the present invention, or administering a prodrug, derivative or analog which will form an equivalent amount of the active compound or substance within the body. For example, according to one embodiment, the fact to administer a subject with an agent, such as a composition comprising an effective amount of an HCMV vector comprising an exogenous antigen by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

The term "antigen" refers to a compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance. In some embodiments, the antigen is a pathogen-specific antigen. In the context of the present disclosure, a pathogen-specific antigen is an antigen that elicits an immune response against the pathogen and/or is unique to a pathogen (such as a virus, bacterium, fungus or protozoan).

The term "attenuated", in the context of a live virus or bacterium, refers to a virus or bacterium with reduced (for example, eliminated) ability to infect a cell or subject and/or reduced (for example, eliminated) ability to induce or cause disease compared to a wild-type virus or wild-type bacterium. Typically, an attenuated virus or bacterium retains at least some capacity to elicit an immune response following administration to an immunocompetent subject. In some cases, an attenuated virus or bacterium is capable of eliciting a protective immune response without causing any signs or symptoms of infection. In some embodiments, the ability of an attenuated virus or bacterium to cause disease in a subject is reduced at least about 10%, at least about 25%, at least about 50%, at least about 75% or at least about 90% relative to wild-type virus or wild-type bacterium.

The term "CMV" (cytomegalovirus) refers to a member of the beta subclass of the family of herpesviruses. CMV is a large (~230 kB genome), double stranded DNA virus, with host-range specific variants such as MCMV (murine CMV), RhCMV (rhesus CMV) and HCMV (human CMV). In the context of the present invention, "RhCMV" refers to any strain, isolate or variant of rhesus CMV. In the context of the present invention, "HCMV" refers to any strain, isolate or variant of human CMV.

The term "decrease" refers to reducing the quality, amount, or strength of something. For example, a therapy (such as the methods provided herein) decreases the infectious load or titer of a pathogen, or one or more symptoms associated with infection.

The term "deletion" refers to the removal of a sequence of DNA, the regions on either side of the removed sequence being joined together.

The term "expression" refers to the translation of a nucleic acid into a protein, for example the translation of an mRNA encoding a tumor-specific or pathogen-specific antigen into a protein.

The term "expression control sequences" refers to nucleic acid sequences that regulate the expression of a heterologous nucleic acid sequence to which it is operatively linked, for example the expression of a heterologous polynucleotide spliced in a CMV genome and encoding an antigenic protein operably linked to expression control sequences. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, and maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter. A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., Methods in Enzymology 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. A polynucleotide can be inserted into an expression vector, including a viral vector, containing a promoter sequence, which facilitates the efficient transcription of the inserted genetic sequence of the host. The expression vector typically contains an origin of replication, a promoter, as well as specific nucleic acid sequences that allow phenotypic selection of the transformed cells.

The term "fragment" refers to a portion of a polypeptide that exhibits at least one useful epitope. The phrase "functional fragment(s) of a polypeptide" refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen.

As used herein, the term "heterologous" refers to a heterologous polypeptide or polynucleotide (such as, for example antigen or a protein) derived from a different source or species. In some embodiments of the invention, the heterologous sequence is from a different genetic source, such as a virus or other organism, than the second sequence. In particular examples, the heterologous antigen is not derived from CMV.

The term "immunogenic peptide" (or "antigenic peptide") refers to a peptide which comprises an allele-specific motif or other sequence, such as an N-terminal repeat, such that the peptide will bind an MHC molecule and induce a cytotoxic T lymphocyte ("CTL") response, or a B cell response (for example antibody production) against the antigen from which the immunogenic peptide is derived. In one embodiment, immunogenic peptides are identified using sequence motifs or other methods, such as neural net or polynomial determinations known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

The term "immunity" refers to the state of being able to mount a protective response upon exposure to an immunogenic agent. Protective responses can be antibody-mediated or immune cell-mediated, and can be directed toward a particular pathogen or tumor antigen. Immunity can be acquired actively (such as by exposure to an immunogenic agent, either naturally or in a pharmaceutical composition) or passively (such as by administration of antibodies or in vitro stimulated and expanded T cells).

The term "isolated" or "non-naturally occurring" with reference to a biological component (such as a nucleic acid molecule, protein organelle or cells), refers to a biological component altered or removed from the natural state. For example, a nucleic acid or a peptide naturally present in a living animal is not "isolated," but the same nucleic acid or peptide partially or completely separated from the coexisting materials of its natural state is "isolated". An isolated nucleic acid or peptide can exist in substantially purified form, or can exist in a non-native environment such as, for example, a host cell. Typically, a preparation of isolated nucleic acid or peptide contains the nucleic acid or peptide at least about 80% pure, at least about 85% pure, at least about 90% pure, at least about 95% pure, greater than 95% pure, greater than about 96% pure, greater than about 97% pure, greater than about 98% pure, or greater than about 99% pure. Nucleic acids and proteins that are "non-naturally occurring" or have been "isolated" include nucleic acids and proteins purified by standard purification methods. The term also embraces nucleic acids and proteins prepared by recombinant expression in a host cell as well as chemically synthesized nucleic acids. An "isolated polypeptide" is one that has been identified and separated and/or recovered from a component of its natural environment.

The terms "individual," and "patient" are used interchangeably herein, and refer to an animal, for example a human, to whom treatment, including prophylactic treatment, with the pharmaceutical composition according to the present invention, is provided.

The term "subject" as used herein refers to mammals, primates and/or humans and include all mammals, e.g., mammals, such as non-human primates, (particularly higher primates), sheep, dog, rodent, (e.g., mouse or rat), guinea pig, goat, pig, cat, rabbits, cows, horses.

The term "mutation" refers to any difference in a nucleic acid or polypeptide sequence from a normal, consensus or "wild type" sequence. A mutant is any protein or nucleic acid sequence comprising a mutation. In addition a cell or an organism with a mutation may also be referred to as a mutant. Some types of coding sequence mutations include point mutations (differences in individual nucleotides or amino acids); silent mutations (differences in nucleotides that do not result in an amino acid changes); deletions (differences in which one or more nucleotides or amino acids are missing, up to and including a deletion of the entire coding sequence of a gene); frameshift mutations (differences in which deletion of a number of nucleotides indivisible by 3 results in an alteration of the amino acid sequence. A mutation that results in a difference in an amino acid may also be called an amino acid substitution mutation. Amino acid substitution mutations may be described by the amino acid change relative to wild type at a particular position in the amino acid sequence.

As used herein, an "inactivating mutation" is any mutation in a viral gene which finally leads to a reduced function or to a complete loss of function of the viral protein.

The term "operably linked" refers to a first nucleic acid sequence that is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

The term "open reading frame" (ORF) refers to a series of nucleotide triplets (codons) coding for amino acids without any internal termination codons. These sequences are usually translatable into a peptide.

As used herein, the terms "prevent", "preventing" and "prevention" refer to preventative measures, wherein the object is to reduce the chances that a subject will develop the pathologic condition or disorder over a given period of time. Such a reduction may be reflected, e.g., in a delayed onset of at least one symptom of the pathologic condition or disorder in the subject.

The term "prophylactic" refers to a treatment administered to a subject who does not exhibit signs of a disease or exhibits only early signs for the purpose of decreasing the risk of developing pathology. In particular, a prophylactic treatment of a HIV or SIV infection in a subject refers to a treatment that allows the subject to become an elite controller (EC) i.e. to have a relatively high CD4+ T cell count (such as e.g. superior to 500 CD4+ T cells per microliter) and/or to maintain clinically undetectable plasma HIV-1 RNA level (such as e.g. HIV RNA<50 copies/mL) during a prolonged period of time in the absence of any antiretroviral treatment (ART).

The term "therapeutic" refers to a treatment administered to a subject who exhibit early or established signs of a disease.

The term "curative" refers to a treatment administered to a subject suffering from a disease for the purpose of curing the disease, i.e. of making any sign of the disease disappear or becoming undetectable.

The term "polynucleotide" refers to a polymer of ribonucleic acid (RNA) or deoxyribonucleic acid (DNA). A polynucleotide is made up of four bases; adenine, cytosine, guanine, and thymine/uracil (uracil is used in RNA). A coding sequence from a nucleic acid is indicative of the sequence of the protein encoded by the nucleic acid.

The terms "protein", "peptide", "polypeptide", and "amino acid sequence" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "purified" does not require absolute purity; rather, it is intended as a relative term. Thus, for example, a purified protein preparation is one in which the protein referred to is purer than the protein in its natural environment within a cell or within a production reaction chamber (as appropriate).

The term "recombinant" refers to a nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

The term "sample" or "biological sample" refers to a biological specimen obtained from a subject, such as a cell, fluid of tissue sample. In some cases, biological samples contain genomic DNA, RNA (including mRNA and microRNA), protein, or combinations thereof. Examples of samples include, but are not limited to, saliva, blood, serum, urine, spinal fluid, tissue biopsy, surgical specimen, cells (such as PBMCs, white blood cells, lymphocytes, or other cells of the immune system) and autopsy material.

The term "sequence identity" refers to the similarity between two nucleic acid sequences, or two amino acid sequences, is expressed in terms of the similarity between the sequences, and otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (Adv. Appl. Math. 2: 482, 1981); Needleman and Wunsch (J. Mol. Biol. 48: 443, 1970); Pearson and Lipman (PNAS USA 85: 2444, 1988); Higgins and Sharp (Gene, 73: 237-244, 1988); Higgins and Sharp (CABIOS 5: 151-153, 1989); Corpet et al. (Nuc. Acids Res. 16: 10881-10890, 1988); Huang et al. (Comp. Appls Biosci. 8: 155-165, 1992); and Pearson et al. (Meth. Mol. Biol. 24: 307-31, 1994). Altschul et al. (Nature Genet., 6: 119-129, 1994) presents a detailed consideration of sequence alignment methods and homology calculations. The alignment tools ALIGN (Myers and Miller, CABIOS 4:11-17, 1989) or LFASTA (Pearson and Lipman, 1988) may be used to perform sequence comparisons (Internet Program© 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol. 215:403-410, 1990; Gish. & States, Nature Genet. 3:266-272, 1993; Madden et al. Meth. Enzymol. 266:131-141, 1996; Altschul et al., Nucleic Acids Res. 25:3389-3402, 1997; and Zhang & Madden, Genome Res. 7:649-656, 1997.

Orthologs of proteins are typically characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of particular domains of the disclosed peptides.

When significantly less than the entire sequence is being compared for sequence identity, homologous sequences will typically possess at least 80% sequence identity over short windows of 10-20 amino acids, and may possess sequence identities of at least 85%, at least 90%, at least 95%, or at least 99% depending on their similarity to the reference sequence. Sequence identity over such short windows can be determined using LFASTA; methods are described at the NCSA Website. One of skill in the art will appreciate that these sequence identity ranges are provided for guidance only; it is entirely possible that strongly significant homologs could be obtained that fall outside of the ranges provided.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

As used herein, the term "treatment" refers to an intervention that ameliorates a sign or symptom of a disease or pathological condition. For example, in case of HIV infection, HIV RNA (viral load) and CD4 T lymphocyte (CD4) cell count are the two surrogate markers of antiretroviral treatment (ART) responses and HIV disease progression that have been used for decades to manage and monitor HIV infection.

Thus, the efficacy of the treatment may be evaluated by the plasma viral RNA load of a "treated" human before and after the treatment, if it is reduced by at least about 10%, 20%, 30%, 40%, 50%, more preferably by at least about 70%, yet more preferably by at least about 75% or 80% or 85% or 90% or 95% or 98% or 99%, or even more (99.5%, 99.8%, 99.9%, 100%) the treatment is considered as effective, and/or by the monitoring of CD4 cell count before and after the treatment, if the absolute count of CD4 cell is increased by at least about 5%, 10%, 15%, 20%, 25%, more preferably by at least about 30%, yet more preferably by at least about 35% or 40% or 45% or 50% or 55% or 60% or 65%, or even more the treatment is considered as effective. As used herein, the terms "treatment", "treat" and "treating," with reference to a disease, pathological condition or symptom, also refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease. A therapeutic treatment is a treatment administered to a subject after signs and symptoms of the disease have developed. A prophylactic treatment is a treatment administered to a subject who does not exhibit signs of a disease or exhibits only early signs, for the purpose of decreasing the risk of developing pathology. In particular, a prophylactic treatment of a HIV or SIV infection in a subject refers to a treatment that allows the subject to become an elite controller (EC) i.e. to have a relatively high $CD4^+$ T cell count (such as e.g. superior to 500 $CD4^+$ T cells per microliter) and/or to maintain clinically undetectable plasma HIV-1 RNA level (such as e.g.

HIV RNA<50 copies/mL) during a prolonged period of time in the absence of any antiretroviral treatment (ART). A prophylactic treatment is a treatment administered to a subject suffering from a disease for the purpose of curing the disease, i.e. of making any sign of the disease disappear or becoming undetectable.

The term "vector" may include nucleic acid sequences that permit it to replicate in a host cell, such as an origin of replication. A vector may also include one or more selectable marker genes and other genetic elements known in the art, including promoter elements that direct nucleic acid expression. Vectors can be viral vectors, such as CMV vectors. Viral vectors may be constructed from wild type or attenuated virus, including replication deficient virus. Vectors can also be non-viral vectors, including any plasmid known to the art.

The term "virus" refers to microscopic infectious organism that reproduces inside living cells. A virus consists essentially of a core of nucleic acid (the viral genome) surrounded by a protein coat (capsid), and has the ability to replicate only inside a living cell. "Viral replication" is the production of additional virus particles by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so. The term "lytic" or "acute" viral infection refers to a viral infection wherein the viral genome is replicated and expressed, producing the polypeptides necessary for production of the viral capsid. Mature viral particles exit the host cell, resulting in cell lysis. Particular viral species can alternatively enter into a "lysogenic" or "latent" infection. In the establishment of latency, the viral genome is replicated, but capsid proteins are not produced and assembled into viral particles.

As used herein, the term "microRNA" or "miRNA" refers to a major class of biomolecules involved in control of gene expression. For example, in human heart, liver or brain, miRNAs play a role in tissue specification or cell lineage decisions. In addition, miRNAs influence a variety of processes, including early development, cell proliferation and cell death, and apoptosis and fat metabolism. The large number of miRNA genes, the diverse expression patterns, and the abundance of potential miRNA targets suggest that miRNAs may be a significant source of genetic diversity.

A mature miRNA is typically an 18-25 nucleotide non-coding RNA that regulates expression of an mRNA including sequences complementary to the miRNA. These small RNA molecules are known to control gene expression by regulating the stability and/or translation of mRNAs. For example, miRNAs bind to the 3' UTR of target mRNAs and suppress translation. MiRNAs may also bind to target mRNAs and mediate gene silencing through the RNAi pathway. MiRNAs may also regulate gene expression by causing chromatin condensation.

A miRNA silences translation of one or more specific mRNA molecules by binding to a miRNA recognition element (MRE), which is defined as any sequence that directly base pairs with and interacts with the miRNA somewhere on the mRNA transcript. Often, the MRE is present in the 3' untranslated region (UTR) of the mRNA, but it may also be present in the coding sequence or in the 5' UTR. MREs are not necessarily perfect complements to miRNAs, usually having only a few bases of complementarity to the miRNA and often containing one or more mismatches within those bases of complementarity. The MRE may be any sequence capable of being bound by a miRNA sufficiently that the translation of a gene to which the MRE is operably linked (such as a CMV gene that is essential or augmenting for growth in vivo) is repressed by a miRNA silencing mechanism such as the RISC.

DETAILED DESCRIPTION

This invention relates to a method for preventing or treating an infectious disease in a subject in need thereof, comprising administering to the subject:

1) a CD8 vaccine specific for at least one infectious disease-related antigen,
2) an interferon alpha blocking agent, and/or
3) a type III interferon and/or an agent stimulating the production of type III interferon.

In one embodiment, the method comprises administering to the subject 1) a CD8 vaccine specific for at least one infectious disease-related antigen, 2) an interferon alpha blocking agent, and 3) a type III interferon and/or an agent stimulating the production of type III interferon.

In another embodiment, the method comprises administering to the subject 1) a CD8 vaccine specific for at least one infectious disease-related antigen and 2) an interferon alpha blocking agent.

In another embodiment, the method comprises administering to the subject 1) a CD8 vaccine specific for at least one infectious disease-related antigen and 3) a type III interferon and/or an agent stimulating the production of type III interferon.

In some embodiments, the method is a method of prophylactic treatment or a method of curative treatment.

In a particular embodiment, the method is a prophylactic method and comprises administering to the subject 1) a CD8 vaccine specific for at least one infectious disease-related antigen, 2) an interferon alpha blocking agent, and 3) a type III interferon and/or an agent stimulating the production of type III interferon.

The present invention further relates to a combination for use as a medicament, wherein said combination comprises:
1) a CD8 vaccine specific for at least one infectious disease-related antigen,
2) an interferon alpha blocking agent, and/or
3) a type III interferon and/or an agent stimulating the production of type III interferon.

The present invention also relates to a combination for use in the prevention or treatment of an infectious disease in a subject in need thereof, wherein said combination comprises:
1) a CD8 vaccine specific for at least one infectious disease-related antigen,
2) an interferon alpha blocking agent, and/or
3) a type III interferon and/or an agent stimulating the production of type III interferon.

In one embodiment, the combination for use comprises 1) a CD8 vaccine specific for at least one infectious disease-related antigen, 2) an interferon alpha blocking agent, 3) and a type III interferon and/or an agent stimulating the production of type III interferon.

In one embodiment, the combination for use comprises 1) a CD8 vaccine specific for at least one infectious disease-related antigen and 2) an interferon alpha blocking agent.

In one embodiment, the combination for use comprises 1) a CD8 vaccine specific for at least one infectious disease-related antigen and 3) a type III interferon and/or an agent stimulating the production of type III interferon.

In a particular embodiment, the combination is to be used prophylactically and comprises 1) a CD8 vaccine specific for at least one infectious disease-related antigen, 2) an interferon alpha blocking agent, and 3) a type III interferon and/or an agent stimulating the production of type III interferon.

The present invention further relates to a kit-of-parts for use in the prevention or treatment of an infectious disease in a subject in need thereof, wherein said kit-of-parts comprises at least 2 parts, and comprises:
1) a first part comprising a CD8 vaccine specific for at least one infectious disease-related antigen,
2) optionally a second part comprising an interferon-alpha blocking agent, and
3) a third part comprising a type III interferon and/or an agent stimulating the production of type III interferon.

As used herein, the term "vaccine" refers to an immunogenic product or composition that can be administered to a mammal, such as a human, to confer immunity, such as passive or active immunity, to a disease or other pathological condition. Vaccines can be used preventively or therapeutically, either prophylactically or curatively. Thus, vaccines can be used to reduce the likelihood of developing a disease (such as infection) or to reduce the severity of symptoms of a disease or condition, limit the progression of the disease or condition (such as infection), or limit the recurrence of a disease or condition.

In one embodiment, the CD8 vaccine is a preventive vaccine. In another embodiment, the CD8 vaccine is a therapeutic vaccine. As used herein, a therapeutic vaccine may be a prophylactic vaccine or a curative vaccine. In some embodiments, the CD8 vaccine is a prophylactic vaccine. In other embodiments, the CD8 vaccine is a curative vaccine.

In one embodiment, the CD8 vaccine induces immunotolerance to at least one infectious disease-related antigen. In one embodiment, the CD8 vaccine is thus specific for at least one infectious diseases-related antigen.

As used herein, the terms "immunotolerance" and "Ts" are synonymous. Immunotolerance is the physiological capacity of the immune system to recognize antigens and to develop anergy generally associated with other immunological modifications to a subsequent encounter with the same antigens. In the present invention, immunotolerance is principally characterized by the activity of $CD8^+$ T cells which suppress the activation $CD4^+$ T cells that present at least one infectious diseases-related antigen. Globally, each time where one or several infectious diseases-related antigen is/are involved in the specific activation of $CD4^+$ T cells (which present epitopes derived from the infectious diseases-related antigen), the specific suppression/prevention of activation of $CD4^+$ T cell can be raised by MHC-1b/E-restricted $CD8^+$ T cells generated by the CD8 vaccines as described in the present invention.

In one embodiment, the CD8 vaccine of the invention elicits suppressor MHC-1b/E-restricted $CD8^+$ T cells. In another embodiment, the CD8 vaccine of the invention comprises or consist essentially of suppressor MHC-1b/E-restricted $CD8^+$ T cells.

As used herein, "consisting essentially of", with reference to a cell population, means that the suppressor MHC-1b/E-restricted $CD8^+$ T cell population is the only one therapeutic agent or agent with a biologic activity within said composition.

In one embodiment, the suppressor MHC-1b/E-restricted $CD8^+$ T cells are generated by ex vivo or in vivo induction of HLA-1a-deprived dendritic, natural killer or B cells.

In one embodiment, the suppressor MHC-1b/E-restricted $CD8^+$ T cells are cytolytic $CD8^+$ T cells. In one embodiment, the suppressor MHC-1b/E-restricted $CD8^+$ T cells are non-cytolytic $CD8^+$ T cells.

In one embodiment, the CD8 vaccine is an active vaccine. In another embodiment, the CD8 vaccine is a passive vaccine.

As used herein, the term "active vaccine" refers to a vaccine that induces an active immunity and refers to the process of exposing the body to an antigen to generate an adaptive immune response: the response takes days/weeks to develop but may be long lasting—even lifelong. A "passive vaccine" induces a passive immunity and refers to the process of providing, for example, antibodies or cells to protect against infection; it gives immediate, but short-lived protection—several weeks to months.

In some embodiments, the CD8 vaccine comprises suppressor MHC-1b/E-restricted CD8+ T cells.

In some embodiments, the CD8 vaccine is a vaccine eliciting suppressor MHC-1b/E-restricted CD8+ T cells, said vaccine being selected from the group consisting of:
- an active vaccine which is a live viral vector comprising at least one pathogen-specific antigen, wherein the live viral vector is selected from the group consisting of cytomegalovirus, lentivirus, vaccinia virus, adenovirus and plasmid;
- an active vaccine comprising at least one pathogen-specific antigen and at least one non-pathogenic bacterium, preferably at least one attenuated or inactivated pathogenic bacterium;
- an active vaccine which is an ex vivo generated dendritic, natural killer or B cell population presenting at least one MHC-1b/E-restricted antigen and at least one MHC-II restricted antigen, and wherein the MHC-1b/E-restricted antigen is a pathogen-specific antigen.
- a passive vaccine which is an ex vivo generated autologous MHC-1b/E-restricted CD8+ T cell population, recognizing an MHC-1b/E-restricted pathogen-specific antigen.

According to one embodiment of the invention, the CD8 vaccine is a live viral vector comprising at least one infectious diseases-related antigen.

In one embodiment, the live viral vector, as described hereinabove, is an active vaccine. In one embodiment, the live viral vector, as described hereinabove, is selected from the group of cytomegalovirus, lentivirus, vaccinia virus, adenovirus and plasmid.

In one embodiment, the live viral vector, as described hereinabove, is a recombinant vector selected from the group of recombinant cytomegalovirus, recombinant lentivirus, recombinant vaccinia virus, recombinant adenovirus and recombinant plasmid.

According to one embodiment, the live viral vector is a recombinant vaccinia virus. Recombinant vaccinia viruses have been produced from different Vaccinia virus strains. For example, a variety of highly attenuated, host-restricted, non- or poorly-replicating poxvirus strains for use as substrates in recombinant vaccine development have been developed, including the Orthopoxviruses, Modified Vaccinia Ankara (MVA), NYVAC, Avipoxviruses, ALVAC, and TROVAC.

According to one embodiment of the invention, the CD8 vaccine is a CMV vector.

In one embodiment, the CMV vector is an active vaccine.

In one embodiment, the CMV vector comprises a nucleic acid sequence that encodes at least one infectious disease-related antigen. In a particular embodiment, the CMV vector comprises a nucleic acid sequence that encodes at least one human immunodeficiency virus (HIV) antigen.

In one embodiment, the CD8 vaccine is a recombinant CMV expressing at least one infectious diseases-related antigen, wherein said antigen is a heterologous antigen. Thus, in one embodiment, the infectious diseases-related antigen can be derived from any protein that is not natively expressed in CMV.

In one embodiment, the CMV vector does not express an active UL128 and UL130 proteins, or orthologs thereof.

As used herein, the term "ortholog" refers to homologous genes of CMVs that infect other species.

In one embodiment, the CMV vector does not express an active UL146 and UL147 proteins, or orthologs thereof.

In one embodiment, the CMV vector expresses at least one active UL40 protein, and/or at least one active US27 protein, and/or at least one active US28 protein. In one embodiment, the at least one active UL40 protein, the at least one active US27 and the at least one active US28 protein can be orthologs or homologs of UL40, US27 and US28.

In some examples, the CMV vector does not express an active UL128, UL130, UL146 or UL147 protein due to the presence of a mutation in the nucleic acid sequence encoding UL128, UL130, UL146 or UL147, or orthologs thereof.

As used herein, the term "mutation" may refer to any mutation that results in a lack of expression of active UL128, UL130, UL146 or UL147 protein. Such mutations can include point mutations, frameshift mutations, deletions of less than all of the sequence that encodes the protein (truncation mutations), or deletions of all of the nucleic acid sequence that encodes the protein, or any other mutations. For example, CMV comprising said mutation are described in WO2014138209, which is incorporate by reference herein in its entirety.

In further examples, the vector does not express an active UL128, UL130, UL146 or UL147 protein, or an ortholog thereof, due to the presence of a nucleic acid sequence in the vector that comprises an antisense or RNAi sequence (siRNA or miRNA) that inhibits the expression of the UL128, UL130, UL146 or UL147 protein, or an ortholog thereof.

In one embodiment, mutations and/or antisense and/or RNAi can be used in any combination to generate a CMV vector lacking active UL128, UL130, UL146 or UL147, or an ortholog thereof.

In one embodiment, the CMV vectors comprises all of the above modifications and further comprises a nucleic acid sequence that serves as a miRNA response element (MRE) that silences expression in the presence of a miRNA expressed by endothelial cells.

As used herein, the term "miRNA response element" or "MRE" refers to any sequence that directly base pairs with and interacts with the miRNA somewhere on the mRNA transcript. Thus, a miRNA may silence the translation of one or more specific mRNA molecules by binding to a miRNA recognition element (MRE). Often, the MRE is present in the 3' untranslated region (UTR) of the mRNA, but it may also be present in the coding sequence or in the 5' UTR. MREs are not necessarily perfectly complementary to miRNAs, usually having only a few bases of complementarity to the miRNA and often containing one or more mismatches within those bases of complementarity. The MRE may be any sequence capable of being bound by a miRNA sufficiently that the translation of a gene to which the MRE is operably linked. Examples of such genes include without limitation IE2 and UL79 genes, or orthologs thereof, or any CMV gene that is essential or augmenting for growth in vivo. For example, CMV comprising said MRE are described in WO201875591, which is incorporate by reference herein in its entirety.

In one embodiment, the MRE may be any miRNA recognition element that silences expression in the presence of a miRNA expressed by endothelial cells. In one embodiment, an MRE of the vector silences expression in the presence of one or more of miR-126-3p, miR-130a, miR-210, miR-221/222, miR-378, miR-296, and miR-328.

In one embodiment, the MRE silences expression in the presence of miR-126-3p.

In one embodiment, the MRE silences the expression of UL122 (IE2) and UL79 in the presence of miR-126-3p.

One of skill in the art may select a validated, putative, or mutated MRE sequence from the literature that would be predicted to induce silencing in the presence of a miRNA expressed in an endothelial cell or a myeloid cell such as a macrophage. The person of skill in the art may then obtain an expression construct whereby a reporter gene (such as a fluorescent protein, enzyme or other reporter gene) has expression driven by a promoter such as a constitutively active promoter or cell-specific promoter. The MRE sequence may then be introduced into the expression construct. The expression construct may be transfected into an appropriate cell, and the cell transfected with the miRNA of interest. A lack of expression of the reporter gene indicates that the MRE silences gene expression in the presence of the miRNA.

In one embodiment, the CMV vector comprises a first nucleic acid sequence encoding at least one infectious diseases-related antigen, and does not express an active UL128, UL130, UL146 and UL147 proteins or orthologs thereof, and expresses at least one active UL40, US27 and/or US28 proteins or an orthologs thereof.

In another embodiment, the CMV vector comprises a first nucleic acid sequence encoding at least one infectious diseases-related antigen, optionally a second nucleic acid sequence comprising a first microRNA recognition element (MRE) operably linked to a CMV gene that is essential or augmenting for CMV growth, wherein the MRE silences expression in the presence of a microRNA that is expressed by a cell of endothelial lineage, and does not express an active UL128, UL130, UL146 and UL147 proteins or orthologs thereof, and expresses at least one active UL40, US27 and/or US28 proteins or an orthologs thereof.

In one embodiment, the CMV vector can comprise additional inactivating mutations known in the art to provide different immune responses, such as an inactivating US11 mutation or an inactivating UL82 (pp71) mutation, or any other inactivating mutation.

In one embodiment, the CMV vector may also comprise at least one inactivating mutations in one or more viral genes encoding viral proteins known in the art to be essential or augmenting for viral dissemination (i.e., spread from cell to cell) in vivo.

Such inactivating mutations may result from point mutations, frameshift mutations, truncation mutations, or a deletion of all of the nucleic acid sequence encoding the viral protein. Inactivating mutations include any mutation in a viral gene which finally leads to a reduced function or to a complete loss of function of the viral protein.

In one embodiment, the CMV vectors described herein can contain mutations that can prevent host to host spread, thereby rendering the virus unable to infect immunocompromised or other subjects that could face complications as a result of CMV infection. In another embodiment, the CMV vectors described herein can also contain mutations that result in the presentation of immunodominant and non-immunodominant epitopes as well as non-canonical MHC restriction. Such CMV mutations are described in, for example, US Patent Publications 2013-0136768; 2014-0141038; and PCT application publication WO 2014/138209, all of which are incorporated by reference herein.

In one embodiment, mutations in the CMV vectors described herein do not affect the ability of the vector to re-infect a subject that has been previously infected with CMV. Accordingly, in one embodiment, the CMV vector is capable of repeatedly infecting an organism.

In one embodiment, the CMV vector is a human CMV (hCMV) or rhesus CMV (RhCMV) vector.

In on embodiment, the CMV vectors disclosed herein can be prepared by inserting DNA comprising a sequence that encodes the infectious disease-related antigen into an essential or non-essential region of the CMV genome.

In one embodiment, the infectious disease-related antigen is a heterologous antigen of the CMV.

In one embodiment, the method can further comprise deleting one or more regions from the CMV genome. In one embodiment, the method can comprise in vivo recombination. Thus, the method can comprise transfecting a cell with CMV DNA in a cell-compatible medium in the presence of donor DNA comprising the heterologous DNA flanked by DNA sequences homologous with portions of the CMV genome, whereby the heterologous DNA is introduced into the genome of the CMV, and optionally then recovering CMV modified by the in vivo recombination.

In one embodiment, the method can also comprise cleaving CMV DNA to obtain cleaved CMV DNA, ligating the heterologous DNA to the cleaved CMV DNA to obtain hybrid CMV-heterologous DNA, transfecting a cell with the hybrid CMV-heterologous DNA, and optionally then recovering CMV modified by the presence of the heterologous DNA. Since in vivo recombination is comprehended, the method accordingly also provides a plasmid comprising donor DNA not naturally occurring in CMV encoding a polypeptide foreign to CMV, the donor DNA is within a segment of CMV DNA that would otherwise be co-linear with an essential or non-essential region of the CMV genome such that DNA from an essential or nonessential region of CMV is flanking the donor DNA. The heterologous DNA can be inserted into CMV to generate the recombinant CMV in any orientation that yields stable integration of that DNA, and expression thereof, when desired.

In one embodiment, the DNA encoding the infectious disease-related antigen in the recombinant CMV vector can also include a promoter. The promoter can be from any source such as a herpes virus, including an endogenous CMV promoter, such as a HCMV, RhCMV, murine CMV (MCMV), or other CMV promoter. The promoter can also be a non-viral promoter such as the EF1a promoter. The promoter can be a truncated transcriptionally active promoter which comprises a region transactivated with a transactivating protein provided by the virus and the minimal promoter region of the full-length promoter from which the truncated transcriptionally active promoter is derived. The promoter can be composed of an association of DNA sequences corresponding to the minimal promoter and upstream regulatory sequences. A minimal promoter is composed of the CAP site plus TATA box (minimum sequences for basic level of transcription; unregulated level of transcription); "upstream regulatory sequences" are composed of the upstream element(s) and enhancer sequence(s). Further, the term "truncated" indicates that the full-length promoter is not completely present, i.e., that some portion of the full-length promoter has been removed. And, the truncated promoter can be derived from a herpesvirus such as MCMV or HCMV, e.g., HCMV-IE or MCMV-IE. There can be up to a 40% and even up to a 90% reduction in size, from a full-length promoter, based upon base pairs. The promoter can also be a modified non-viral promoter. As to HCMV promoters, reference is made to U.S. Pat. Nos. 5,168,062 and 5,385,839 which are incorporated herein by reference. As to transfecting cells with plasmid DNA for expression therefrom, reference is made to Feigner et al. (1994), J. Biol.

Chem. 269, 2550-2561 which is incorporated herein by reference. And, as to direct injection of plasmid DNA as a simple and effective method of vaccination against a variety of infectious diseases reference is made to Ulmer et al. (1993), Science. 259:1745-49, which is incorporated herein by reference. It is therefore within the scope of this invention that the vector can be used by the direct injection of vector DNA.

Also disclosed is an expression cassette that can be inserted into a recombinant virus or plasmid comprising the truncated transcriptionally active promoter. The expression cassette can further include a functional truncated polyadenylation signal; for instance an SV40 polyadenylation signal which is truncated, yet functional. Considering that nature provided a larger signal, it is indeed surprising that a truncated polyadenylation signal is functional. A truncated polyadenylation signal addresses the insert size limit problems of recombinant viruses such as CMV. The expression cassette can also include heterologous DNA with respect to the virus or system into which it is inserted; and that DNA can be heterologous DNA as described herein.

For the disclosed infectious disease-related antigen to be expressed in the vector, the protein coding sequence of the infectious disease-related antigen should be "operably linked" to regulatory or nucleic acid control sequences that direct transcription and translation of the protein.

According to another embodiment of the invention, the CD8 vaccine comprises at least one infectious disease-related antigen and a non-pathogenic bacterium.

In one embodiment, the CD8 vaccine comprises at least one infectious disease-related antigen and at least one non-pathogenic bacterium.

In one embodiment, the CD8 vaccine that comprises at least one infectious disease-related antigen and a non-pathogenic bacterium is an active vaccine.

As used herein, the term "non-pathogenic bacterium" refers to bacteria that do not generally induce any pathology in mammals, preferably in humans.

In one embodiment, the non-pathogenic bacterium is living.

In one embodiment, the non-pathogenic bacterium described herein is a commensal bacterium.

As used herein, the term "commensal bacterium" or refers to micro-organism, which is present on body surfaces covered by epithelial cells and is exposed to the external environment (e.g., gastrointestinal and respiratory tract, vagina, skin, etc.). Among the numerous proposed health benefits attributed to intestinal commensal bacteria, their capacity to interact with the host immune system is now well demonstrated. Commensal bacteria are well-known to the skilled artisan. Non-limiting examples include *Bacillus* sp. (e.g., *B. coagulans*), *Lactobacillus* sp., *Bifidobacterium animalis*, *Bifidobacterium breve*, *Bifidobacterium infantis*, *Bifidobacterium longum*, *Bifidobacterium bifidum*, *Bifidobacterium lactis*, *Escherichia coli*, *Lactobacillus acidophilus*, *Lactobacillus bulgaricus*, *Lactobacillus casei*, *Lactobacillus paracasei*, *Lactobacillus johnsonii*, *Lactobacillus plantarum*, *Lactobacillus reuteri*, *Lactobacillus rhamnosus*, *Lactobacillus brevis*, *Lactobacillus gasseri*, *Lactobacillus salivarius*, *Lactobacillus salivarius salicinius*, *Lactobacillus delbureckii*, *Lactobacillus delbureckii bulgaricus*, *Lactobacillus delbureckii lactis*, *Lactococcus lactis*, *Streptococcus thermophilus*, and the like.

In one embodiment, the commensal bacterium is selected from the group of *Lactobacillus acidophilus*, *Lactobacillus rhamnosus*, *Lactobacillus plantarum*, *Bifidobacterium bifidum*, *Bifidobacterium breve*, *Lactococcus lactis*, *Streptococcus thermophilus*, *Lactobacillus casei*, *Lactobacillus acidophilus*, *Lactobacillus reuteri*.

In one embodiment, the commensal bacterium is *Lactobacillus* sp., preferably *Lactobacillus plantarum*.

In another embodiment, the commensal bacterium is *Lactobacillus* sp., preferably *Lactobacillus rhamnosus*.

In one embodiment, a combination of non-pathogenic bacteria, such as two or more commensal bacteria, may be used.

In another embodiment, the non-pathogenic bacterium described herein is selected from attenuated or inactivated pathogenic bacteria.

As used herein, the terms "pathogenic bacteria" refer to bacteria inducing pathologies in humans. Such bacteria are well known from the skilled person and include inter alia *Listeria* species (e.g., *Listeria monocytogenes*), *Corynebacterium* species, *Mycobacterium* species, *Rhococcus* species, *Eubacteria* species, *Bortadella* species and *Nocardia* species. Preferably, a pathogenic bacterium is selected among *Mycobacterium* species, and is more preferably *Mycobacterium bovis*.

As used herein, the terms "attenuated pathogenic bacteria" refer to bacteria which are less virulent compared to their wild-type counterpart because of one or several mutations or of one or more attenuation treatments (e.g., chemical treatment and/or successive passages on specific media). Such attenuated pathogenic bacteria are well known from the one of skill in the art. Non-limiting examples of attenuated pathogenic bacteria include attenuated *Salmonella typhimurium* and Mycobacteria. Methods of preparation of such inactivated pathogenic bacteria form part of the common general knowledge in the art. As an example of such methods, one can cite phage mediated lysis, chemical inactivation such as formalin treatment, thermal inactivation, physical inactivation such as lyophilisation (e.g., Extended Freeze Drying) or U.V or gamma irradiation or microwave exposure, or any combination thereof.

In one embodiment, the non-pathogenic bacterium described herein may be recombinant or not.

In one embodiment, the attenuated pathogenic bacterium described herein is an attenuated derivative of pathogenic bacteria like BCG. In one embodiment, said attenuated derivative of pathogenic bacteria corresponds to recombinant *Salmonella typhimurium* or recombinant Mycobacteria (e.g., BCG) which expresses or produces at least one HIV protein. In another embodiment, said derivative of pathogenic bacteria does not express any HIV protein.

In one embodiment, the non-pathogenic bacterium described herein is to be used as a tolerogenic adjuvant of the CD8 vaccine. Accordingly, in one embodiment, the non-pathogenic bacterium is a tolerogenic adjuvant.

As used herein, the term "tolerogenic adjuvant" is an entity that, when administered by the mucosal or the intradermal or the intraepithelial route together with an appropriate infectious disease-related antigen as defined hereafter, will induce and will preferably maintain a state of immunotolerance to the antigen, thus enabling to treat an infectious disease infection in humans.

In one embodiment, the tolerogenic adjuvant, when combined to an infectious disease-related antigen induces or maintains immunotolerance to the viral antigen, thereby treating a related infectious disease.

In one embodiment, non-pathogenic bacteria, especially probiotics and commensal bacteria, may be used as tolerogenic adjuvant in the context of the present invention.

In a particular embodiment, *Lactobacillus* sp., preferably *Lactobacillus plantarum* and/or *Lactobacillus rhamnosus*, may be used as tolerogenic adjuvant in the context of the present invention.

In one embodiment, a combination of non-pathogenic bacteria, such as two or more commensal bacteria, may be used as the tolerogenic adjuvant in the context of the present invention.

In another embodiment, instead of or additionally to being attenuated, pathogenic bacteria described herein may be inactivated to be used as tolerogenic adjuvant in the context of the present invention, but attenuated pathogenic bacteria may also be used after having been inactivated.

In some embodiment, the tolerogenic adjuvant, comprising a non-pathogenic bacterium or an attenuated pathogenic bacterium, further comprises a prebiotic.

As used herein, "prebiotics" are substances which induce the growth or activity of certain bacteria. Prebiotics are of different nature including e.g. sugars, such as oligosaccharides and polysaccharides.

Any prebiotic may be used in combination with the non-pathogenic bacterium or the attenuated pathogenic bacterium described herein.

In some embodiments, the tolerogenic adjuvant comprises at least one prebiotic selected from the group consisting of fructooligosaccharides (FOS), galactooligosaccharides (GOS), inulin, trans-galactooligosaccharides (TOS), beneo synergy 1 (SYN1), oligofructose-inulin, lactulose, oat fibera, germinated barley, hydrolyzed guar guma, resistant starcha, plantago ovataa, beta glucana and pectina.

According to another embodiment of the invention, CD8 vaccine is an ex vivo generated dendritic, natural killer or B cell population presenting MHC-II and MHC-1b/E-restricted antigens.

In one embodiment, the ex vivo generated dendritic, natural killer or B cell population presenting MHC-II and MHC-1b/E-restricted antigens is an active vaccine.

In one embodiment, the MHC-1b/E-restricted antigen is an infectious disease-related pathogen-specific antigen.

In one embodiment, the infectious diseases-related antigen or pathogen-specific antigen is an HIV or SIV-derived MHCIb/E-binding antigen.

In one embodiment, the HIV-derived MHCIb/E-binding antigen described herein is selected from the group of SEQ ID NO: 1 to SEQ ID NO: 4.

In one embodiment, the HIV-derived MHCIb/E-binding antigen has an amino acid sequence selected from the group consisting of the sequence RMYSPVSIL (SEQ ID NO: 1), the sequence PEIVIYDYM (SEQ ID NO: 2), the sequence TALSEGATP (SEQ ID NO: 3) and the sequence RIRTWKSLV (SEQ ID NO: 4).

In some embodiments, the MHC-II-restricted peptide or antigen is an HLA-DR-restricted peptide or antigen. Examples of HLA-DR-restricted peptides include for instance the HLA-DR-binding antigens having one of the sequences QGQMVHQAISPRTLN (SEQ ID NO: 7) (Gag p24), GEIYKRWIILGLNKI (SEQ ID NO: 8) (Gag p24), KRWIILGLNKIVRMY (SEQ ID NO: 9) (Gag p24) or FRKYTAFTIPSINNE (SEQ ID NO: 10) (Pol RT).

In one embodiment, the HLA-DR-restricted peptides are derived from HIV, preferably from HIV-1.

In one embodiment, the HLA-DR-restricted peptides are HIV-derived HLA-DR-binding antigen having an amino acid sequence selected from the group consisting of the sequence QGQMVHQAISPRTLN (SEQ ID NO: 7) (Gag p24), the sequence GEIYKRWIILGLNKI (SEQ ID NO: 8) (Gag p24), the sequence KRWIILGLNKIVRMY (SEQ ID NO: 9) (Gag p24) and the sequence FRKYTAFTIPSINNE (SEQ ID NO: 10) (Pol RT).

In one embodiment, dendritic, natural killer or B cell population presenting MHC-II and MHC-1b/E-restricted peptides is an allogenic cell population. In a preferred embodiment, dendritic, natural killer or B cell population presenting MHC-II and MHC-1b/E-restricted restricted peptides is an autologous cell population.

As used herein, "allogeneic cells" refers to cells isolated from one subject (the donor) and infused in another (the recipient or host).

As used herein, "autologous cells" refers to cells that are isolated and infused back into the same subject (recipient or host).

The present invention thus also relates to an ex vivo method for generating dendritic, natural killer or B cell population presenting MHC-II and MHC-1b/E-restricted peptides.

In one embodiment, the ex vivo method for generating dendritic, natural killer or B cell population presenting MHC-II and MHC-1b/E-restricted peptides, comprises:
  a. optionally, reducing MHC-1a expression in immature dendritic, natural killer or B cells with an agent inhibiting TAP expression or activity,
  b. loading immature dendritic cells with HLA-DR and/or MHC-1b/E-restricted peptide, and
  c. maturing the loaded immature dendritic, natural killer or B cells.

In one embodiment, the immature dendritic cells are produced from monocytes dendritic cell precursors (MO-DC) precursors.

As used herein, the term "monocytes dendritic cell precursors" refers to monocytes and other bone marrow precursors (e.g., myeloid precursor). These cells can be isolated from any tissue where they reside, particularly lymphoid tissues such as the spleen, bone marrow, lymph nodes and thymus. Monocytes dendritic cell precursors can be isolated from umbilical cord blood. Monocytes dendritic cell precursors also can be isolated by any technique well known in the art from peripheral blood mononuclear cells or bone marrow samples. Monocytes dendritic cell precursors also can be isolated from frozen samples. Methods for isolating MO-DC precursors and the immature dendritic cells from the various sources provided above, including blood and bone marrow, can be accomplished in a number of ways. Typically, a cell population is collected from the individual and enriched for the MO-DC precursors. For example, a mixed population of cells comprising the MO-DC precursors can be obtained from peripheral blood by leukapheresis, apheresis, density centrifugation, differential lysis, filtration, antibody panning (e.g., flow cytometry, positive or negative selection) or preparation of a buffy coat. In one embodiment, the MO-DC precursors are non-activated thus, in one embodiment, the method selected must not activate the MO-DC precursors. For example, if antibody panning is selected to enrich the cell population for precursors the antibodies selected must not activate the cells (e.g., through the induction of the influx of calcium ions which can result as a consequence of crosslinking the molecules on the surface to which the antibodies bind). Typically, when antibody panning, antibodies are used that eliminate macrophage, B cells, Natural Killer cells, T cells and the like. Antibodies can also be used to positively select for monocyte like cells that express CD14.

In one embodiment, the MO-DC precursors and the immature dendritic cells can be obtained from autologous PBMCs (peripheral blood mononuclear cells). In one embodiment, the MO-DC precursors and the immature dendritic cells can be obtained from autologous tissues. In one embodiment, the MO-DC precursors and the immature dendritic cells can be obtained from an HLA-matched healthy individual.

In one embodiment, the immature dendritic cells can by obtain from induced pluripotent stem cells (iPS). In one embodiment, the immature dendritic cells can by obtain from CD34+ dendritic cell precursors. In one embodiment, the immature dendritic cells can by obtain from human dendritic cell lines. In one embodiment, the immature dendritic cells can by obtain from CD34+ dendritic cell precursor cell lines. A non-limiting example of a cell line that can be used to generate immature dendritic cell is the CD34+ human acute myeloid leukemia cell line (MUTZ-3), see, for example, Masterson et al., (2002) Blood, 100:701-703.

In another embodiment, the MO-DC precursors and the immature dendritic cells can be obtained from an HLA-matched healthy individual for conversion to immature dendritic cells, maturation, activation and administration to an HLA-matched subject in need thereof.

In one embodiment, the cell populations enriched form non-activated MO-DC precursors or CD34+ dendritic cell precursors are cultured ex vivo or in vitro for differentiation, maturation and/or expansion.

Briefly, ex vivo differentiation typically involves culturing the MO-DC precursors or CD34+ dendritic cell precursors, or populations of cell comprising non-activated MO-DC precursors or CD34+ dendritic cell precursors, in the presence of one or more differentiation agents. Such agents generally comprise granulocyte-macrophage colony stimulating factor (GM-CSF), interleukin 4 (IL-4), interleukin 6 (IL-6), interleukin 3 (IL-3), stem cell factor (SCF), Fms-related tyrosine kinase 3 ligand (Flt3-L) or a combination thereof. Such agents can be used alone or in combination. For example, the GM-CSF can be used alone or in combination with one or more cytokines, such as IL-4, IL-6, IL-3, SC and/or Flt3-L. In one embodiment, the non-activated MO-DC precursors or CD34+ dendritic cell precursors are differentiated to form immature dendritic cells capable of inducing the activation and proliferation of a substantial number of T cells.

Suitable culture conditions to product and maintained immature dendritic cell precursors are well known in the art. Such culture media include, without limitation, AIM-V®, RPMI 1640, DMEM, X-VIVO 15®, and the like supplemented cytokines. The culture media can be supplemented with serum, amino acids, vitamins, divalent cations, and the like, to promote differentiation of the cells into dendritic cells. In one embodiment, the dendritic cell precursors can be cultured in a serum-free media. Such culture conditions can optionally exclude any animal-derived products. Typically, GM-CSF is added to the culture medium at a concentration of about 2 to about 200 ng/ml, or typically 20 ng/ml of GM-CSF, IL-4 is added to the culture medium at a concentration of about 2 to about 200 ng/ml, or typically 20 ng/ml of IL-4. IL-6 is added to the culture medium at a concentration of about 2 to about 200 ng/ml, or typically 20 ng/ml of IL-6. IL-3 is added to the culture medium at a concentration of about 2 to about 200 ng/ml, or typically 20 ng/ml of IL-3, SCF is added to the culture medium at a concentration of about 10 to about 1000 ng/ml, or typically 100 ng/ml of SCF, and Flt3-L is added to the culture medium at a concentration of about 10 to about 1000 ng/ml, or typically 100 ng/ml of Flt3-L. Precursors, when differentiated to form immature dendritic cells, generally demonstrate a typical expression pattern of cell surface proteins seen for immature dendritic cells, e.g., the cells are typically CD14−, HLA-DR+, CD11c+, CD83− and express low levels of CD86. A non-limiting example of production of immature dendritic cell precursors is described in Example 2. At this stage, the immature dendritic cells are able to capture soluble antigens via specialized uptake mechanisms.

In one embodiment, the expression of MHC-1a in immature dendritic cells or in dendritic cells is reduced by an agent inhibiting TAP expression or activity.

According to one embodiment, the immature dendritic cells or the dendritic cells express a reduced level of the major histocompatibility class 1a (MHC-1a) molecules on their surface. According to one embodiment, the immature dendritic cells or the dendritic cells do not express the major histocompatibility class 1a (MHC-1a) on their surface.

The "MHC class 1a presentation" refers to the "classical" presentation through HLA-A, HLA-B and/or HLA-C molecules whereas the MHC class Ib presentation refers to the "non-classical" antigen presentation through HLA-E, HLA-F, HLA-G and/or HLA-H molecules.

Methods for inhibiting MHC-1a molecules expression are well-known. For example, the inhibition of the TAP transporter (transporter associated with antigen processing) leads to a decreased expression of MHC-1a molecules thereby promoting HLA-E molecules expression on the surface of dendritic cells.

Exemplary methods to inhibit the TAP transporter in the endoplasmic reticulum include, but are not limited to, CRISPR-CAS-9 technology, silencing RNA, transfected DCs with the UL-10 viral protein from the CMV (cytomegalovirus) or the use of viral proteins.

Examples of viral genes or proteins silencing TAP expression include, but are not limited to, HSV-1 ICP47 protein, varicella-virus UL49.5 protein, cytomegalovirus US6 protein or gamma herpesvirus EBV BNLF2a protein, HIV nef protein.

Another method is the use of a chemical product to inhibit the expression of MHC class 1a molecules without changing HLA-E expression on the surface of tolerogenic DCs. Examples of chemical products include, but are not limited to, 5'-methyl-5'-thioadenosine or leptomycin B.

In one embodiment, the TAP inhibitor is RNA synthesized from the pGem4Z vector containing the UL49.5 gene from BHV-1.

In one embodiment, the TAP inhibitor can be efficiently introduced into immature dendritic cells by electroporation. In another embodiment, the TAP inhibitor can be efficiently introduced into immature dendritic cells by transfection.

Depletion of MHC-1a can be monitored by methods known in the art. For example, antibodies can also be used to monitor that immature dendritic cells or dendritic cells are MHC-1a$^{−/low}$.

In one embodiment, the immature dendritic cells or dendritic cells can be loaded (or pulsed) in the presence of at least one predetermined antigen. In one embodiment, the expression of MHC-1a in immature dendritic cells or dendritic cells has been previously reduced. In another embodiment, the expression of MHC-1a in immature dendritic cells has not been previously reduced.

In one embodiment, the immature dendritic cells or dendritic cells present peptides or antigens that specifically bind to HLA-DR and/or MHC-1b/E molecules. Thus, in one embodiment, the immature dendritic can be loaded (or pulsed) by contacting immature dendritic cells or dendritic cells with a predetermined peptide or antigen either prior to, after to or during maturation. In one embodiment, the MHC-1a depleted immature dendritic cells or dendritic cells present peptides or antigens that specifically bind to HLA-DR and/or MHC-1b/E molecules. Thus, in one embodiment, the MHC-1a depleted immature dendritic can be loaded (or pulsed) by contacting immature dendritic cells with a predetermined peptide or antigen either prior to, after to or during maturation.

Suitable predetermined antigens for use in the present invention can include any infectious-diseases related antigen. Infectious-diseases related antigens are described hereafter and include, for example, HIV or SIV MHC-Ib/E peptides or antigens.

Methods for contacting dendritic cells with antigen are generally known in the art (See Steel and Nutman, J. Immunol. 160:351-60 (1998); Tao et al., J. Immunol. 158: 4237-44 (1997); Dozmorov and Miller, Cell Immunol. 178: 187-96 (1997); Inaba et al., J Exp Med. 166:182-94 (1987); Macatonia et al., J Exp Med. 169:1255-64 (1989); De Bruijn et al., Eur. J. Immunol. 22:3013-20 (1992); the disclosures of which are incorporated by reference herein). Typically, the immature dendritic immature cells obtained by the methods of the present invention can be cultured in the presence the predetermined antigen under suitable culture conditions, as described above. Optionally, the immature dendritic cells can be admixed with the predetermined antigen in a typical dendritic cell culture media with or without GM-CSF, and/or a maturation agent. Following at least about 10 minutes to about 2 days of culture with the antigen, the antigen can be removed and culture media supplemented with a maturation agent. GM-CSF and others cytokines (e.g., such as IL-4) can also be added to the culture media.

In one embodiment, the immature dendritic cells or dendritic cells can be transfected with a plasmid coding for MHC-1b/E molecules. In another embodiment, the immature dendritic cells or dendritic cells can be transfected with a plasmid coding for peptide-MHC-1b/E complex.

In one embodiment, the immature dendritic cell (optionally MHC-1a depleted and previously loaded) can be matured with a maturation agent.

In on embodiment, the immature dendritic cells can be matured to form mature dendritic cells. Mature dendritic cells lose the ability to take up antigen and the cells display up-regulated expression of co-stimulatory cell surface molecules and secrete various cytokines. For example, mature dendritic cells can express higher levels of HLA-DR and/or MHC-1b/E antigens and are generally identified as MHC-1a$^{-/low}$, CD80$^+$, CD83$^+$, and CD86$^+$. Greater MHC expression leads to an increase in antigen density on the DC surface, while up regulation of co-stimulatory molecules CD80 and CD86 strengthens the T cell activation signal through the counterparts of the co-stimulatory molecules, such as CD28 on the T cells.

Methods to prepare mature dendritic cells are well known in the art. For example, immature dendritic cells can be matured by contacting the immature dendritic cells with effective amounts or concentrations of a dendritic cell maturation agent. Dendritic cell maturation agents can include, for example, BCG, IFNγ, LPS, TNFα, IL-1β, IL-6, PGE2, Poly I:C, TLR7/8-ligand, or a combination thereof.

For example, the immature DCs are typically contacted with effective amounts of LPS for about one hour to about 48 hours, preferably for 24 hours. The immature dendritic cells can be cultured and matured in suitable maturation culture conditions. Suitable tissue culture media include AIM-V®, RPMI 1640, DMEM, X-VIVO 15®, and the like. The tissue culture media can be supplemented with amino acids, vitamins, cytokines, such as GM-CSF, divalent cations, and the like, to promote maturation of the cells.

As exemplary purpose, dendritic cells can be matured in presence of IL-1β, IL-6, PGE2, TNF-α, LPS, Poly I:C. Typically about 2 ng/ml of IL-1β, 30 ng/ml of IL-6, 1 µg/ml of PGE2, 10 ng/ml of TNF-α, 250 ng/ml of LPS, 150 ng/ml of Poly I:C are generally used.

Maturation of dendritic cells can be monitored by methods known in the art for dendritic cells. Cell surface markers can be detected in assays familiar to the art, such as flow cytometry, immunohistochemistry, and the like. The cells can also be monitored for cytokine production (e.g., by ELISA, another immune assay, or by use of an oligonucleotide array). Mature DCs of the present invention also lose the ability to uptake antigen, which can be analyzed by uptake assays familiar to one of ordinary skill in the art.

Thus, the present invention also relates to a mature dendritic cell population presenting MHC-II and MHC-1b/E-restricted peptides obtainable or obtained by the ex vivo method as described here above.

Instead of dendritic cells, other immune cell types may be used to obtain a mature immune cell population presenting MHC-II and MHC-1b/E-restricted peptides or antigen.

In one embodiment, the CD8 vaccine is an active vaccine which is an ex vivo generated natural killer cell population presenting at least one MHC-1b/E-restricted antigen and at least one MHC-II restricted antigen.

In one embodiment, the natural killer cell is a K562 cell line.

In some embodiment, the natural killer cell is modified to express MHC-1b/E.

In another embodiment, the CD8 vaccine is an active vaccine which is an ex vivo generated natural B population presenting at least one MHC-1b/E-restricted antigen and at least one MHC-II restricted antigen.

In one embodiment, the B cell is a cell line.

In some embodiment, the B cell is modified to express MHC-1b/E.

Thus, the present invention also relates to a mature natural killer cell population presenting MHC-II and MHC-1b/E-restricted peptides obtainable or obtained by the ex vivo method as described here above.

The present invention also relates to a mature B cell population presenting MHC-II and MHC-1b/E-restricted peptides obtainable or obtained by the ex vivo method as described here above.

According to another embodiment of the invention, the CD8 vaccine is an ex vivo generated MHC-1b/E-restricted CD8$^+$ T cell population.

In one embodiment, ex vivo generated MHC-1b/E-restricted CD8$^+$ T cell population is a passive vaccine.

In one embodiment, the MHC-1b/E-restricted CD8$^+$ T cell population recognizes an MHC-1b/E-restricted infectious diseases-related antigen.

The present invention thus also relates to an ex vivo method for generating MHC-1b/E-restricted CD8$^+$ T cell population.

In one embodiment, the ex vivo method for generating MHC-1b/E-restricted CD8$^+$ T cell population, comprises:
  a. culturing naïve CD8$^+$ T cells in the presence of dendritic, natural killer or B cell population presenting MHC-1b/E-restricted peptides enabling generation of MHC-1b/E-restricted CD8$^+$ T cells, and
  b. expanding the MHC-1b/E-restricted CD8$^+$ T cells.

In one embodiment, the CD8$^+$ T cells, preferably naïve CD8$^+$ T cells, are isolated by any technique well known in the art from a blood sample. In one embodiment, CD8$^+$ T cells, preferably naïve CD8+ T cells, are isolated from PBMCs (peripheral blood mononuclear cells) by flow cytometry. In one embodiment, the CD8+ T cells, preferably naïve CD8+ T cells, may be isolated from frozen PBMCs. In one embodiment, the CD8+ T cells are allogenic T cells, preferably allogenic naive T cells. In another embodiment, the CD8+ T cells are autologous T cells, preferably autologous naive T cells. T cell isolation or purification can be achieved by positive, or negative selection, including but not limited to, the use of antibodies directed to CD8, CD56, CD57, CD45RO, CD45RA, CCR7, and the like. For example, naive CD8+ T cell isolation can be performed in a one-step or two step procedure. A two-step procedure can comprise a first step wherein naive T cells are enriched by depletion of non-naive T cells, and a second step wherein the enriched naive T cells are labeled with CD8 antibodies for subsequent positive selection of the CD8+ naive T cells.

In one embodiment, the CD8+ T cells, preferably naïve CD8+ T cells, more preferably autologous naive CD8+ T cells, are stimulated with peptide or antigen pulsed dendritic cells (for example MHC-Ib/E-antigen pulsed tolerogenic dendritic cells) in presence of stimulating agent. After stimulation, cells can be washed, for example with PBS, and can be stained with anti-CD8 antibodies and using MHC-peptide pentamer for sorting. The purified CD8+ T cells are enriched and may be used for the following activation step. In one embodiment, the CD8+ T cells, preferably naïve CD8+ T cells, more preferably autologous naive CD8+ T cells are co-incubated with dendritic cells presenting MHC-1b/E-restricted peptides. In one embodiment, said dendritic cells presenting MHC-1b/E-restricted peptides also present MHC-II-restricted peptide.

In one embodiment, the dendritic cells do not express MHC-1a molecules on their surface. In one embodiment, the dendritic cells express less than 50%, 45%, 40%, 35%, 30%, 25%, 20%, 15%, 10% or 5% of MHC-1a molecules on their surface (i.e., relative to all MHC molecules expressed at the surface of the dendritic cell). In one embodiment, the dendritic cells express at least 50%, 55%, 60%, 65%, 70%, 75%, 80%, 85, 90% or 95% of MHC-1b molecules on their surface. In one embodiment, dendritic cells express only MHC-Ib molecules on their surface.

In one embodiment, dendritic cells express MHC-II molecules on their surface. In one embodiment, dendritic cells express MHC-II molecules and MHC-Ib molecules on their surface.

In one embodiment, the CD8+ T cells, preferably naïve CD8+ T cells, more preferably autologous naive CD8+ T cells, are contacted with the tolerogenic dendritic cells as described hereinabove. Accordingly, at the end of the culture, the T cells are suppressor MHC-1b/E-restricted CD8+ T cells and can induce immunotolerance.

In one embodiment, the culture for generating the MHC-1b/E-restricted CD8+ T cells of the invention is performed during at least 1 day, at least 2 days, at least 3 days, at least 4 days, at least 5 days, at least 6 days, at least 7 days, at least 8 days or more. In one embodiment, the culture for generating the MHC-1b/E-restricted CD8+ T cells of the invention is performed during at least 1 week, at least 2 weeks, at least 3 weeks, at least 4 weeks, at least 5 weeks or more. In one embodiment, the culture for generating the MHC-1b/E-restricted CD8+ T cells of the invention is performed during at least 1 month, at least 2 months, at least 3 months or more.

In one embodiment, MHC-Ib/E natural killer cells or MHC-1b/E B cells are used instead of MHC-1b/E dendritic cells in the method described herein for generating an autologous MHC-1b/E-restricted CD8+ T cell population.

In one embodiment, the MHC-1b/E-restricted CD8+ T cell population generated ex vivo is isolated by flow cytometry based on their ability to binds to specific HLA-E antigens or peptides (e.g., specific tetramers).

In one embodiment, the isolated MHC-1b/E-restricted CD8+ T cell population thus obtained is then expanded ex vivo by culturing these cells in the presence of at least one T cell activator. Examples of T cell activator include, but are not limited to, to be completed. Alternatively, other examples of T cell activators that may be used during expansion include, but are not limited to, mitogen such as PMA/ionomycin, super-antigen, anti-CD3 antibody and the like. Preferably, the anti-CD3 monoclonal antibody is coated. In one embodiment, the T cell activator can be used in the presence of feeder cells.

Feeder cells include, but are not limited to, ΔCD3 cells (T cell-depleted accessory cells), irradiated PBMCs, irradiated DCs, artificial APCs (antigen presenting cells), Sf9 cells, insect cells, a pool of PBMCs or a pool of B cells from different subjects, KCD40L cells EBV-transformed B cell lines and EBV-transformed lymphoblastoid cells (LCL).

In another embodiment, the isolated MHC-1b/E-restricted CD8+ T cell population thus obtained is then expanded ex vivo by culturing these cells in the presence of an antigen-specific T cell activator (e.g., anti-CD3/CD28 antibodies, PMA/iono, cytokines and the likes). In one embodiment, the antigen-specific T cell activator can be used in the presence of feeder cells as described here above.

In one embodiment, the culture for expanded the ex vivo MHC-1b/E-restricted CD8+ T cells of the invention is performed during at least 1 day, at least 2 days, at least 3 days, at least 4 days, at least 5 days, at least 6 days, at least 7 days, at least 8 days or more. In one embodiment, the culture for expanded the ex vivo MHC-1b/E-restricted CD8+ T cells of the invention is performed during at least 1 week, at least 2 weeks, at least 3 weeks, at least 4 weeks, at least 5 weeks or more. In one embodiment, the culture for expanded the ex vivo MHC-1b/E-restricted CD8+ T cells of the invention is performed during at least 1 month, at least 2 months, at least 3 months or more.

Thus, the present invention also relates to an MHC-1b/E-restricted CD8+ T cell obtainable or obtained by the ex vivo method as described here above.

In one embodiment, the infectious diseases-related antigen is a pathogen-specific antigen.

"Pathogenic-specific antigen" can be selected from any organism that is known to be pathogenic, or against which it is desirable to elicit an immune response. Such pathogen-specific antigens are well known in the art, therefore a suitable antigen can be selected by one of ordinary skill in the art. The antigen is chosen according to the type of infectious disease to be treated. For example, when the disease to be prevented or treated is acquired immune deficiency syndrome (AIDS) or a simian immunodeficiency virus (SIV) infection, the CD8 vaccine comprises or encodes an antigen from HIV or SIV respectively.

In one embodiment, the pathogen-specific antigen described herein can be derived from any human or animal pathogen. In one embodiment, the pathogen specific antigen is a viral pathogen, a bacterial pathogen, or a parasite, and the antigen may be a protein derived from the viral pathogen, bacterial pathogen, or parasite. In one embodiment, the parasite may be an organism or disease caused by an organism. For example, the parasite may be a protozoan organism, a protozoan organism causing a disease, a helminth organism or worm, a disease caused by a helminth organism, an ectoparasite, or a disease caused by an ectoparasite.

In one embodiment, the pathogen-specific antigen described herein can be an antigen from a viral pathogen. In one embodiment, the pathogen-specific antigen can be an antigen from a bacterial pathogen. In one embodiment, the pathogen-specific antigen can be an antigen from a parasitic organism. In another embodiment, the pathogen-specific antigen can be an antigen from a helminth organism.

In one embodiment, the pathogen-specific antigen described herein is non-infectious.

In one embodiment, when recombinant virus or bacteria are used to express the antigen, these are preferably inactivated microorganisms.

In one embodiment, the pathogen-specific antigen described herein is a particulate antigen.

In one embodiment, the pathogen-specific antigen described herein may result from the expression of a viral nucleic acid sequence advantageously contained into an appropriate recombinant microorganism. In one embodiment said recombinant microorganism is a CMV, preferably a CMV vector as described herein above. In another embodiment, said recombinant microorganism is a bacterium, preferably a different bacterium from the non-pathogenic bacterium as described herein above.

In one embodiment, the pathogen-specific antigen described herein can be codon optimized. Many viruses, including HIV and other lentiviruses, use a large number of rare codons and, by altering these codons to correspond to codons commonly used in the desired subject (for example, humans), enhanced expression of the antigens can be achieved. For example, rare codons used in HIV proteins can be mutated into those that appear frequently in highly expressed human genes (Andre et al. (1998) J Virol 72, 1497-1503).

In one embodiment, the pathogen-specific antigen described herein can be consensus sequences or mosaic antigens containing sequence fragments from different strains of pathogens.

In one embodiment, the particulate antigen described herein is a viral antigen.

In one embodiment, the particulate antigen is selected from viral particles, recombinant viral particles, virus-like particles, recombinant viral particles, polymeric microparticles presenting on their surface one or more viral peptides or epitopes, conjugate viral proteins and concatemer viral proteins.

In one embodiment, the particulate antigen described herein may be one or more viral proteins or peptides, recombinant or not, either in the form of conjugates or of concatemers.

In one embodiment, the pathogen-specific antigen described herein can be derived from the human immunodeficiency virus (HIV), simian immunodeficiency virus (SIV), herpes simplex virus, hepatitis B virus, hepatitis C virus, papillomavirus, Plasmodium parasites, and *Mycobacterium tuberculosis*.

In one embodiment, the pathogen-specific antigen described herein is an HIV or SIV antigen. In one embodiment, the HIV or SIV antigen is selected from the group consisting of any HIV or SIV strains. In one embodiment, the HIV or SIV antigen is selected from the group consisting of gag, tat, pol, vif, nef and env antigens.

In one embodiment, the pathogen-specific antigen described herein is derived from immunogenic apoptotic bodies from infected cells or derived from tissue lysate.

Infected cells may derive from tissue biopsy or from expansion of circulatory infected cells. Said infected cells can be infected by virus, bacteria, parasitic organisms or helminth organisms.

Immunogenic apoptotic bodies from infected cells may be obtained for example with anthracyclines including doxorubicin, daunorubicin, idarubicin and mitoxanthrone; oxaliplatin, UVC, UVB or γ-radiation treated infected cells releasing apoptotic bodies.

Examples of tissue lysate include, but are not limited to, lymph nodes, synovial liquid or inflammatory tissue lysate.

In one embodiment, the pathogen-specific antigen described herein is an antigen from HIV or SIV origin.

In one embodiment, the immunogenic bodies are obtained from HIV infected $CD4^+$ T cells.

In one embodiment, the pathogen-specific antigen described herein is an antigen from HIV origin.

In one embodiment, the pathogen-specific antigen described herein is an HIV antigen.

Due to the great variability in the HIV genome, which results from mutation, recombination, insertion and/or deletion, HIV has been classified in groups, subgroups, types, subtypes and genotypes. There are two major HIV groups (HIV-1 and HIV-2) and many subgroups because the HIV genome mutates constantly. The major difference between the groups and subgroups is associated with the viral envelope. HIV-1 is classified into a main group (M), said group M being divided into least nine genetically distinct subtypes. These are subtypes A, B, C, D, F, G, H, J and K. Many other subtypes resulting from in vivo recombination of the previous ones also exist (e.g., CRF).

In one embodiment, the HIV antigen is related to a specific HIV group, subgroup, type, subtype or to a combination of several subtypes.

In one embodiment, the HIV virus is HIV-1 or HIV-2, preferably, HIV-1. In another embodiment, the HIV-1 virus is from group M and subtype B (HXB2).

In one embodiment, the HIV antigen is an inactivated whole HIV virus.

As used herein, "inactivated whole HIV" means a complete HIV particle, which has been inactivated, and which is no more infectious.

In one embodiment, the HIV antigen is an autologous HIV antigen. In another embodiment, the HIV antigen is not an autologous HIV antigen. In one embodiment, the HIV antigen is made of inactivated autologous HIV virus.

As used herein, "an antigen made of inactivated autologous HIV virus" refers to an antigen comprising or consisting of the HIV virus infecting the human to be treated and appropriately inactivated for a safe therapeutic administration to humans. Thus, in practice, to prepare the vaccine composition of the invention, the HIV virus is isolated from the human to be treated, more particularly from the $CD4^+$ T cells of said human. The thus isolated HIV virus is cultured and inactivated.

In one embodiment, the HIV antigen is selected from the group consisting of a HIV gag, a HIV env, a HIV rev, a HIV tat, a HIV nef, a HIV pol, and a HIV vif.

In one embodiment, the HIV antigen comprises one or more epitopes of a HIV gag, a HIV env, a HIV rev, a HIV tat, a HIV nef, a HIV pol, and a HIV vif proteins.

In one embodiment, the HIV antigen comprises at least a HIV gag and/or HIV pol protein. Alternatively or additionally, said antigen derived from a HIV virus may comprise one or more proteins encoded by gag such as the capsid protein (p24) and the matrix protein (p1), and/or one or more proteins encoded by pol such as the integrase, the reverse transcriptase and the protease.

In one embodiment, the pathogen-specific antigen described herein is a MHCIb/E-binding antigen. In one embodiment, the pathogen-specific antigen is a MHCIb/E-binding peptide.

In one embodiment, the pathogen-specific antigen described herein is an HIV or SIV-derived MHCIb/E-binding peptide. In one embodiment, the pathogen-specific antigen is an HIV or SIV-derived MHCIb/E-binding antigen.

In one embodiment, the HIV-derived MHCIb/E-binding antigen described herein is selected from the group of SEQ ID NO: 1 to SEQ ID NO: 4. In one embodiment, the HIV-derived MHCIb/E-binding peptide is selected from the group of SEQ ID NO: 1 to SEQ ID NO: 4.

In one embodiment, the HIV-derived MHCIb/E-binding antigen has the amino acid sequence RMYSPVSIL (SEQ ID NO: 1). In one embodiment, the HIV-derived MHCIb/E-binding antigen has the amino acid sequence PEIVIYDYM (SEQ ID NO: 2). In one embodiment, the HIV-derived MHCIb/E-binding antigen has the amino acid sequence TALSEGATP (SEQ ID NO: 3). In one embodiment, the HIV-derived MHCIb/E-binding antigen has the amino acid sequence RIRTWKSLV (SEQ ID NO: 4).

As used herein, the term "alpha interferon" (IFN-α) or "interferon-alpha" refers to a family of more than 20 related but distinct members encoded by a cluster on chromosome 9 and all bind to the same IFN receptor. Among these, the IFN-α2 have 3 recombinant variants (α2a, α2b, α2c) depending upon the cells of origin and the IFN-α2b is the predominant variant in human genome. There is evidence though that each subtype has a different binding capacity to the IFNAR, modulating the signaling transduction events and the biological effects in the target cells.

In one embodiment, the interferon-alpha blocking agent described herein is an agent neutralizing circulating IFN-α and/or an agent blocking IFN-α signaling, and/or an agent depleting IFN-α producing cells, and/or an agent blocking IFN-α production.

In one embodiment, the interferon-alpha blocking agent described herein comprises at least one agent selected from: an agent neutralizing circulating IFN-α and/or an agent blocking IFN-α signaling, and/or an agent depleting IFN-α producing cells, and/or an agent blocking IFN-α production.

In one embodiment, the agent neutralizing circulating IFN-α and/or the agent blocking IFN-α signaling, and/or the agent depleting IFN-α producing cells, and/or the agent blocking IFN-α production is/are an IFN-α antagonist.

In some embodiments, wherein the interferon-alpha blocking agent is selected from the group consisting of: an agent neutralizing circulating alpha interferon, an agent blocking interferon-alpha signaling, an agent depleting IFN-α producing cells, and/or an agent blocking IFN-α production, wherein the agent neutralizing circulating alpha interferon is selected from the group comprising active anti-IFN-α vaccine including antiferon or passive anti-IFN-α vaccine including anti-IFN-α antibodies or anti-IFN-α hyper-immune serum, wherein the blocking agent of interferon-alpha signaling is selected from the group of anti-type I interferon R1 or R2 antibodies or from interferon-alpha endogenous regulators including SOSC1 or aryl hydrocarbon receptors, wherein the agent depleting IFN-α producing cells is an agent depleting plasmacytoid dendritic cells (pDCs), and wherein the agent blocking IFN-α production is an agent blocking the production of IFN-α by pDCs.

In some embodiments, the interferon-alpha blocking agent is an agent neutralizing circulating alpha interferon selected from the group consisting of active anti-IFN-α vaccine including antiferon or passive anti-IFN-α vaccine including anti-IFN-α antibodies or anti-IFN-α hyper-immune serum, and wherein the blocking agent of interferon-alpha signaling is selected from the group consisting of anti-type I interferon R1 or R2 antibodies, SOSC1 and aryl hydrocarbon receptors.

As used herein, the term "alpha interferon antagonist" refers to a substance which interferes with or inhibits the IFN-α biological activity. "IFN-α biological activity" as used herein refers to any activity occurring as a result of IFN-α binding to its receptor IFNAR (IFNAR1/IFNAR2 heterodimer). Such binding can, for example, activate the JAK-STAT signaling cascade, and trigger tyrosine phosphorylation of a number of proteins including JAKs, TYK2, STAT proteins. Thus, the signaling blocking agent of interferon can neutralize the fixation of the INF-α to its receptor and/or block the signaling cascade induced by the binding of IFN-α to its receptor. In some embodiments, the IFN-α antagonist is selected from the group of active anti-IFN-α vaccine (e.g., antiferon) or passive anti-IFN-α vaccine (e.g., anti-IFN-α antibody or anti-IFN-α hyper-immune serum). See for example Noel et al. (2018). Cytokine Growth Factor Rev 40:99-112.

In one embodiment, the agent neutralizing circulating IFN-α described herein is an IFN-α ligand inhibitor.

In one embodiment, the agent neutralizing circulating IFN-α is an anti-IFN-α antibody. Examples of anti-IFN-α antibodies include, without limitation, Sifalimumab, Rontalizumab, MMHA-1 clone, MMHA-2 clone, MMHA-6 clone, MMHA-8 clone, MMHA-9 clone, MMHA-11 clone, MMHA-13 clone and MMHA-17 clone.

In one embodiment, the agent neutralizing circulating IFN-α is an anti-IFN-α hyper-immune serum.

In one embodiment, the agent neutralizing circulating IFN-α described herein is an antiferon, such as, for example, an IFN-α-Kinoid.

In one embodiment, the agent neutralizing circulating IFN-α is a soluble receptor that binds IFN-α.

In one embodiment, the agent neutralizing circulating IFN-α does not neutralize circulating type III interferon.

In one embodiment, the agent blocking IFN-α signaling described herein is an IFNAR antagonist.

In one embodiment, the agent blocking IFN-α signaling is an IFNAR1 antagonist. In another embodiment, the agent blocking IFN-α signaling is an IFNAR2 antagonist.

In one embodiment, the agent blocking IFN-α signaling is an antibody that binds to IFNAR1 or IFNAR2.

In one embodiment, the agent blocking IFN-α signaling is an agent that antagonizes the type I IFN signaling pathway.

In one embodiment, the agent blocking the agent blocking IFN-α signaling can be an inhibitor of type I IFN signaling pathway. Type I IFN signaling pathway inhibitors are well known in the art and include, without limitation, JAK1/2 inhibitors and STAT inhibitors. Accordingly, in one embodiment, the agent blocking IFN-α signaling is selected from JAK1/2 inhibitors and STAT inhibitors. Non-limiting examples of JAK1/2 inhibitor comprise Ruxolitinib, Tofacitinib and Baricitinib.

In one embodiment, the agent blocking IFN-α signaling can be an endogenous negative regulator of type I IFN signaling pathway. Endogenous negative regulators are well known in the art and include, without limitation, SOCS1/3, FOXO3, Aryl hydrocarbon Receptor (AhR) or other negative regulators. Accordingly, in one embodiment, the agent blocking interferon signaling is selected from SOCS1/3, FOXO3 or Aryl hydrocarbon Receptor (AhR).

In one embodiment, the agent blocking IFN-α signaling is a PASylated antagonist. PASylated antagonist of type I IFN are known in the art, see for example Nganou-Makamdop et al. (2018). PLoS Pathog 14(8): e1007246.

In one embodiment, the IFN-α antagonist described herein is an agent depleting IFN-α producing cells.

As used herein, the term "IFN-α producing cells" refers to any cell that produce IFN-α. In particular, it is well known in the art that the plasmacytoid dendritic cells (pDCs) are the main producer of IFN-α. Thus, in one embodiment, the agent depleting IFN-α producing cells depletes pDCs.

In one embodiment, the agent depleting IFN-α producing cells is an antibody. In one embodiment, the antibody depletes pDCs, such as, for example, an anti-CD123 antibody (i.e., anti-IL-3RA).

In one embodiment, the IFN-α antagonist described herein is an agent that blocks the production of IFN-α.

In one embodiment, the agent that blocks the production of the IFN-α is an antibody. In one embodiment, the antibody blocks the production of IFN-α by pDCs. Said antibody can be, for example, an anti-BDCA2 (Blood DC Antigen 2) antibody.

In one embodiment, the agent blocking interferon signaling does not block type III interferon signaling.

In some embodiments, the interferon-alpha blocking agent selected from the group consisting of:
- an anti-IFN-α antibody, preferably Sifalimumab, Rontalizumab, MMHA-1 clone, MMHA-2 clone, MMHA-6 clone, MMHA-8 clone, MMHA-9 clone, MMHA-11 clone, MMHA-13 clone or MMHA-17 clone,
- an anti-IFN-α hyper-immune serum,
- an antiferon, preferably an IFN-α-Kinoid,
- a soluble receptor that binds IFN-α,
- an IFNAR1 or IFNAR2 antagonist, preferably an antibody that binds to IFNAR1 or IFNAR2,
- a type I IFN signaling pathway inhibitors selected from a STAT inhibitor and a JAK1/2 inhibitor, such as e.g. Ruxolitinib, Tofacitinib or Baricitinib,
- an endogenous negative regulator of type I IFN signaling pathway selected from SOCS1/3, FOXO3, Aryl hydrocarbon Receptor (AhR) or another negative regulator,
- a PASylated antagonist,
- an antibody depleting pDCs, preferably an anti-CD123 (i.e. anti-IL-3RA) antibody,
- an antibody blocking the production of IFN-α by pDCs, preferably an anti-BDCA2 (Blood DC Antigen 2) antibody.

As used herein, the term "type III interferon", also called interferon-lambda (IFN-λ), refers to naturally occurring and/or recombinant cytokines of the type III interferon-lambda family. There are four IFN-λ members in humans, IFN-λ1/IL-29, IFN-λ2/IL-28A, IFN-λ3/IL-28B, IFN-λ4.

In one embodiment, the type III interferon is IFN-λ.

In one embodiment, the IFN-λ comprises at least one IFN-λ subtype (e.g., IFN-λ1, IFN-λ2 IFN-λ3, IFN-λ4).

In one embodiment, the IFN-λ is selected from the group of IFN-λ1, IFN-λ2 IFN-λ3, IFN-λ4 or a combination thereof.

In one embodiment, the human IFN-λ1 has the following accession number NP_742152.1. In one embodiment, the human IFN-λ2 has the following accession number NP_742150.1. In one embodiment, the human IFN-λ3 has the following accession numbers NP_001333866.1 (isoform 1) or NP_742151.2 (isoform 2). In one embodiment, the human IFN-λ4 has the following accession number NP_001263183.2.

In one embodiment, the interferon-lambda is IFN-λ1. In one embodiment, the interferon-lambda is IFN-λ2. In one embodiment, the interferon-lambda is IFN-λ3. In one embodiment, the interferon-lambda is IFN-λ4.

In one embodiment, the interferon-lambda is chemically modified to improve certain properties such as serum half-life. In one embodiment the interferon-lambda of the invention is pegylated (i.e., the interferon-lambda is covalently attached to poly(ethyleneglycol), and the like). Methods for producing pegylated proteins are well known in the art, see for example Chapman A et al., 2002, Advanced Drug Delivery Reviews 54: 531-545.

In one embodiment, the interferon-lambda is a functional mimetic of IFN-λ1. In one embodiment, the interferon-lambda is a functional mimetic of IFN-λ2. In one embodiment, the interferon-lambda is a functional mimetic of IFN-λ3. In one embodiment, the interferon-lambda is a functional mimetic of IFN-λ4.

As used herein, the term "functional mimetic" means a molecule which has the same or similar biological effects as the naturally occurring protein. For example an interferon-lambda functional mimetic may activate the interferon-lambda receptor and drive the transcription of IFN-stimulated genes.

In one embodiment, the interferon-lambda functional mimetic is a fragment of IFN-λ1.

In one embodiment, the interferon-lambda functional mimetic is a fragment of IFN-λ2.

In one embodiment, the interferon-lambda functional mimetic is a fragment of IFN-λ3.

In one embodiment, the interferon-lambda functional mimetic is a fragment of IFN-λ4.

In one embodiment, the interferon-lambda functional mimetic is an antibody. Such interferon-lambda functional mimetic antibody can elicit the same or similar biological effects as the naturally occurring protein. For example the antibody may bind to an epitope on the interferon-lambda receptor, activating receptor signaling and driving the transcription of IFN-stimulated genes. The heterodimeric receptor complex of interferon-lambda (IFNLR) comprises IFNLR1 (IFNLRA, IL-28RA), and IL10R2 (IL-10RB). IFNLR1 confers ligand specificity and enables receptor assembly, while IL10R2 is shared with IL-10 family members and is required for signaling.

In one embodiment, the interferon-lambda derivative is a small molecule chemical entity (such as, for example, a chemical entity with a molecular weight less than 900 Daltons). Methods of screening chemical libraries to identify small molecule chemical entities which may be potential drug candidates are known in the art. For example, a chemical library may be tested in a ligand-receptor binding assay.

In one embodiment, the agent stimulating the production of type III interferon is an agent that stimulates pattern-recognition receptors (PRRs).

In one embodiment, the agent stimulating the production of type III interferon is an agent that stimulates pattern-recognition receptors (PRRs).

"Pattern-recognition receptor" includes mainly Toll-like receptors (TLRs), NOD-like receptors (NLRs), RIG-1-like receptors (RLRs), and C-type lectin receptors (CLRs). They recognize different microbial signatures or host-derived danger signals and trigger an immune response, such as interferon production.

In one embodiment, the agent stimulating the production of type III interferon comprises toll-like receptor (TLR) ligands (e.g., TLR3, TLR5, TLR7/8 and TLR9), RIG-I ligands and MDA-5 ligands.

In one embodiment, the agent stimulating the production of type III interferon comprises poly I:C, CpG and/or Tat protein.

In one embodiment, the agent stimulating the production of type III interferon can also induces production of type I interferon.

The present invention further relates to a combination comprising:
1) a first part comprising CD8 vaccine specific for at least one infectious disease-related antigen as described herein,
2) optionally a second part comprising an interferon-alpha blocking agent as described herein, and
3) a third part comprising a type III interferon and/or an agent stimulating the production of type III interferon as described herein.

The present invention also relates to a kit-of-parts comprising at least 2 parts:
1) a first part comprising CD8 vaccine specific for at least one infectious disease-related antigen as described herein,
2) optionally a second part comprising an interferon-alpha blocking agent as described herein, and
3) a third part comprising a type III interferon and/or an agent stimulating the production of type III interferon as described herein.

In one embodiment, the CD8 vaccine specific for at least one infectious disease-related antigen is comprised in a composition.

In one embodiment, said composition consists essentially of the CD8 vaccine specific for at least one infectious disease-related antigen.

As used herein, "consisting essentially of", with reference to a composition, means that the CD8 vaccine is the only one therapeutic agent or agent with a biologic activity within said composition.

In one embodiment, said composition is a pharmaceutical composition and further comprises at least one pharmaceutically acceptable excipient.

As used herein, the term "excipient" refers to any and all conventional solvents, dispersion media, fillers, solid carriers, aqueous solutions, coatings, antibacterial and antifungal agents, isotonic and absorption delaying agents and the like. In general, the nature of the excipient will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. For human administration, preparations should meet sterility, pyrogenicity, general safety and purity standards as required by regulatory offices, such as, for example, FDA Office or EMA. In one embodiment, the excipient is an adjuvant, a stabilizer, an emulsifier, a thickener, a preservative, an antibiotic, an organic or inorganic acid or its salt, a sugar, an alcohol, an antioxidant, a diluent, a solvent, a filler, a binder, a sorbent, a buffering agent, a chelating agent, a lubricant, a coloring agent, or any other component By "pharmaceutically acceptable" is meant that the ingredients of a pharmaceutical composition are compatible with each other and not deleterious to the subject to which it is administered. Examples of pharmaceutically acceptable excipient include, but are not limited to, water, saline, phosphate buffered saline, dextrose, glycerol, ethanol and the like or combinations thereof.

Pharmaceutically acceptable excipients that may be used in the pharmaceutical combination of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

In one embodiment, said composition is a vaccine composition. In one embodiment, said vaccine composition further comprises at least one adjuvant.

In one embodiment, the CD8 vaccine specific for at least one infectious disease-related antigen is comprised in a medicament.

In one embodiment, when CD8 vaccine according to the invention comprises an infectious disease-related antigen and a non-pathogenic bacterium, the infectious disease-related antigen and the non-pathogenic bacterium are two separate and distinct components that are contained as a mixture into a pharmaceutical composition. In another embodiment, when CD8 vaccine according to the invention comprises an infectious disease-related antigen and a non-pathogenic bacterium, the infectious disease-related antigen and the non-pathogenic bacterium, are the same component that are contained into a pharmaceutical composition.

In one embodiment, the CD8 vaccine is a composition, a pharmaceutical composition or a medicament, wherein the CD8 vaccine is conjugated to a delivery vehicle.

In one embodiment, the CD8 vaccine comprises at least one infectious disease-related antigen and a non-pathogenic bacterium, wherein the at least one infectious disease-related antigen and/or the non-pathogenic bacterium is/are conjugated to a delivery vehicle. In one embodiment, the at least one infectious disease-related antigen is conjugated to a delivery vehicle. In one embodiment, the non-pathogenic bacterium is conjugated to a delivery vehicle. In one embodiment, the at least one infectious disease-related antigen and non-pathogenic bacterium are conjugated to a delivery vehicle.

By the term "conjugated" is meant that the infectious disease-related antigen and/or non-pathogenic bacterium is/are physically or chemically coupled, adhered, absorbed or encapsuled to a delivery vehicle. Examples of conjugation include, without limitation, covalent linkage and electrostatic complexation. The terms "complexed," "complexed with," and "conjugated" are used interchangeably herein. In one embodiment, more than one copy or type of infectious disease-related antigen is conjugated to a delivery vehicle. In one embodiment, more than one copy or type of non-pathogenic bacterium is conjugated to a delivery vehicle.

Delivery vehicles are well known in the art. For example, the delivery vehicle can be chosen from a cationic lipid, a liposome, a cochleate, a virosome, an immune-stimulating complex (ISCOM®), a microparticle, a microsphere, a nanosphere, a unilamellar vesicle (LUV), a multilamellar vesicle, an emulsome, and a polycationic peptide, a lipoplexe, a polyplexe, a lipopolyplexe, a water-in-oil (W/O) emulsion, an oil-in-water (O/W) emulsion, a water-in-oil-in water (W/O/W) multiple emulsion, a micro-emulsion, a nano-emulsion, a micelle, a dendrimer, a virosome, a virus-like particle, a polymeric nanoparticle (such as a nanobead, a nanosphere or a nanocapsule), a polymeric microparticle (such as a microsphere or a microcapsule), a chitosan, a poly(lactic acid) (PLA) polymer, a poly(lactic-co-glycolide) (PLGA) polymer, a cyclodextrin, a niosome, or an ISCOM® and, optionally, a pharmaceutically acceptable carrier. In one embodiment, the delivery vehicle is in an adapted form for an oral administration, an injection, a topical administration or a rectal administration.

In one embodiment, the CD8 vaccine is conjugated to a nanoparticle, such as e.g. a nanobead, a nanosphere or a nanocapsule. Preferably, the nanoparticle has a diameter of between 50 and 300 nm, more preferably of between 70 and 200 nm, even more preferably of between 100 and 150 nm.

Microfold cells (or M cells) are found in the gut-associated lymphoid tissue (GALT) of the Peyer's patches in the small intestine, and in the mucosa-associated lymphoid tissue (MALT) of other parts of the gastrointestinal tract. These cells are known to initiate mucosal immunity responses.

In some embodiments, the delivery vehicle is coated with, or conjugated to, molecules, such as e.g. lectins or peptides, that enhance delivery to M cells.

M cells express a specific carbohydrate moiety (α-L-fucose) on the apical surface. Lectin subtypes, such as Ulex europaeus agglutinin 1 (UEA-1) and Aleuria aurantia, have shown their high specificity for α-L-fucose on M cells. Thus, in some embodiments, the delivery vehicle is coated with, or conjugated to, at least one lectin chosen from Ulex europaeus agglutinin 1 (UEA-1) and Aleuria aurantia.

M cells also express claudin 4 and TM4SF3. Delivery system using surface-conjugated peptides having high affinity to claudin 4, such as e.g. CTGKSC (SEQ ID NO: 11), LRVG (SEQ ID NO: 12), or CKSTHPLSC (CKS9) (SEQ ID NO: 13), may also be used. Thus, in some embodiments, the delivery vehicle is coated with, or conjugated to, at least one peptide chosen from CTGKSC (SEQ ID NO: 11), LRVG (SEQ ID NO: 12), and CKSTHPLSC (CKS9) (SEQ ID NO: 13).

In one embodiment, the interferon-alpha blocking agent is comprised in a composition. In one embodiment, said composition comprises at least one interferon-alpha blocking agent selected among: an agent neutralizing circulating alpha interferon, and/or an agent blocking interferon-alpha signaling, and/or an agent depleting IFN-α producing cells, and/or an agent blocking IFN-α production.

In one embodiment, said composition consists essentially of the agent neutralizing circulating alpha interferon. In one embodiment, said composition consists essentially of the agent blocking IFN-α signaling. In one embodiment, said composition consists essentially of the agent depleting IFN-α producing cells. In one embodiment, said composition consists essentially of the agent blocking IFN-α production.

In one embodiment, said composition is a pharmaceutical composition and further comprises at least one pharmaceutically acceptable excipient.

In one embodiment, the interferon-alpha blocking agent is comprised in a medicament.

In one embodiment, said medicament comprises at least one interferon-alpha blocking agent selected among: an agent neutralizing circulating alpha interferon, and/or an agent blocking interferon-alpha signaling, and/or an agent depleting IFN-α producing cells, and/or an agent blocking IFN-α production.

In one embodiment, the agent neutralizing circulating alpha interferon is comprised in a medicament. In one embodiment, the agent blocking interferon-alpha signaling is comprised in a medicament. In one embodiment, the agent depleting IFN-α producing cells is comprised in a medicament. In one embodiment, the agent blocking IFN-α production is comprised in a medicament.

In one embodiment, the type III interferon and/or the agent stimulating the production of type III interferon is/are comprised in a composition.

In one embodiment, said composition consists essentially of the type III interferon. In one embodiment, said composition consists essentially of the agent stimulating the production of type III interferon. In one embodiment, said composition consists essentially of the type III interferon and the agent stimulating the production of type III interferon.

In one embodiment, said composition is a pharmaceutical composition and further comprises at least one pharmaceutically acceptable excipient.

In one embodiment, the type III interferon and/or the agent stimulating the production of type III interferon is/are comprised in a medicament.

In one embodiment, the type III interferon is comprised in a medicament. In one embodiment, the agent stimulating the production of type III interferon is comprised in a medicament. In one embodiment, the type III interferon and the agent stimulating the production of type III interferon are comprised in a medicament.

Another object of the invention is a pharmaceutical composition comprising a combination of 1) a CD8 vaccine specific for at least one infectious disease-related antigen as described hereinabove, 2) optionally an interferon-alpha blocking agent, and 3) a type III interferon and/or an agent stimulating the production of type III interferon, and further comprises at least one pharmaceutically acceptable excipient, or a kit-of-parts as described hereinabove, for use in the treatment of an infectious diseases in a subject in need thereof.

Another object of the invention is a medicament comprising a combination of 1) a CD8 vaccine specific for at least one infectious disease-related antigen as described hereinabove, 2) optionally an interferon-alpha blocking agent, and 3) a type III interferon and/or an agent stimulating the production of type III interferon, or a pharmaceutical combination as described hereinabove, or a kit-of parts as described hereinabove, for use in the treatment of an infectious diseases in a subject in need thereof.

As mentioned hereinabove, the combination, pharmaceutical combination, medicament or kit-of-parts according to the invention of the invention are to be administered either simultaneously, separately or sequentially with respect to each other.

In one embodiment, according to the present invention, 1) the CD8 vaccine specific for at least one infectious disease-related antigen, 2) the interferon-alpha blocking agent, and/ or 3) the type III interferon and/or an agent stimulating the production of type III interferon in a combination of the invention are to be administered either simultaneously, separately or sequentially with respect to each other.

According to one embodiment, 1) the CD8 vaccine specific for at least one infectious disease-related antigen, 2) interferon-alpha blocking agent, and/or 3) the type III interferon and/or an agent stimulating the production of type III interferon, the combination or pharmaceutical combination thereof, medicament or kit-of-parts according to the invention will be formulated for administration to the subject.

In one embodiment, 1) the CD8 vaccine specific for at least one infectious disease-related antigen, 2) interferon-alpha blocking agent, and/or 3) the type III interferon and/or an agent stimulating the production of type III interferon, the combination or pharmaceutical combination thereof, or medicament according to the invention may be administered orally, intragastrically, parenterally, topically, by inhalation spray, rectally, nasally, buccally, preputiallly, vaginally or via an implanted reservoir.

In one embodiment, the oral administration comprises mucosal administration. A "mucosal administration" is a delivery to a mucosal surface, such as sub-lingual, tracheal, bronchial, pharyngeal, esophageal, gastric, and mucosae of the duodenum, small and large intestines, including the rectum mucosae. Yet preferably, the mucosal surface refers to digestive mucosa.

In one embodiment, the administration of each part of the combination, pharmaceutical combination, medicament or kit-of-parts according to the invention can be done by the same route of administration or by a different route of administration.

In one embodiment, the combination, pharmaceutical combination, medicament or kit-of-parts according to the invention is in an adapted form for an oral or an intragastric administration. Thus, in one embodiment, the combination, pharmaceutical combination, medicament or kit-of-parts according to the invention is to be administered orally or intragastrically to the subject, for example as a powder, a tablet, a capsule, and the like or as a tablet formulated for extended or sustained release.

Examples of forms adapted for oral or intragastric administration include, without being limited to, liquid, paste or solid compositions, and more particularly tablets, tablets formulated for extended or sustained release, capsules, pills, dragees, liquids, gels, syrups, slurries, suspensions, and the like.

In one embodiment, the CD8 vaccine specific for at least one infectious disease-related antigen as described hereinabove is in an adapted form for an oral or intragastric administration. Thus, in one embodiment, the CD8 vaccine specific for at least one infectious disease-related antigen as described hereinabove is to be administered orally or intragastrically to the subject, for example as a capsule or as a tablet.

In another embodiment, the interferon-alpha blocking agent as described hereinabove is in an adapted form for an oral or intragastric administration. Thus, in one embodiment, the interferon-alpha blocking agent interferon-alpha as described hereinabove is to be administered orally or intragastrically to the subject, for example as a capsule or as a tablet.

In another embodiment, the type III interferon and/or the agent stimulating the production of type III interferon as described hereinabove is/are in an adapted form for an oral or intragastric administration. Thus, in one embodiment, the type III interferon and/or the agent stimulating the production of type III interferon as described hereinabove is/are to be administered orally or intragastrically to the subject, for example as a capsule or as a tablet.

In one embodiment, the combination, pharmaceutical combination, medicament or kit-of-parts according to the invention is in a form adapted for parenteral administration.

In another embodiment, the combination, pharmaceutical combination, medicament or kit-of-parts according to the invention is in an adapted form for an injection such as, for example, for intravenous, subcutaneous, intramuscular, intraperitoneal intradermal, transdermal injection or infusion. Thus, the combination, pharmaceutical combination, medicament or kit-of-parts according to the invention is to be injected to the subject, by intravenous, intramuscular, intraperitoneal, intrapleural, subcutaneous, transdermal injection or infusion.

In another embodiment, the combination, pharmaceutical combination, medicament or kit-of-parts according to the invention is in an adapted form for an injection such as, for example, for intravenous, intramuscular, intraperitoneal injection or infusion. Thus, the combination, pharmaceutical combination, medicament or kit-of-parts according to the invention is to be injected to the subject, by intravenous, intramuscular, intraperitoneal, injection or infusion.

Sterile injectable forms of the combination, the pharmaceutical combination, medicament or kit-of-parts according to the invention may be a solution or an aqueous or oleaginous suspension. These suspensions may be formulated according to techniques known in the art using suitable dispersing or wetting agents and suspending agents. The sterile injectable preparation may also be a sterile injectable solution or suspension in a non-toxic pharmaceutically acceptable diluent or solvent. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In one embodiment, the CD8 vaccine specific for at least one infectious disease-related antigen as described hereinabove is in an adapted form for a parenteral administration and/or injection. Thus, in another embodiment, the CD8 vaccine specific for at least one infectious disease-related antigen as described hereinabove is to be administered parenterally and/or injected to the subject, by intravenous, intramuscular, intraperitoneal, intrapleural, subcutaneous, transdermal injection or infusion, preferably by intravenous injection.

In another embodiment, the interferon-alpha blocking agent as described hereinabove is in an adapted form for a parenteral administration and/or injection. Thus, in another embodiment, the interferon-alpha blocking agent as described hereinabove is to be administered parenterally and/or injected to the subject, by intravenous, intramuscular, intraperitoneal, intrapleural, subcutaneous, transdermal injection or infusion, preferably by intravenous injection.

In another embodiment, the type III interferon and/or the agent stimulating the production of type III interferon as described hereinabove is/are in an adapted form for a parenteral administration and/or injection. Thus, in another embodiment, the type III interferon and/or the agent stimulating the production of type III interferon as described hereinabove is/are to be administered parenterally and/or injected to the subject, by intravenous, intramuscular, intraperitoneal, intrapleural, subcutaneous, transdermal injection or infusion, preferably by intravenous injection In another embodiment, the combination, pharmaceutical combination, medicament or kit-of-parts according to the invention is in a form adapted for topical administration. Thus, the combination, pharmaceutical combination, medicament or kit-of-parts according to the invention is to be administered topically.

Examples of forms adapted for topical administration include, without being limited to, liquid, paste or solid compositions, and more particularly aqueous solutions, drops, dispersions, sprays, microcapsules, micro- or nanoparticles, polymeric patch, or controlled-release patch, and the like.

In another embodiment, the CD8 vaccine specific for at least one infectious disease-related antigen as described hereinabove is in a form adapted for topical administration. Thus, the CD8 vaccine specific for at least one infectious disease-related antigen as described hereinabove according to the invention is to be administered topically.

In another embodiment, the interferon-alpha blocking agent as described hereinabove is in a form adapted for topical administration. Thus, the agent interferon-alpha blocking agent as described hereinabove is to be administered topically.

In another embodiment, the type III interferon and/or the agent stimulating the production of type III interferon as described hereinabove is/are in a form adapted for topical administration. Thus, the CD8 vaccine specific for at least one infectious disease-related antigen as described hereinabove according to the invention is to be administered topically.

In another embodiment, the combination, pharmaceutical combination, medicament or kit-of-parts according to the invention is in a form adapted for rectal administration. Thus, in one embodiment, the combination, pharmaceutical combination, medicament or kit-of-parts according to the invention is to be to be administered rectally.

Examples of forms adapted for rectal administration include, without being limited to, suppository, micro enemas, enemas, gel, rectal foam, cream, ointment, and the like.

In another embodiment, the CD8 vaccine specific for at least one infectious disease-related antigen as described hereinabove is in a form adapted for rectal administration. Thus, in one embodiment, the CD8 vaccine specific for at least one infectious disease-related antigen as described hereinabove is to be to be administered rectally.

In another embodiment, the interferon-alpha blocking agent as described hereinabove is in a form adapted for rectal administration. Thus, in one embodiment, the interferon-alpha blocking agent as described hereinabove is to be to be administered rectally.

In another embodiment, the type III interferon and/or the agent stimulating the production of type III interferon as described hereinabove is/are in a form adapted for rectal administration. Thus, in one embodiment, the type III interferon and/or the agent stimulating the production of type III interferon as described hereinabove is/are to be to be administered rectally.

In one embodiment, the combination, pharmaceutical combination, medicament or kit-of-parts according to the invention comprises 1) a CD8 vaccine specific for at least one infectious disease-related antigen, 2) optionally an interferon-alpha blocking agent, and 3) a type III interferon and/or an agent stimulating the production of type III interferon which are all in a form adapted for parenteral administration and/or injection.

In one embodiment, the combination, pharmaceutical combination, medicament or kit-of-parts according to the invention comprises 1) a CD8 vaccine specific for at least one infectious disease-related antigen, 2) optionally an interferon-alpha blocking agent, and 3) a type III interferon and/or an agent stimulating the production of type III interferon which are all in a form adapted for oral administration.

In another embodiment, the combination, pharmaceutical combination, medicament or kit-of-parts according to the invention comprises 1) a CD8 vaccine specific for at least one infectious disease-related antigen that is in a form adapted for oral administration, and 2) optionally an interferon-alpha blocking agent, and 3) a type III interferon and/or an agent stimulating the production of type III interferon that is/are in a form adapted for parenteral administration and/or injection.

In another embodiment, the combination, pharmaceutical combination, medicament or kit-of-parts according to the invention comprises 1) a CD8 vaccine specific for at least one infectious disease-related antigen that is in a form adapted for oral administration, and 2) optionally an interferon-alpha blocking agent, and 3) a type III interferon and/or an agent stimulating the production of type III interferon that is/are in a form adapted for parenteral administration and/or injection.

In another embodiment, the combination, pharmaceutical combination, medicament or kit-of-parts according to the invention comprises 1) a CD8 vaccine specific for at least one infectious disease-related antigen that is in a form adapted for rectal administration, and 2) optionally an interferon-alpha blocking agent, and 3) a type III interferon and/or an agent stimulating the production of type III interferon that is/are in a form adapted for parenteral administration and/or injection.

In another embodiment, the combination, pharmaceutical combination, medicament or kit-of-parts according to the invention comprises 1) a CD8 vaccine specific for at least one infectious disease-related antigen that is in a form adapted for vaginal administration, and 2) optionally an interferon-alpha blocking agent, and 3) a type III interferon and/or an agent stimulating the production of type III interferon that is/are in a form adapted for parenteral administration and/or injection.

As mentioned hereinabove, the administration of each part of the combination, pharmaceutical combination, medicament or kit-of-parts according to the invention can be done simultaneously, separately or sequentially.

In one embodiment, the combination, pharmaceutical combination, medicament or kit-of-parts according to the invention comprises a first part comprising a CD8 vaccine specific for at least one infectious disease-related antigen, optionally a second part comprising an interferon-alpha blocking agent, and a third part comprising a type III interferon and/or an agent stimulating the production of type III interferon which are all administered at the same time once, twice, three, four, five, six, seven, eight, nine, ten times or more.

In one embodiment of the invention, the first part of the combination, pharmaceutical combination or kits of parts is to be administered prior to the second part and the third part of the combination, pharmaceutical combination or kits of parts once, twice, three, four, five, six, seven, eight, nine, ten times or more.

In another embodiment of the invention, the second part of the combination, pharmaceutical combination or kits of parts is to be administered prior to the first part and the third part of the combination, pharmaceutical combination or kits of parts once, twice, three, four, five, six, seven, eight, nine, ten times or more.

In another embodiment of the invention, the third part of the combination, pharmaceutical combination or kits of parts is to be administered prior to the first part and the second part of the combination, pharmaceutical combination or kits of parts once, twice, three, four, five, six, seven, eight, nine, ten times or more.

In one embodiment of the invention, the first part and the second part of the combination, pharmaceutical combination or kits of parts are to be administered prior to the third part of the combination, pharmaceutical combination or kits of parts once, twice, three, four, five, six, seven, eight, nine, ten times or more.

In another embodiment of the invention, the first part and the third part of the combination, pharmaceutical combination or kits of parts is to be administered prior to the second part of the combination, pharmaceutical combination or kits of parts once, twice, three, four, five, six, seven, eight, nine, ten times or more.

In another embodiment of the invention, the second part and the third part of the combination, pharmaceutical combination or kits of parts is to be administered prior to the first part and the second part of the combination, pharmaceutical combination or kits of parts once, twice, three, four, five, six, seven, eight, nine, ten times or more.

In one embodiment of the invention, the first part and the second part of the combination, pharmaceutical combination or kits of parts are to be administered at the same time once, twice, three, four, five, six, seven, eight, nine, ten times or more.

In one embodiment of the invention, the first part and the third part of the combination, pharmaceutical combination or kits of parts are to be administered at the same time once, twice, three, four, five, six, seven, eight, nine, ten times or more.

In one embodiment of the invention, the second part and the third part of the combination, pharmaceutical combination or kits of parts are to be administered at the same time once, twice, three, four, five, six, seven, eight, nine, ten times or more.

In one embodiment of the invention, the first part of the combination, pharmaceutical combination or kits of parts is to be administered prior to the second part of the combination, pharmaceutical combination or kits of parts once, twice, three, four, five, six, seven, eight, nine, ten times or more, and the second part is to be administered prior to the third part of the combination, pharmaceutical combination or kits of parts once, twice, three times or more.

In another embodiment of the invention, the second part of the combination, pharmaceutical combination or kits of parts is to be administered prior to the first part of the combination, pharmaceutical combination or kits of parts once, twice, three, four, five, six, seven, eight, nine, ten times or more, and the first part is to be administered prior to the third part of the combination, pharmaceutical combination or kits of parts once, twice, three, four, five, six, seven, eight, nine, ten times or more.

In one embodiment of the invention, the second part of the combination, pharmaceutical combination or kits of parts is to be administered prior to the third part of the combination, pharmaceutical combination or kits of parts once, twice, three, four, five, six, seven, eight, nine, ten times or more, and the third part is to be administered prior to the first part of the combination, pharmaceutical combination or kits of parts once, twice, three, four, five, six, seven, eight, nine, ten times or more.

In one embodiment of the invention, the third part of the combination, pharmaceutical combination or kits of parts is to be administered prior to the first part of the combination, pharmaceutical combination or kits of parts once, twice, three times, four, five, six, seven, eight, nine, ten or more, and the first part is to be administered prior to the second part of the combination, pharmaceutical combination or kits of parts once, twice, three, four, five, six, seven, eight, nine, ten times or more.

In one embodiment of the invention, the third part of the combination, pharmaceutical combination or kits of parts is to be administered prior to the second part of the combination, pharmaceutical combination or kits of parts once, twice, three, four, five, six, seven, eight, nine, ten times or more, and the second part is to be administered prior to the first part of the combination, pharmaceutical combination or kits of parts once, twice, three, four, five, six, seven, eight, nine, ten times or more.

In another embodiment, the combination, pharmaceutical combination, medicament or kit-of-parts according to the invention comprises a first part comprising a CD8 vaccine specific for at least one infectious disease-related antigen, optionally a second part comprising an interferon-alpha blocking agent, and a third part comprising a type III interferon and/or an agent stimulating the production of type III interferon which are all administered at the same time once a day for 1, 2, 3, 4, 5, 6, 7, 8, 9, 10 or more days.

In one embodiment, the combination, pharmaceutical combination, medicament or kit-of-parts according to the invention comprises a first part comprising a CD8 vaccine specific for at least one infectious disease-related antigen, optionally a second part comprising an interferon-alpha blocking agent, and a third part comprising a type III interferon and/or an agent stimulating the production of type III interferon which are all administered at the same time once a month for 1, 2, 3, 4, 5, 6, 7, 8, 9, 10 or more months.

In one embodiment, the combination, pharmaceutical combination, medicament or kit-of-parts according to the invention comprises a first part comprising a CD8 vaccine specific for at least one infectious disease-related antigen, optionally a second part comprising an interferon-alpha blocking agent, and/or a third part comprising a type III interferon and an agent stimulating the production of type III interferon which are all administered at the same time once a year for 1, 2, 3, 4, 5, 6, 7, 8, 9, 10 or more years.

In one embodiment, the administration of each part of the combination, pharmaceutical combination, medicament or kit-of-parts according to the invention can be done at the same time or at different time.

Another object of the invention is a method for preventing or treating an infectious disease in a subject comprising administering to the subject in need thereof a therapeutically effective amount of:

1) a CD8 vaccine specific for at least one infectious disease-related antigen,
2) optionally an interferon-alpha blocking agent, and
3) a type III interferon and/or an agent stimulating the production of type III interferon.

According to one embodiment, a therapeutically effective dose of the first part of the combination, pharmaceutical combination, medicament or kit-of-parts a as described hereinabove is to be administered in combination with a therapeutically effective dose of the second part of the combination, pharmaceutical combination, medicament or kit-of-parts as described hereinabove and a therapeutically effective dose of the third part of the combination, pharmaceutical combination, medicament or kit-of-parts as described hereinabove for use in the treatment of an infectious disease in a subject in need thereof. Thus, in one embodiment, the combination, pharmaceutical combination, medicament or kit-of-parts according to the invention comprises a therapeutically effective dose of first part as described hereinabove and a therapeutically effective dose of second part as described hereinabove and a therapeutically effective dose of third part as described hereinabove described hereinabove.

According to one embodiment, a therapeutically effective dose of the first part of the combination, pharmaceutical combination, medicament or kit-of-parts a as described hereinabove is to be administered in combination with a therapeutically effective dose of the second part of the combination, pharmaceutical combination, medicament or kit-of-parts as described hereinabove for use in the treatment of an infectious disease in a subject in need thereof. Thus, in one embodiment, the combination, pharmaceutical combination, medicament or kit-of-parts according to the invention comprises a therapeutically effective dose of first part as described hereinabove and a therapeutically effective dose of second part as described hereinabove.

According to one embodiment, a therapeutically effective dose of the first part of the combination, pharmaceutical combination, medicament or kit-of-parts a as described hereinabove is to be administered in combination with a therapeutically effective dose of the third part of the combination, pharmaceutical combination, medicament or kit-of-parts as described hereinabove for use in the treatment of an infectious disease in a subject in need thereof. Thus, in one embodiment, the combination, pharmaceutical combination, medicament or kit-of-parts according to the invention comprises a therapeutically effective dose of the first part as described hereinabove and a therapeutically effective dose of third part as described hereinabove.

In one embodiment, the administration of each part of the combination, pharmaceutical combination, medicament or kit-of-parts according to the invention can be done according to a prime/boost mode. Thus, the present invention also includes a variety of prime-boost regimens.

In one embodiment, the prime/boost mode comprises the steps of administrating:

one or more priming immunizations, wherein said boosting immunizations comprises: a therapeutically effective dose of the first part, a therapeutically effective dose of the second part, and/or a therapeutically effective dose of the third part, and one or more boosting immunizations.

In prime/boost regimens, the composition of each part of the combination, according to the invention may be the same or different for each immunization and the type of composition, the route, and formulation of each part of the combination pharmaceutical combination, medicament or kit-of-parts according to the invention may also be varied. For example, if an expression vector is used for the priming and boosting steps, it may either be of the same or different type (e.g., DNA or bacterial or viral expression vector). For example, one useful prime-boost regimen provides for at least two priming immunizations, two weeks apart, followed by at least one boosting immunizations (e.g., at 4-5 and/or 8-9 weeks) after the last priming immunization. It should also be readily apparent to one of skill in the art that there are several permutations and combinations that are encompassed using the DNA, bacterial and viral expression vectors or bacteria of the disclosure to provide priming and boosting regimens. For example, CMV vectors may be used repeatedly while expressing different antigens derived from the same or different pathogens.

In one embodiment, the boosting immunization step comprises the administration of a non-infectious dose of SIV or HIV, or an attenuated SIV or HIV (e.g., HIV or SIV depleted in protein nef). In one embodiment, the boosting immunization is in a form adapted for oral, rectal or vaginal administration.

Attenuated SIV or HIV virus are well known in the art. A non limitating example of said attenuated virus is an HIV or SIV depleted in protein nef (see, for example, Giorgi et al., J Med Primatol. 1996 June; 25(3):186-91).

In some embodiments, the second part and/or the third part of the combination, pharmaceutical combination, medicament or kit-of-parts according to the invention are to be administered at time and route of administration separately from the first part.

In one embodiment, the first part of the combination, pharmaceutical combination, medicament or kit-of-parts according to the invention is to be administered at least 2 times (e.g., at days 0 and 14). In another embodiment, the second part and/or the third part of the combination, pharmaceutical combination, medicament or kit-of-parts according to the invention are to be administered at least 2 times before the administration of the first (e.g., at days −7 and day −3), and at least 9 times after the administration (e.g., at days 3, 11, 38, 45, 52, 59, 66, 73 and 80).

In one embodiment, the first part of the combination, pharmaceutical combination, medicament or kit-of-parts according to the invention is to be administered at least 7 times (e.g., at days 0, 1, 3, 7, 28 and 29). In another embodiment, the second part and/or the third part of the combination, pharmaceutical combination, medicament or kit-of-parts according to the invention are to be administered before administrations of the first part (e.g., at days −3, 0, 28 and 29), and at least 1 more time (e.g., at days 57).

In one embodiment, the first part of the combination, pharmaceutical combination, medicament or kit-of-parts according to the invention is to be administered at least 7 times during the priming and boost steps (e.g., at days 0, 1, 2, 3, 5 for priming and days 28 and 29 for the first boost). The second part of the combination, pharmaceutical combination, medicament or kit-of-parts according to the invention is to be administered at least one time during the priming and first boost steps (e.g. from day 0 to 40) and at least one time after the last administration of the first part of the combination, pharmaceutical combination, medicament or kit-of-parts according to the invention. The third part of the combination, pharmaceutical combination, medicament or kit-of-parts according to the invention is to be administered 0, 1, 2 or 3 days before each administration of the first part of the combination, pharmaceutical combination, medicament or kit-of-parts according to the invention.

In one embodiment, the prime/boost mode comprises a step of administrating a non-infectious dose of SIV or HIV, or of an attenuated SIV or HIV (e.g., at day 60).

It will be understood that the total daily usage of the first part, the total daily usage of the second part and the total daily usage of third part in the combination, the pharmaceutical combination, medicament or kit-of-parts according to the invention will be decided by the attending physician within the scope of sound medical judgment. The specific dose for any particular subject will depend upon a variety of factors such as the infectious disease to be treated; the age, body weight, general health, sex and diet of the subject, and like factors well-known in the medical arts. Hence, the combination, the pharmaceutical combination, medicament or kit-of-parts according to the invention can be administered one or more times to the subject. Preferably, there is a set time interval between separate administrations of the combination, the pharmaceutical combination, medicament or kit-of-parts according to the invention. While this interval varies for every subject, typically it ranges from 1 days to several weeks, and is often 1, 2, 4, 6 or 8 days, or 1, 2, 4, 6 or 8 weeks. In one embodiment of the present invention, the interval is typically from 1 to 6 weeks. In one embodiment of the present invention, the interval is longer, advantageously about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks 70 weeks or 80 weeks. In one embodiment, the administration regimes typically have from 1 to 20 administrations of the 3 different parts according to the invention, but may have as few as one or two or four or eight or ten. In another embodiment the administration regimes is annual, biannual or other long interval (5-10 years).

In one embodiment, the subject is a mammal, a primate, preferably a human.

As an example, when the first part of the pharmaceutical combination, medicament or kit-of-parts according to the invention comprises a CMV vector as described herein above, and when the subject to be treated is a mammal, a primate or a human, the therapeutically effective dose of said CMV vector can range from a few to a few hundred micrograms (e.g., 5 to 500 μg per administration). The CMV vector can be administrated in any suitable amount to achieve expression at these dosage levels. In non-limiting examples, CMV vectors may be administered in an amount of at least $10^1$, $10^2$, $10^3$, $10^4$, $10^5$, $10^6$, $10^7$ or $10^8$ pfu per administration. Thus, CMV vectors may be administered in at least $10^1$ pfu, or in a range from about $10^1$ pfu to about $10^8$ pfu per administration. The CMV vector may be lyophilized for resuspension at the time of administration or may be in solution.

In one embodiment, the amount of CMV vectors, as described hereinabove, administered to the subject is at least of $10^1$, $\mathbf{10^2}$, $10^3$, $10^4$, $10^5$, $10^6$, $10^7$ or $10^8$ pfu. In one embodiment, the amount of CMV vectors, as described hereinabove, administered per administration ranges from about $10^1$ to about $10^8$, preferably from about $10^2$ to about $10^7$, more preferably from about $10^3$ to about $10^6$, and even more preferably from about $10^4$ to about $10^5$, including all integer values within those ranges. In one embodiment, the daily amount of CMV vectors, as described hereinabove, administered per day to the subject is at least of $10^1$ per day, $10^2$ per day, $10^3$ per day, $10^4$ per day, $10^5$ per day, $10^6$ per day, $10^7$ per day, $10^8$ per day of pfu. In one embodiment, the daily amount of CMV vectors, as described hereinabove, administered per day ranges from about $10^1$ to about $10^8$ per day, preferably from about $10^2$ to about $10^7$ per day, more preferably from about $10^3$ to about $10^6$ per day, and even more preferably from about $10^4$ to about $10^5$ per day, including all integer values within those ranges. In one embodiment, the amount of CMV vectors, as described hereinabove, administered to the subject is at least of $10^1$, $10^2$, $10^3$, $10^4$, $10^5$, $10^6$, $10^7$ or $10^8$ viruses/kg body.

As an example, when the first part of the pharmaceutical combination, medicament or kit-of-parts according to the invention comprises at least one infectious disease-related antigen and a non-pathogenic bacterium as described herein above, and when the subject to be treated is a human, the therapeutically effective dose of said non-pathogenic bacteria (i.e., *Lactobacillus* sp. or *Lactobacillus plantarum*) can range from about $10^1$ to about $10^{18}$ cfu per administration and the therapeutically effective dose of said infectious disease-related antigen (i.e., inactivated SIV or HIV viruses) can range from about $10^1$ to about $10^{14}$ viruses per administration.

In one embodiment, the amount of non-pathogenic bacteria, as described hereinabove, administered to the subject is at least of $10^1$, $\mathbf{10^2}$, $10^3$, $10^4$, $10^5$, $10^6$, $10^7$, $10^8$, $10^9$, $10^{10}$, $10^{11}$, $10^{12}$, $10^{13}$ or $10^{14}$ cfu. In one embodiment, the amount of non-pathogenic bacteria, as described hereinabove, administered per administration ranges from about $10^1$ to about $10^{18}$, preferably from about $10^2$ to about $10^{16}$, more preferably from about $10^4$ to about $10^{14}$, and even more preferably from about $10^6$ to about $10^{12}$, including all integer values within those ranges. In one embodiment, the daily amount of non-pathogenic bacteria, as described hereinabove, administered per day to the subject is at least of $10^1$ per day, $10^2$ per day, $10^3$ per day, $10^4$ per day, $10^5$ per day, $10^6$ per day, $10^7$ per day, $10^8$ per day, $10^9$ per day, $10^{10}$ per day, $10^{11}$ per day, $10^{12}$ per day, $10^{13}$ per day, $10^{14}$ per day, $10^{15}$ per day, $10^{16}$ per day, $10^{17}$ per day or $10^{18}$ per day of cfu. In one embodiment, the daily amount of non-pathogenic bacteria, as described hereinabove, administered per day ranges from about $10^1$ to about $10^{18}$ per day, preferably from about $10^2$ to about $10^{16}$ per day, more preferably from about $10^4$ to about $10^{14}$ per day, and even more preferably from about $10^6$ to about $10^{12}$ per day, including all integer values within those ranges. In one embodiment, the amount of non-pathogenic bacteria, as described hereinabove, administered to the subject is at least of $10^1$, $\mathbf{10^2}$, $10^3$, $10^4$, $10^5$, $10^6$, $10^7$, $10^8$, $10^9$, $10^{10}$, $10^{11}$, $10^{12}$, $10^{13}$ or $10^{14}$ bacteria/kg body.

In one embodiment, the amount of inactivated SIV or HIV viruses, as described hereinabove, administered to the subject is at least of $10^1$, $\mathbf{10^2}$, $10^3$, $10^4$, $10^5$, $10^6$, $10^7$, $10^8$, $10^9$, $10^{10}$, $10^{11}$, $10^{12}$, $10^{13}$, or $10^{14}$ viruses. In one embodiment, the amount of inactivated SIV or HIV viruses, as described hereinabove, administered per administration ranges from about $10^1$ to about $10^{18}$, preferably from about $10^2$ to about $10^{16}$, more preferably from about $10^4$ to about $10^{14}$, and even more preferably from about $10^6$ to about $10^{12}$, including all integer values within those ranges. In one embodiment, the daily amount of inactivated SIV or HIV viruses, as described hereinabove, administered per day to the subject is at least of $10^1$ per day, $10^2$ per day, $10^3$ per day, $10^4$ per day, $10^5$ per day, $10^6$ per day, $10^7$ per day, $10^8$ per day, $10^9$ per day, $10^{10}$ per day, $10^{11}$ per day, $10^{12}$ per day, $10^{13}$ per day, $10^{14}$ per day, $10^{15}$ per day, $10^{16}$ per day, $10^{17}$ per day or $10^{18}$ per day of viruses. In one embodiment, the daily amount of inactivated SIV or HIV viruses, as described hereinabove, administered per day ranges from about $10^1$ to about $10^{18}$ per day, preferably from about $10^2$ to about $10^{16}$ per day, more preferably from about $10^4$ to about $10^{14}$ per day, and even more preferably from about $10^6$ to about $10^{12}$ per day, including all integer values within those ranges. In one embodiment, the amount of inactivated SIV or HIV viruses, as described hereinabove, administered to the subject is at least of $10^1$, $10^2$, $10^3$, $10^4$, $10^5$, $10^6$, $10^7$, $10^8$, $10^9$, $10^{10}$, $10^{11}$, $10^{12}$, $10^{13}$, or $10^{14}$=viruses/kg body.

In one embodiment, the subject is a mammal, a primate, preferably a human, and said therapeutically effective dose of the first part of the combination, pharmaceutical combination medicament or kit-of-parts according to the invention is a daily dose to be administered in one, two, three or more takes or in one, two, three or more injections In one embodiment, the subject is a mammal, a primate, preferably a human, and said therapeutically effective dose of the second part of the combination, pharmaceutical combination medicament or kit-of-parts according to the invention is a daily dose to be administered in one, two, three or more takes or in one, two, three or more injections.

In one embodiment, the subject is a mammal, a primate, preferably a human, and said therapeutically effective dose of the third part of the combination, pharmaceutical combination medicament or kit-of-parts according to the invention is a daily dose to be administered in one, two, three or more takes or in one, two, three or more injections.

According to the present invention, the combination, pharmaceutical combination, medicament or kit-of-parts as described hereinabove is used alone.

Thus, in one embodiment, the combination, pharmaceutical combination, medicament or kit-of-parts according to the invention is used alone and comprises a therapeutically effective dose of first part as described hereinabove and a therapeutically effective dose of second part as described hereinabove and a therapeutically effective dose of third part as described hereinabove described hereinabove. In one embodiment, the combination, pharmaceutical combination, medicament or kit-of-parts according to the invention is used alone and comprises a therapeutically effective dose of first part as described hereinabove and a therapeutically effective dose of second part as described hereinabove. In another embodiment, the combination, pharmaceutical combination, medicament or kit-of-parts according to the invention is used alone and comprises a therapeutically effective dose of first part as described hereinabove and a therapeutically effective dose of third part as described hereinabove In one embodiment, the present invention, the combination, pharmaceutical combination, medicament or kit-of-parts as described hereinabove is used in combination with at least one further therapeutic agent.

Such administration may be simultaneous, separate or sequential. For simultaneous administration the agents may be administered as one composition or as separate compositions, as appropriate. The further therapeutic agent is typically relevant for disorders to be treated.

Thus, in one embodiment, the combination, pharmaceutical combination, medicament or kit-of-parts according to the invention comprises a therapeutically effective dose of first part as described hereinabove and a therapeutically effective dose of second part as described hereinabove and a therapeutically effective dose of third part as described hereinabove described hereinabove, and is used in combination with at least one further therapeutic agent. In one embodiment, the combination, pharmaceutical combination, medicament or kit-of-parts according to the invention comprises a therapeutically effective dose of first part as described hereinabove and a therapeutically effective dose of second part as described hereinabove, and is used in combination with at least one further therapeutic agent. In another embodiment, the combination, pharmaceutical combination, medicament or kit-of-parts according to the invention comprises a therapeutically effective dose of first part as described hereinabove and a therapeutically effective dose of third part as described hereinabove is used in combination with at least one further therapeutic agent.

In one embodiment, the further therapeutic agent is an antiretroviral therapy (ART).

As used herein, the term "antiretroviral therapy" or "highly active antiretroviral therapy" refers to any combination of antiretroviral (ARV) drugs to maximally suppress the HIV virus (e.g., reduce viral load reduce HIV multiplication . . . ), and stop the progression of HIV disease. There are several classes of HIV drug, such as, for example, non-nucleoside reverse transcriptase inhibitors (NNRTIs), nucleoside reverse transcriptase inhibitors (NRTIs), post-attachment inhibitors, protease inhibitors (PIs), CCR5 antagonists, integrase strand transfer inhibitors (INSTIs), fusion inhibitors. Generally, initial treatment regimens usually include two NTRIs combined with a third active anti-retroviral drug, which may be in the INSTI, NNRTI, or PI class. They may sometimes include a booster, which may be cobicistat (Tybost) or ritonavir (Norvir).

In one embodiment, the combination, pharmaceutical combination, medicament or kit-of-parts as described hereinabove is used in combination with an antiretroviral therapy (ART).

Thus, in one embodiment, the combination, pharmaceutical combination, medicament or kit-of-parts according to the invention comprises a therapeutically effective dose of first part as described hereinabove and a therapeutically effective dose of second part as described hereinabove and a therapeutically effective dose of third part as described hereinabove described hereinabove, and is used in combination with an antiretroviral therapy. In one embodiment, the combination, pharmaceutical combination, medicament or kit-of-parts according to the invention comprises a therapeutically effective dose of first part as described hereinabove and a therapeutically effective dose of second part as described hereinabove, and is used in combination with an antiretroviral therapy. In another embodiment, the combination, pharmaceutical combination, medicament or kit-of-parts according to the invention comprises a therapeutically effective dose of first part as described hereinabove and a therapeutically effective dose of third part as described hereinabove is used in combination with an antiretroviral therapy.

According to the present invention, the combination pharmaceutical combination medicament or kit-of-parts as described hereinabove is for use in the prevention or treatment of an infectious disease in a subject in need thereof.

As used herein, the term "infectious disease" refers to a disease caused by a pathogen, such as a fungus, parasite, protozoan, bacterium or virus. Examples of "infectious diseases" include, without being limited to, influenza virus infection, monkeypox virus infection, West Nile virus infection, Chikungunya virus infection, Ebola virus infection, hepatitis C virus infection, poliovirus infection, dengue fever, Acquired immune deficiency syndrome (AIDS) or a Simian Immunodeficiency virus (SIV) infection and the recombinant RhCMV or HCMV vector encodes an antigen from HIV or SIV, skin warts, genital warts, respiratory papillomatosis, Malaria, Ebola hemorrhagic fever, Tuberculosis, Herpes disease (e.g., Genital Herpes, Chicken pox or Herpes Zoster, Infectious mononucleosis), tuberculosis infection (caused by *Mycobacterium tuberculosis*), typhoid infection or fever (caused by *Salmonella typhi*).

In one embodiment, the infectious disease to be prevented or treated is preferably acquired immune deficiency syndrome (AIDS), a human immunodeficiency virus (HIV) infection or a simian immunodeficiency virus (SIV) infection.

In one embodiment, the infectious disease to be prevented or treated is acquired immune deficiency syndrome (AIDS).

In some embodiments, the combination pharmaceutical combination medicament or kit-of-parts as described hereinabove is for use in the prophylactic treatment or in the curative treatment of an infectious disease in a subject in need thereof.

EXAMPLES

Figure 1A:
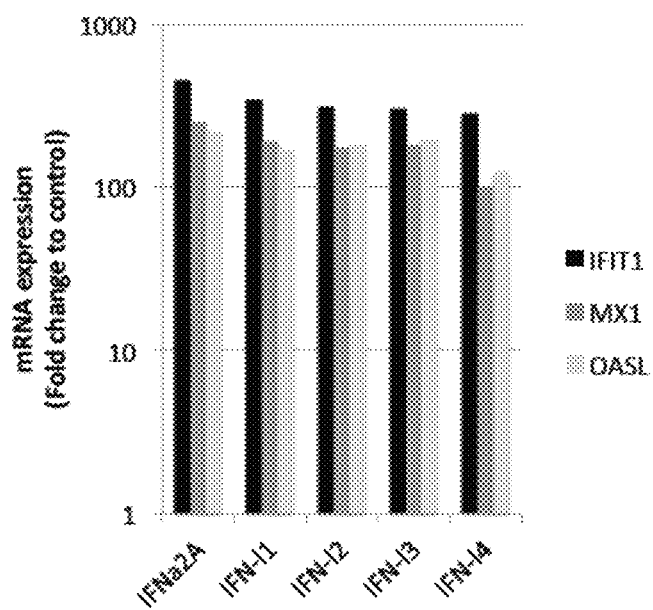
FIG. 1A. Antiviral activity of type I and type III interferons. Expression of ISGs in HepG2. HepG2 cells were treated with IFNα2a or IFNλ1-4 (10 ng/ml). After 4 h of stimulation, qRT-PCR were used to examine the mRNA levels of the interferon-induced genes, IFIT1, MX1 and OASL and fold-changes was calculated by $2^{-\Delta\Delta Ct}$ method as compared with non-treated cell control and using endogenous S14 mRNA level for normalization.

The present invention is further illustrated by the following examples.

Example 1: Effects of Type I and Type III Interferons on Innate and Adaptative Immune Responses Materials and Methods
Human Cell Lines HCC HepG2 and normal kidney epithelial Vero cell lines were obtained from ATCC. Cells were grown in Dulbecco's Modified Eagle Medium supplemented with 10% heat-inactivated Fetal Bovine Serum, 2 mM L-glutamine, 1% penicillin and streptomycin solution in hypoxia 2%. Cancer cell lines were grown to 70-100% confluency, subsequently passaged for a maximum of 5 times and freshly thawed thereafter. Cells were detached by means of accutase, resuspended in FBS-containing medium and collected by means of centrifugation (300 g, 3 min). Cell numbers were determined by means of trypan blue.

Human Blood Sample

Blood samples from healthy individuals originated from Etablissement Francais du Sang (EFS, Paris). Blood cells are collected using standard procedures.

Cell Purification and Culture

Peripheral blood mononuclear cells (PBMCs) are isolated by density gradient centrifugation on Ficoll-Hypaque (Pharmacia). PBMCs are used either as fresh cells or stored frozen in liquid nitrogen. T-cell subsets and T cell-depleted accessory cells (ΔCD3 cells) are isolated from either fresh or frozen PBMCs. T cell-depleted accessory cells (ΔCD3 cells) are isolated by negative selection from PBMCs by incubation with anti-CD3-coated Dynabeads (Dynal Biotech) and are irradiated at 3000 rad (referred to as ΔCD3-feeder). $CD4^+$ T cells are negatively selected from PBMCs with a $CD4^+$ T-cell isolation kit (Miltenyi Biotec), yielding $CD4^+$ T-cell populations at a purity of 96-99%. T cell subsets are cultured either in IMDM supplemented with 5% SVF, 100 IU/ml penicillin/streptomycin, 1 mM sodium pyruvate, 1 mM nonessential amino acids, glutamax and 10 mM HEPES (IMDM-5 media) in hypoxia 2%.

Freezing and Thawing of Cells

Cells were frozen in FBS containing 10% DMSO. Cryo tubes were placed in CoolCell (Biocision) freezing containers and incubated at −80° C. After 2 days tubes were transferred to liquid nitrogen and stored until required. Thawing of cells was performed by placing cryo tubes in a 37° C. water bath for approximately 30 seconds. Next, cell suspension was mixed with equivalent volume of pre-warmed media and subsequently transferred to falcon tubes containing the same medium. Cells were pelleted by centrifugation (300 g, 3 min) to remove DMSO. The cell pellet was resuspended in cell culture medium Real-Time PCR for ISGs Detection HepG2 cells were seeded at a density of $2 \times 10^5$ cells per well in 12-well plates and incubated for 24 h. Then, fresh media was added with the indicated interferons. The cells were incubated for 4 h and then lysed, and RNA was purified using an extraction kit (Qiagen), according to the manufacturer's instructions. Synthesis of cDNA was performed using the PrimeScript RT Reagent kit (TAKARA). Quantitative PCR was carried out using the Power SYBR Green PCR Master Mix (Applied Biosystems) on a LightCycler 480 instrument (Roche). Each reaction was carried out in duplicate in a total volume of 100 μL. Primers were designed to be intron-spanning using Primer3 or Primer Express® v3.0 software (Applied Biosystems). To measure the cellular transcriptional response to IFN stimulation, 3 ISG targets, MXI, OASL and ISG15, were selected based on published results investigating the transcriptional response in IFN-stimulated PBMCs (see, for example, Waddell et al. (2010) PLoS One. 5(3):e97532). For gene induction assays, fold change values were calculated using the ΔΔCt method. The geometric mean of the Ct values of the reference genes, S14, was used as a reference value.

Virus Production

The virus used EMCV (FA strain) was grown on monolayers of Vero cells to complete cytopathic effect or until all cells were affected by the infection as determined by microscopy and prepared by two cycles of freezing and thawing, followed by centrifugation for 30 min at 5,000×g for removal of cellular debris.

Antiviral Assay

Antiviral assays were done on HepG2 cells, which were seeded in DMEM supplemented with 10% FCS at a density of $1.5 \times 10^4$ in 96-well plates and left to settle. The cells were incubated with indicated doses of IFNs for 24 h before challenge with EMCV. The cells were incubated with virus for 48 h. The medium was removed between each step. The viability of the cells was analyzed by a bioassay based on the dehydrogenase system; this system in intact cells will convert the substrate, MTT, into formazan (blue), which in turn can be measured spectrophotometrically. Briefly, the cells were given MTT and incubated for 2 h. An extraction buffer (containing 6 to 11% sodium dodecyl sulfate and 45% N,N-dimethylformamide) was added to the cells, and the cells were then incubated overnight at 37° C. Subsequently, the absorbance at 570 nm was determined employing the extraction buffer as the blank probe. A570 was directly proportional to antiviral activity.

Flow Cytometry Analysis $CD3^+$ T Cells Staining:

anti-CD4 (SK3)-APC, anti-CD3 (UCHT1)-FITC, anti-CD8 (RPA-T8)-BV421 are from Becton Dickinson. Cells are stained for surface markers (at 4° C. in the dark for 30 min) using mixtures of Ab diluted in PBS containing 3% FBS, 2 mM EDTA (FACS buffer).

STAT1 Signaling Analysis:

Flow cytometry analysis of STAT1 phosphorylation (pSTAT1) was conducted in $CD4^+$ T cells by using BD Phosflow technology according to the manufacturer's instructions (BD Bio-sciences, San Jose, Calif.). $CD4^+$ T cells were stimulated by incubation with interferon type I and Type III at 37° C. for 20 min or left untreated. Activation was stopped by fixation using BD Phosflow Lyse/Fix Buffer (BD Biosciences) and cells were permeabilized with BD Perm Buffer III (BD Biosciences). Cells were stained with antibody recognizing specific phosphorylated STAT tyrosines: p-STAT1 (Y701)-PE. In multiparametric immunophenotyping experiments, cells were simultaneously stained with anti-CD3-FITC and 7-AAD. Increases in pSTAT1 were assayed as a ratio of induction over baseline levels (MFI fold change=MFI cytokine-stimulated/MFI untreated cells)

CFSE Staining:

$CD4^+$ T cells were stained with 1 μM CFSE (CellTrace cell proliferation kit; Molecular Probes/Invitrogen) in PBS for 8 min at 37° C. at a concentration of 1.107 cells/ml. The labeling reaction was stopped by washing twice the cell with RPMI-1640 culture medium containing 10% FBS. The cells were then re-suspended at the desired concentration and subsequently used for proliferation assays.

7-AAD Staining:

Apoptosis of stimulated CFSE-labeled $CD4^+$ T was determined using the 7-AAD assay. Briefly, cultured cells were stained with 20 μg/mL nuclear dye 7-amino-actinomycin D (7-AAD; Sigma-Aldrich, St-Quentin Fallavier, France) for 30 minutes at 4° C. FSC/7-AAD dot plots distinguish living ($FSC^{high}$/7-AAD⁻) from apoptotic ($FSC^{low}$/7-AAD⁺) cells and apoptotic bodies ($FSC^{low}$/7-AAD⁺) and debris (($FSC^{low}$/7-AAD⁻). Living cells were identified as $CD3^+$7-AAD-$FSC^+$ cells.

Appropriate isotype control Abs are used for each staining combination. Samples are acquired on a BD LSR FORTESSA flow cytometer using BD FACSDIVA 8.0.1 software (Becton Dickinson). Results are expressed in percentage (%) or in mean fluorescence intensity (MFI).

Functional Assay

T Cell Proliferation:

T cell proliferation was assessed with CFSE-dilution assays. For CFSE-dilution assay, at coculture completion, stimulated CFSE-labeled $CD4^+$ T cells were harvested, co-stained with anti-CD3 mAb and 7-AAD, and the percentage of proliferating cells (defined as CFSE low fraction) in gated CD3$^+$7-AAD$^-$ cells was determined by flow cytometry.

T Cell Activation:

CD38 Median Fluorescence Intensity (MFI) of CD38 expression was measured by flow cytometry in CD3$^+$7-AAD-CFSE$^+$ stimulated CD4$^+$ T cells at the end of the culture.

CD4$^+$ T Cell Polyclonal Stimulation:

CFSE-stained CD4$^+$ T cells (5×10$^4$/well) were cultured in 96 round-bottomed microwells in the presence of ΔCD3-feeder (1×10$^5$/well) and plate-bound anti-CD3 Ab (2 μg/ml), soluble anti-CD28 mAb (2 μg/ml). CD4$^+$ T cell proliferation was evaluated with CFSE dilution assays as described above by flow cytometry. Cells were stimulated in presence of different amounts of recombinant cytokines.

Allogeneic Mixed Lymphocyte Reaction:

CFSE-stained CD4$^+$ T cells (5×10$^4$/well) were cultured in 96 round-bottomed microwells in the presence of allogeneic mature DC. Proliferation of allo-activated CD4$^+$ T cells with CFSE dilution assays as described above by flow cytometry. Cells were stimulated in presence of different amounts of recombinant cytokines.

Stat1 Phosphorylation Analysis:

CD4$^+$ T cells were stimulated with IFN-λ1, IFN-λ2, IFN-λ3, IFN-λ4, or IFN-α2a (10 ng/ml) for 20 min, or were left unstimulated (control). Phosphorylated Stat1 levels was assessed by flow cytometry as described above.

Results

Type I interferons (IFN-α/β) and the more recently identified type III IFNs (IFN-λ) function as the first line of defense against virus infection, and regulate the development of both innate and adaptive immune responses. Type III IFNs were originally identified as a novel ligand-receptor system acting in parallel with type I IFNs, but subsequent studies have provided increasing evidence for distinct roles for each IFN family.

The inventors aimed to evaluate the effects of type I and type III interferons on both innate (antiviral) and adaptive immune response (CD4$^+$ T cell proliferation).

Antiviral Activities of Types I and III

The ability of IFN type I and III to induce the expression of interferon-stimulated genes (ISGs) was analyzed by qPCR.

Briefly, the antiviral activity of type I and III was tested in HepG2 cells treated with IFN-α2a, IFNλ1, IFNλ2, IFNλ3 or IFNλ4 for 4 hours. Then the induction of the well-known interferon-stimulated genes (ISGs) MX1, IFIT1 and OASL was monitored by qPCR.

As shown in FIG. 1A, all five interferons clearly induced all three ISGs.

Since the investigated ISGs are functionally related to an antiviral defense, the inventors further evaluate the capacity of both IFN to protect HepG2 cells from EMCV-induced cytopathogenic effect.

Briefly, cells were seeded in a 96-well microtiter plate and treated with the indicated amount of IFNs for 24 h and then challenged with EMCV for 20 h. Cell survival was measured by an MTT coloring assay.

Figure 1B:
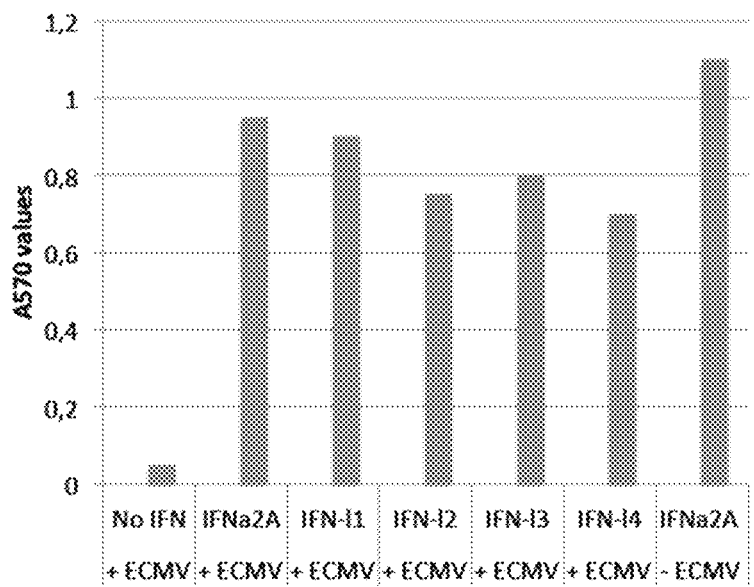
FIG. 1B. Antiviral activity of type I and type III interferons. Antiviral activity of type I and III IFNs against EMCV. IFNα2a or IFNλ1/2/3/4 (10 ng/ml) were added to HepG2 cells 24 h prior to challenge with EMCV. Forty-eight after infection with EMCV, cells were assayed for viability with a bioassay. A570 values were directly proportional to cell viability and therefore antiviral activity of the respective IFNs. IFN-α treatment without viral challenge was used as a baseline of the viability of the cells.

As shown in FIG. 1B, IFN type III and IFN-α2a have intrinsic cellular antiviral activity and are able to fully protect HepG2 cells challenged with EMCV.

Anti-Proliferative Activity of Type I and Type III Interferons Against CD4$^+$ T Cells Proliferation The effect of IFN-type I and IFN type III on CD4$^+$ T cells proliferation in response either to polyclonal or to allogeneic stimulation was evaluated in a mixed lymphocyte reaction (MLR) assay.

Briefly, CFSE labelled CD4$^+$ T cells were first stimulated with poly I:C matured allogeneic dendritic cells in presence of different dose of IFNs. At 5 days post activation, the CFSE fluorescence dilution was analyzed.

Figure 2:
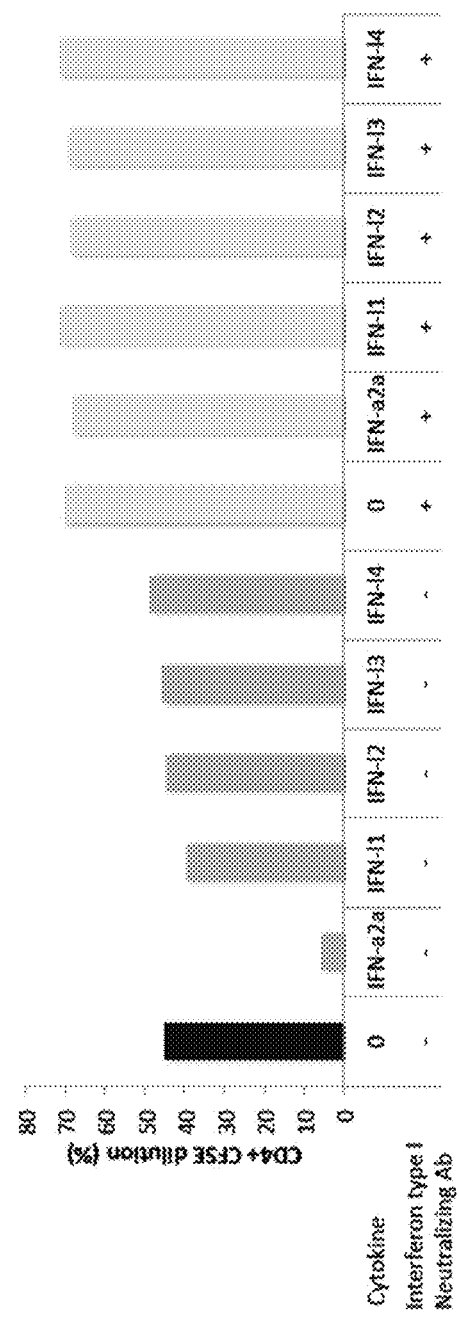
FIG. 2. Anti-proliferative activity of type I and type III interferons against CD4$^+$ T cells. CFSE-stained CD4+ T cells ($10 \times 10^4$/well) were stimulated for 5 days in 96 round-bottomed microwells with allogeneic poly I:C matured DC in absence (control) or presence of 10 ng/ml of IFN-α 2a, or IFNλ1 or IFNλ2 or IFNλ3 or IFNλ4. When indicated, anti-interferon type I receptor antibody was added. The percentage of CFSE dilution was evaluated by flow cytometry.

As shown in FIG. 2, IFN-α2a inhibits the proliferation of stimulated CD4$^+$ T cells, while IFN type III exhibits no ability to suppress their proliferation. Of note, when the MLR was performed in the presence of anti-interferon type I receptor antibody, CD4$^+$ T cells exhibit a greater proliferation. Thus, IFN-type I but not IFN type III inhibit the proliferation of allo-activated CD4$^+$ T cells.

Moreover, the analysis of mRNA levels of the interferon-induced genes (ISG), IFIT1, MX1 and OASL in IFNs treated CD4$^+$ T cells confirmed the lack or minimal sensitivity of CD4$^+$ T cells to interferon type III.

Figure 3:
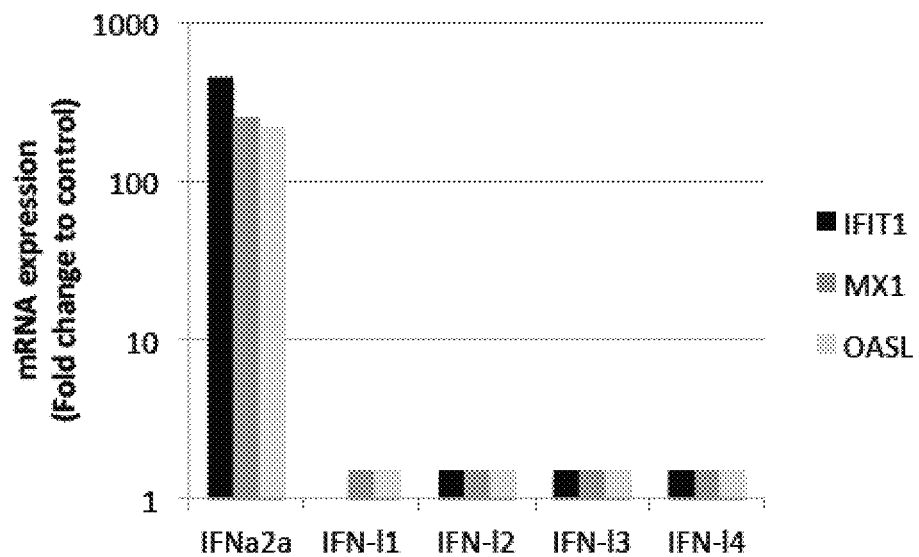
FIG. 3. IFN-α2a but not IFN-type III induces the expression of ISGs in CD4$^+$ T cells. CD4$^+$ T cells were treated with IFNα2a or IFNλ1/2/3/4 (10 ng/ml). After 4 h of stimulation, qRT-PCR were used to examine the mRNA levels of the interferon-induced genes, IFIT1, MX1 and OASL and fold-changes was calculated by $2^{-\Delta\Delta Ct}$ method as compared with non-treated cell control and using endogenous S14 mRNA level for normalization.

Indeed, as shown in FIG. 3, ISGs are induced only in CD4$^+$ T cells stimulated with IFN-α2a. Thus, IFN-α2a but not IFN-type III induce the expression of ISGs in CD4$^+$ T cells.

Because the Jak-STAT1/2 pathway being the major regulators of the transcription of ISG, the inventors have analyzed the phosphorylation levels of Stat1 proteins in response to IFN-type I, or interferon type III within CD4$^+$ T cells.

Figure 4:
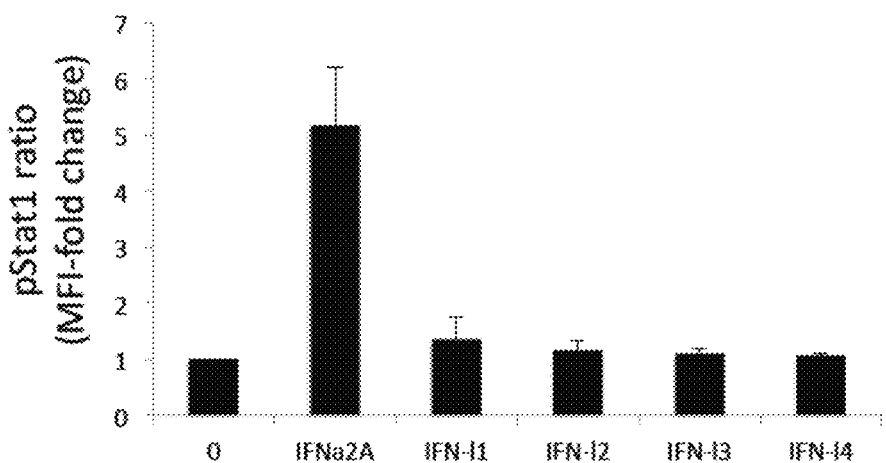
FIG. 4. IFN-α2a but not IFN-type III stimulates the phosphorylation of Stat1 in CD4$^+$ T cells. CD4$^+$ T cells were stimulated with 10 ng ml$^{-1}$ of IFNλ-1, IFN-λ2, IFN-λ3, IFN-λ4, or IFN-α2a for 20 min, or were left unstimulated (control). Increases in pSTAT1 were evaluated as a ratio of induction over baseline levels (MFI fold change=MFI cytokine-stimulated/MFI untreated cells)

As shown in FIG. 4, only IFN-α2a was able to stimulate the phosphorylation of Stat1 within CD4$^+$ T cells. Therefore, IFN-α2a but not IFN-type III induces tyrosine phosphorylation of STAT1 in CD4$^+$ T cells.

Induction of Chronic Immune Activation in Presence of Type I and III Interferons.

Because chronic immune activation has been reasoned to be a significant contributor to disease progression in HIV-1-infected subjects, it is possible to monitor disease progression by measuring the expression of activation markers on CD4$^+$ T cell surface. Thus, the inventors have evaluated, by flow cytometry, the capacity of both IFNs to increase the CD38 expression on stimulated CD4$^+$ T cells.

Figure 5:
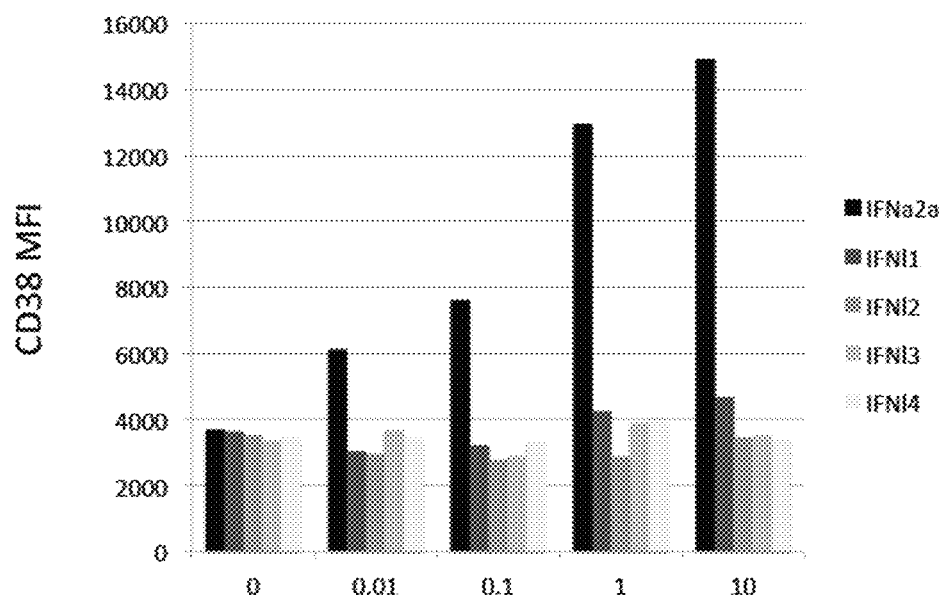
FIG. 5. IFN-α2a but not IFN-type III increases CD38 expression in CD3/CD28 stimulated CD4$^+$ T cells. CFSE-stained CD4$^+$ T cells ($4 \times 10^4$/well) were cultured in 96 round-bottomed microwells in the presence of λCD3-feeder ($4 \times 10^4$/well) and plate-bound anti-CD3 mAb (2 μg/ml), soluble anti-CD28 mAb (2 μg/ml) with increasing dose of IFN-α2a or IFN type III. CD38 Median Fluorescence Intensity (MFI) was measured by flow cytometry in CD3$^+$7-AAD-CFSE$^+$ stimulated CD4$^+$ T cells at the end of the culture.

As shown in FIG. 5, only IFN-α2a was able to enhance the expression of CD38 on stimulated CD4$^+$ T cells.

Collectively, these ex vivo experiments show that while exhibiting anti-viral activity, as does IFN-α, interferon type III, by contrast to the immunosuppressive IFN-α, have no effect on CD4$^+$ T cell activation and proliferation. Indeed, interferon type III do not inhibit the initiation of the adaptative immune reaction as do IFN-α2a.

In conclusion, while interferon type I and type III are induced by the same viral stimulating factors and exhibit similar signature profiles, their biological activity appears not redundant but rather complementary. Indeed, following viral infection, during the innate phase of the immune response, interferons type III exert their antiviral effects in mucosal sites whereas IFN-α act more systemically in the whole organism. Furthermore, the subsequent adaptive immune reaction is inhibited at its initiation level by the immunosuppressive effect of the IFN-α on activated CD4+ T cells.

Example 2: Ex Vivo Generation and Expansion of Antigen (Ag) Specific CD8+ HLA-E Restricted T Cells Materials and Methods
Human Blood Sample.

Blood samples from healthy individuals originated from Etablissement Francais du Sang (EFS, Paris). Blood cells are collected using standard procedures.

Cell Purification and Culture

Peripheral blood mononuclear cells (PBMCs) are isolated by density gradient centrifugation on Ficoll-Hypaque (Pharmacia). PBMCs are used either as fresh cells or stored frozen in liquid nitrogen. T-cell subsets and T cell-depleted accessory cells (ΔCD3 cells) are isolated from either fresh or frozen PBMCs. T cell-depleted accessory cells (ΔCD3 cells) are isolated by negative selection from PBMCs by incubation with anti-CD3-coated Dynabeads (Dynal Biotech) and are irradiated at 3000 rad (referred to as ΔCD3-feeder). Naïve CD8+ T cells were isolated from PBMCs by negative selection using a MACS system. CD14+ monocytes are isolated from PBMCs by positive selection using a MACS system. T cell subsets are cultured either in IMDM supplemented with 5% SVF, 100 IU/ml penicillin/streptomycin, 1 mM sodium pyruvate, 1 mM nonessential amino acids, glutamax and 10 mM HEPES (IMDM-5 media) in hypoxia 2%.

Freezing and Thawing of Cells

Cells were frozen in FBS containing 10% DMSO. Cryo tubes were placed in CoolCell (Biocision) freezing containers and incubated at −80° C. After 2 days tubes were transferred to liquid nitrogen and stored until required. Thawing of cells was performed by placing cryo tubes in a 37° C. water bath for approximately 30 seconds. Next, cell suspension was mixed with equivalent volume of pre-warmed media and subsequently transferred to falcon tubes containing the same medium. Cells were pelleted by centrifugation (300 g, 3 min) to remove DMSO. The cell pellet was resuspended in cell culture medium Dendritic Cell Generation Monocytes were cultured in RPMI supplemented with 10% heat-inactivated Fetal Bovine Serum, 2 mM L-glutamine, 1% penicillin and streptomycin solution (RPMI medium), in presence of IL-4 (20 ng/ml) and GM-CSF (20 ng/ml). At day 6, DC were matured overnight in different cocktails: a (IL-1β (2 ng/ml) IL-6 (30 ng/ml), PGE2 (1 microg/ml) and TNF-α (10 ng/ml), LPS 250 ng/ml, Poly I:C (150 ng/ml).

In Vitro Generation of TAP-Inhibited Stimulator Cells for MLR Assay

Matured DC, obtained as described above, are electroporated with 20 μg of RNA synthesized from the pGem4Z vector containing the UL49.5 gene from BHV-1 (see, for example, Lampen et al. (2010) J Immunol. 185(11):6508-17).

Induction and Expansion of Human Ag-Specific CD8 T Cells HLA-E Restricted

TAP-inhibited mature DCs (TAP-mDC) were pulsed with 50 μg/ml synthesized peptide. Then DCs were mixed with naive CD8 T cells at a ratio 1:10. IL-21 (30 ng/ml) was immediately added after the culture was initiated. After 3 days, half of medium were exchanged and 30 ng/ml IL-21, 20 ng/mL interleukin 15 (IL-15) and 500 ng/mL soluble, Fc-fused IL15-Receptor alpha (sIL15Ra-Fc, R&D Systems) were added. After 10 days of coculture, T cells were restimulated with peptides pulsed TAP-inhibited mature DCs in presence of IL-21, IL-15 and Fc-fused IL15-Receptor alpha. IL-2 (50 IU/ml) and IL-7 (10 ng/ml) were added 1 day after the second stimulation to further facilitate expansion of activated Ag-specific T cells. Peptide-specific expansion of T cells was monitored by flow cytometric analysis using MHC-peptide pentamer.

Flow Cytometry Analysis

T cells were transferred per v-bottomed 96-well, washed (300 g, 2 min) and stained in 100 μL FACS buffer (PBS, 3% FBS, 2 mM EDTA) containing respective peptide-MHC pentamers (1:10, ProImmune) for 1 hour at 4° C. Cells were washed three times in FACS buffer and subjected to flow cytometric analysis.

Appropriate isotype control Abs are used for each staining combination. Samples are acquired on a BD LSR FORTESSA flow cytometer using BD FACSDIVA 8.0.1 software (Becton Dickinson). Results are expressed in percentage (%) or in mean fluorescence intensity (MFI).

Results

Recent advances in the field of SIV vaccinology have highlighted the role of MHC-1b/E-restricted CD8+ T cell responses in controlling SIV infection in rhesus macaques, thereby raising the possibility that the adoptive transfer of HLA-E-restricted CD8+ T cells could be beneficial in controlling HIV-1 infection. The inventors thus established an experimental procedure to generate and expand autologous CD8+ T cell lines directed to peptide presented by HLA-E, using as HLA-E peptide, the CMV UL40-derived peptide (VMAPRTLIL, SEQ ID NO: 5) and as stimulator cells, a TAP-inhibited mature DC. The use of VMAPRTLVL-HLA-E pentamer (VMAPRTLVL, SEQ ID NO: 6) allows to assess specific T cell expansion.

Figure 6:
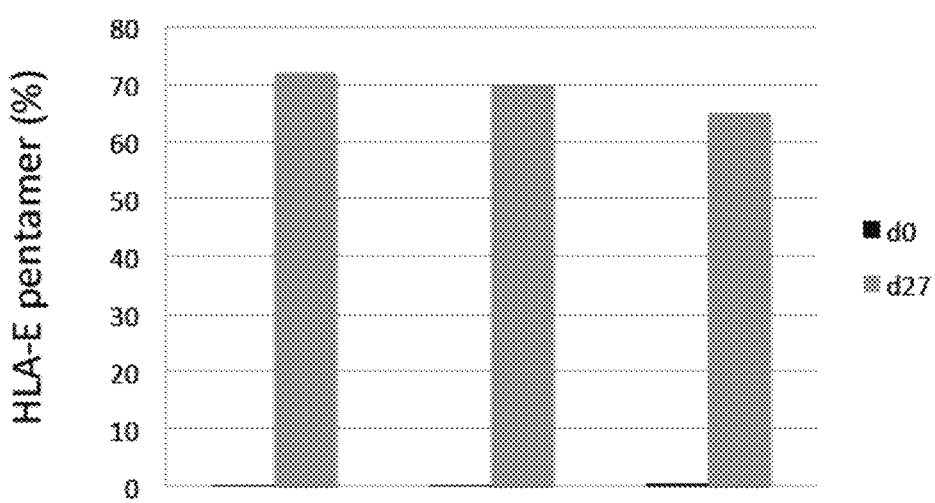
FIG. 6. Generation and expansion of peptide-specific CD8 HLA-E restricted by peptide-loaded m-DCs. TAP-inhibited mDCs was pulsed with peptides (10 μM for 1 h) and co-cultured with autologous naive CD8$^+$ T cells at a 1:10 ratio. Peptide positive CD8$^+$ T cells was monitored at day 0 and one week after the last stimulation by flow cytometric analysis using MHC-peptide pentamers. Data are expressed as percentage of tetramer-positive cells among CD8+ T cells.

As shown in FIG. 6, following two rounds of stimulation, 72% CD8+ T cells in culture were tetramer positive, suggesting that the inventors have developed a culture system that facilates the expansion and the generation of Ag-specific CD8+ T cells HLA-E restricted.

Such ex vivo expanded cellular material represent per se an example of active principle for adoptive T cell therapy.

Figure 7:
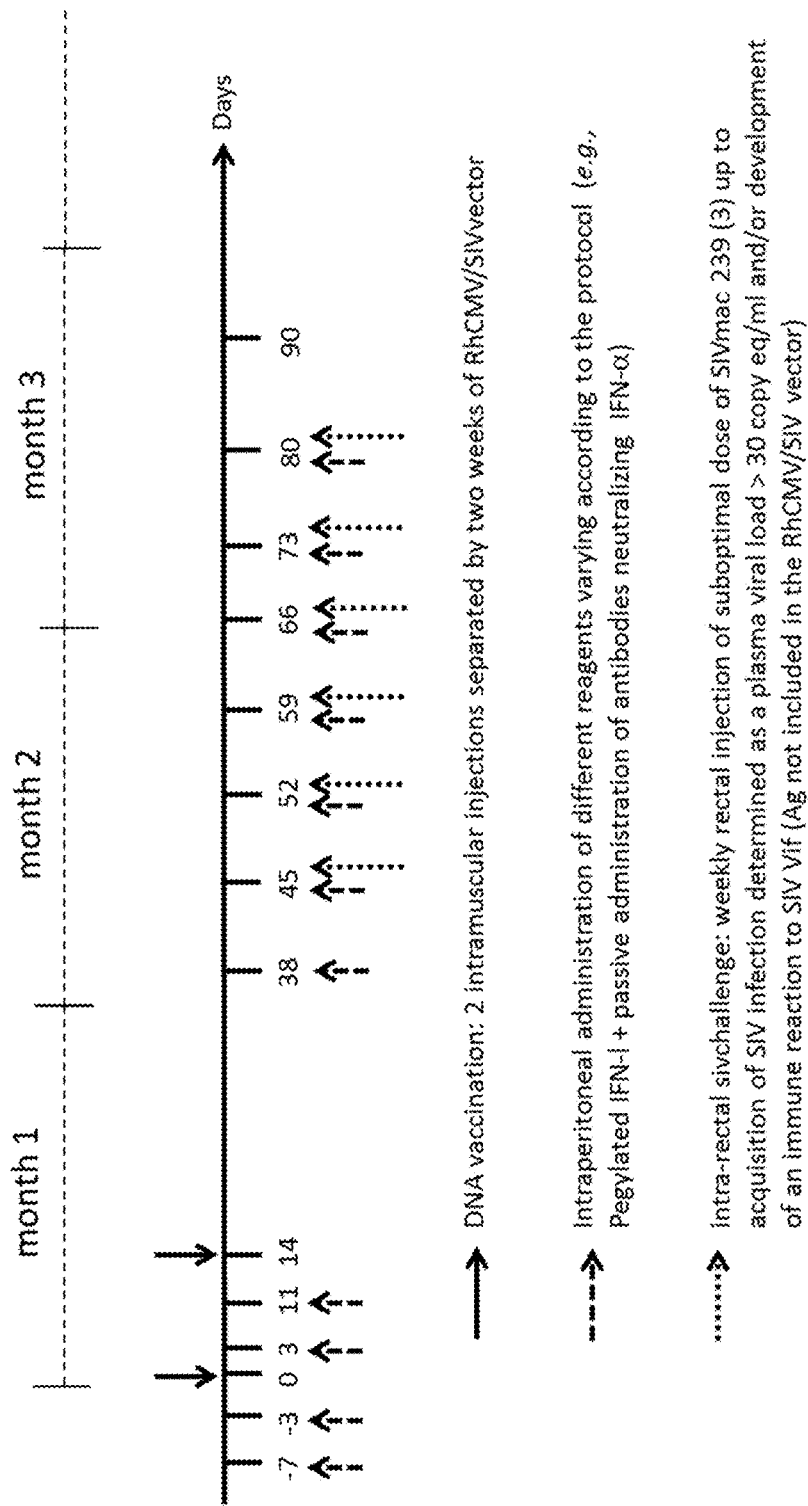
FIG. 7. Schematic representation of the immunization protocol in macaques with RhCMV/SIV vectors.

Example 3: Prophylactic Vaccine to SIV in Macaques with Recombinant RhCMV/SIV Vectors The FIG. 7 is a schematic representation of the immunization protocol in macaques.

Immunization Protocol (DNA Vaccination)

The CD8 vaccine composition is in a form adapted to intramuscular administration and comprises RhCMV/SIV vectors (see Hansen et al. (2013) Science 24; 340(6135): 1237874; Hansen et al. (2016) Science; 351(6274)). Chinese rhesus macaques receive 2 intramuscular (i.m.) injections of said CD8 vaccine composition at days 0 and 14.

At days −7, −3, 3, 11, 38, 45, 52, 59, 66, 73 and 80, macaques receive (i.p.) injection of interferon lambda 1 (50-100 μg) and/or anti-IFN-α antibodies (PBL, 100 μg/kg).

Pre-challenge

Optionally, macaques receive intra-rectal injection of non-infectious dose of SIV or an attenuated SIV (e.g., SIV depleted in protein nef).

Challenge

At days 45, 52, 59, 66, 73, and 80 macaques receive intra-rectal injection of suboptimal dose of SIVmac 239.

Acquisition of SIV infection is determined as a plasma viral load >30 copy eq/mL and/or development of an immune reaction to SIV Vif (i.e., an antigen not included in the RhCMV/SIV vector).

Example 4: Prophylactic Vaccine to SIV in Macaques with Inactivated SIV and Living *Lactobacillus plantarum*

Figure 8:
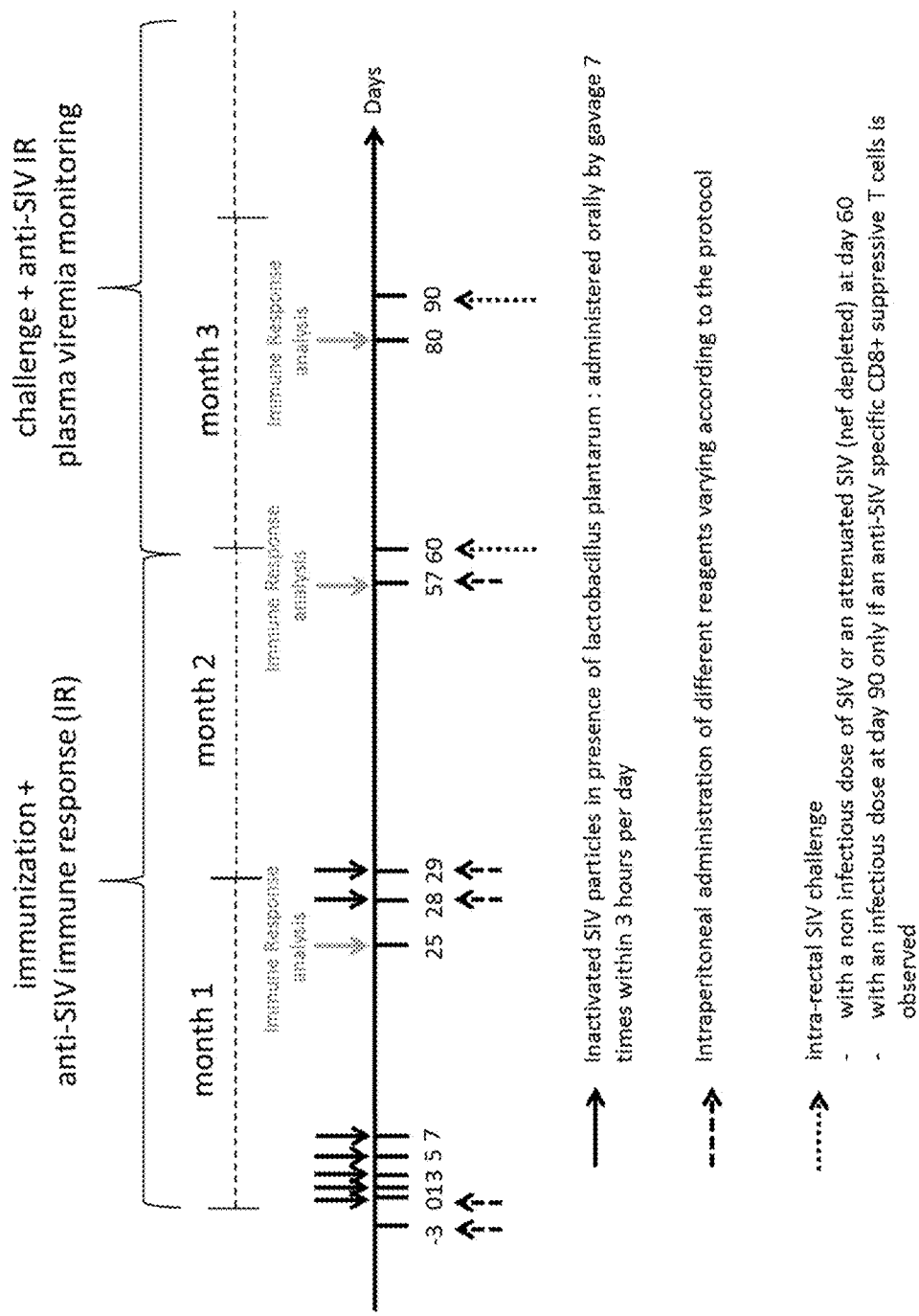
FIG. 8. Schematic representation of the oral immunization protocol in macaques with inactivated SIV and living *Lactobacillus plantarum*.

The FIG. 8 is a schematic representation of the oral immunization protocol in macaques.

Oral Priming Immunization Protocol

The CD8 vaccine composition is in a form adapted to intragastrically administration and comprises: $4 \times 10^7$ copies/mL of an inactivated SIV and $3 \times 10^9$ cfu/mL of living *Lactobacillus plantarum* in maltodextrin (20%) solution. Chinese rhesus macaques receive 30 mL of said CD8 vaccine composition and then 25 mL of the same composition every 30 min for 3 hours, at days 0, 1, 3, 5, 7 and 28, 29.

At day −3 and before each series of immunizations at days 0, 28 and 29, macaques receive (i.p.) injections of a combination of different reagents according to the protocol as described hereinafter:

Protocol 1: nothing
Protocol 2: poly I:C (100 µg/kg) and interferon lambda 1 (50-100 µg)
Protocol 3: polyclonal anti-IFN-α antibodies (PBL, 100 µg/kg) and poly I:C (100 µg/kg)
Protocol 4: polyclonal anti-IFN-α antibodies (PBL, 100 µg/kg), poly I:C (100 µg/kg) and interferon lambda 1 (50-100 µg)

At day 57, macaques receive injection of polyclonal anti-IFN-α antibodies (PBL, 100 µg/kg), poly I:C (100 µg/kg) and/or interferon lambda 1 (50-100 µg).

Bosting Immunization (Pre-Challenge)

At day 60, macaques receive intra-rectal injection of non-infectious dose of SIV or an attenuated SIV (e.g., SIV depleted in protein nef).

Immune Response Analysis

Anti-SIV immune response is analyzed at day 25, 57 and 80. The analysis of the anti-SIV immune response comprises the monitoring of:

Plasma SIV IgM/IgG/IgA antibody titers, and/or
SIV Gag specific CD8$^+$ T cell and CD8$^+$ T cell-mediated anti-viral activity.

Challenge

At day 90, macaques receive intra-rectal injection of an infectious dose of SIV only if an anti-SIV specific CD8$^+$ suppressive T cells (as described in the present invention) is observed.

After challenge, anti-SIV immune responses and plasma viremia are monitored every two weeks.

Example 5: Prophylactic Vaccine to HIV in BLT Mice

Figure 9:
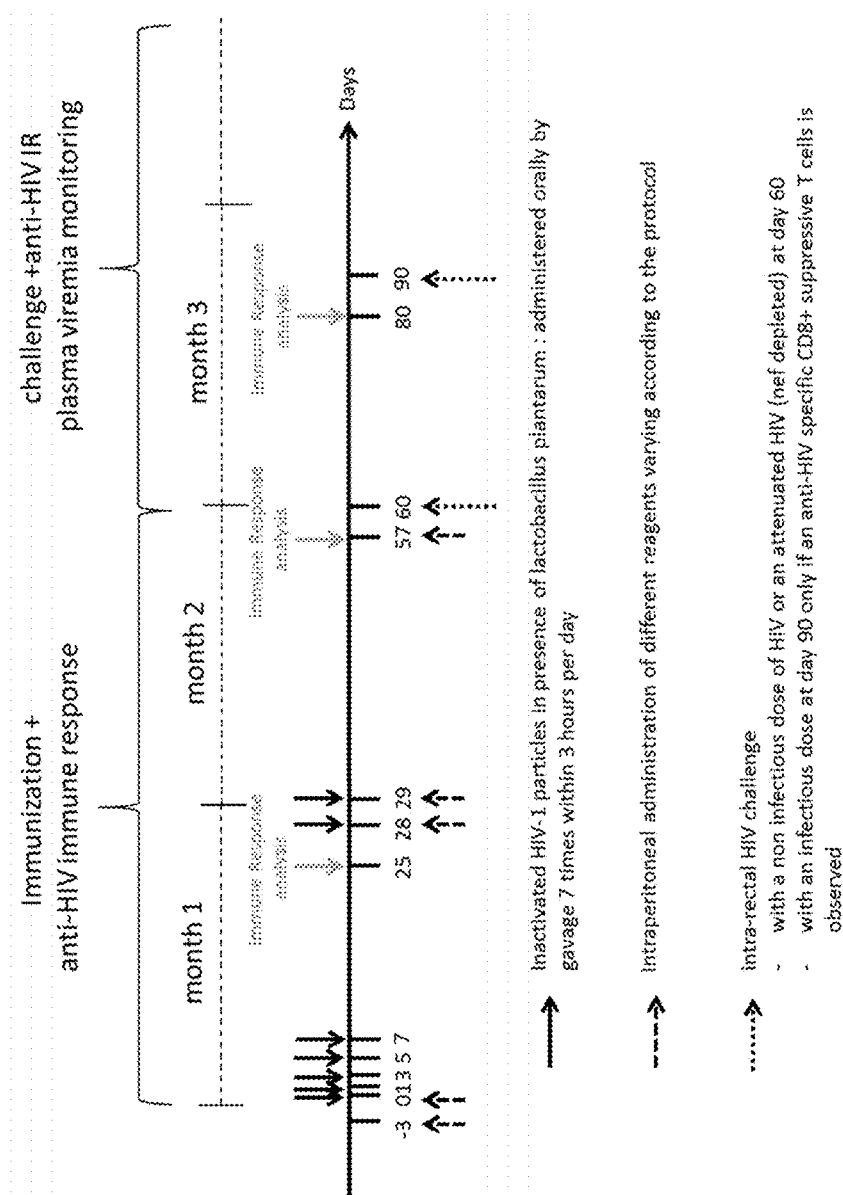
FIG. 9. Schematic representation of the oral immunization protocol in BLT mice with inactivated HIV and living *Lactobacillus plantarum*.

The FIG. 9 is a schematic representation of the oral immunization protocol in BLT mice.

BLT mice are valuable humanized models for the study of HIV infection. Indeed, BLT mice recapitulate important aspects of human immunity, including T cell immunity (Marshall E. Karpel et al., Curr Opin Virol. 2015 August; 13: 75-80).

Oral Immunization Protocol

The CD8 vaccine composition is in a form adapted to intragastrically administration and comprises: $4 \times 10^7$ copies/mL of an inactivated HIV-1 and $3 \times 10^9$ cfu/mL of living *Lactobacillus plantarum* in maltodextrin (20%) solution. BLT mice receive 0.2 mL of said CD8 vaccine composition and then 0.2 mL of the same composition every 30 min for 3 hours, at days 0, 1, 3, 5, 7 and 28, 29.

At day −3 and before each series of immunizations at days 0, 28 and 29, BLT mice receive (i.p.) injections of a combination of different reagents according to the protocol as described hereinafter:

Protocol 1: nothing
Protocol 2: poly I:C (100 µg/kg) and interferon lambda 1 (50-100 µg)
Protocol 3: polyclonal anti-IFN-α antibodies (PBL, 100 µg/kg) and poly I:C (100 µg/kg)
Protocol 4: polyclonal anti-IFN-α antibodies (PBL, 100 µg/kg), poly I:C (100 µg/kg) and interferon lambda 1 (50-100 µg)

At day 57, BLT mice receive injection of polyclonal anti-IFN-α antibodies (PBL, 100 µg/kg), poly I:C (100 µg/kg) and/or interferon lambda 1 (50-100 µg).

Bosting Immunization (Pre-Challenge)

At day 60, BLT mice receive intra-rectal injection of non-infectious dose of HIV-1 or an attenuated HIV-1 (e.g., HIV-1 depleted in protein nef).

Immune Response Analysis

Anti-HIV immune response is analyzed at day 25, 57 and 80. The analysis of the anti-SIV immune response comprises the monitoring of:

Plasma HIV IgM/IgG/IgA antibody titers, and/or
HIV Gag specific CD8$^+$ T cell and CD8$^+$ T cell-mediated anti-viral activity.

Challenge

At day 90, BLT mice receive intra-rectal injection of an infectious dose of HIV-1 only if an anti-HIV-1 specific CD8$^+$ suppressive T cells (as described in the present invention) is observed.

After challenge, anti-HIV-1 immune responses and plasma viremia are monitored every two weeks.

Example 6: Ex Vivo Generation and Expansion of Antigen (Ag) Specific CD8+ HLA-E Restricted T Cells Using HLA-E*01033-Transfected Derivative of K562 Cell Line Materials and Methods Human Blood Sample Blood samples from healthy individuals originated from Etablissement Francais du Sang (EFS, Paris). Blood cells were collected using standard procedures.

Cell Purification and Culture

Peripheral blood mononuclear cells (PBMCs) were isolated by density gradient centrifugation on Ficoll-Hypaque (Pharmacia). PBMCs were used either as fresh cells or stored frozen in liquid nitrogen. Naïve CD8+ T cells were isolated from PBMCs by negative selection using a MACS system. T cell subsets were cultured either in IMDM supplemented with 5% SVF, 100 IU/ml penicillin/streptomycin, 1 mM sodium pyruvate, 1 mM nonessential amino acids, glutamax and 10 mM HEPES (IMDM-5 media) in hypoxia 2%.

HLA-E*01033-transfected derivative of K562 (K562/HLA-E) cell line were maintained in RPMI 1640 medium (Lonza, Basel, Switzerland) supplemented with 10% fetal bovine serum, 2 mM L-glutamine, 25 mM HEPES and antibiotics in presence of 0.4 mg/ml G-418 (Calbiochem, San Diego, Calif.). When used as antigen-presenting cells, pulsed K562/HLA-E cell line was irradiated at 80000 rad.

Peptide-HLA Molecule Binding Assays

Peptide binding was assessed by HLA-E stabilization assays using HLA-E*01033-transfected derivative of K562 (K562/HLA-E) cell lines. Briefly, cells were re-suspended in serum-free medium at $1 \times 10^6$ cells/ml. Where appropriate, a peptide (see Table 1) was added. After overnight incubation at 26° C., cells were washed with PBS to remove free peptides. Next, HLA surface expression was monitored after staining with anti-HLA-E mAb. Analysis was done on a FACScalibur cytometer (BD Biosciences). Results are presented as the MFI of cells stained with anti-HLA-E mAb.

Generation and Expansion of Peptide-Specific HLA-E Restricted CD8+ T Cell Lines

Naïve CD8+ T were cultured in the presence of irradiated K562/HLA-E cell line as antigen-presenting cells (at 0.5× 10⁶/ml) pulsed with the appropriate peptide (10 µM) in complete medium supplemented with IL-21 (30 ng/ml). After 3 days, half of medium was exchanged and 30 ng/ml IL-21, 20 ng/mL interleukin 15 (IL-15) and 500 ng/mL soluble, Fc-fused IL15-Receptor alpha (sIL15Ra-Fc, R&D Systems) were added. Restimulation was done after 10 days with irradiated K562/HLA-E cells pulsed with the corresponding peptide in presence of IL-21, IL-15 and Fc-fused IL15-Receptor alpha. IL-2 (50 IU/ml) and IL-7 (10 ng/ml) were added 1 day after the second stimulation to further facilitate expansion of activated Ag-specific T cells. Then, cultures were stimulated weekly for 4-10 weeks. Peptide-specific expansion of T cells was monitored by flow cytometric analysis using a cytotoxic assay.

Cytotoxicity Assay

A cell-based Flow Cytometry assay was used to measured specific cytotoxic activity of the peptide-specific HLA-E restricted CD8+ T cell lines ex vivo generated. Briefly, CFSE labelled targets were incubated overnight at 26° C. (K562/HLA-E) in presence or absence of synthetic peptides and co-cultured with the CD8+ T cell lines for 5 hours at different ratios (10:1 and 1:1). Control tubes (target cells without CD8+ T cell lines) were also assayed to determine the spontaneous cell death. After 5 hours of co-culture, cells were stained with 7-AAD. For data analysis, the CFSE-positive target cells were examined for cell death by uptake of 7-AAD. CFSE and 7-AAD double positive cells were considered to be dead target cells. The percentage of specific cytotoxic activity was subsequently calculated using the following equation:

Cytotoxicity (%)=Target cell death−Spontaneous death×100−Spontaneous death×100

Results

HLA-E Expression on K562 Cell Line after Peptide Loading

Untransfected K562 cells do not display surface expression of HLA-E as assessed by flow cytometry as well as HLA-E transfected K562 in the absence of peptide loading (see Table 1). After pulsing K562/HLA-E overnight at 26° C. with specific HLA-E peptide from different origin, HLA-E surface expression was induced (see Table 1).

TABLE 1

Peptide-HLA molecule binding assay

| Cells | Peptides | MFI |
|---|---|---|
| Untransfected K562 | Without peptide | 1250 |
| HLA-E Transfected K562 | Without peptide | 1400 |
| HLA-E Transfected K562 | HCMV derived peptide VMAPRTLIL (SEQ ID NO: 5) | 6250 |
| HLA-E Transfected K562 | EBV derived peptide SQAPLPCVL (SEQ ID NO: 14) | 5860 |

TABLE 1-continued

Peptide-HLA molecule binding assay

| Cells | Peptides | MFI |
|---|---|---|
| HLA-E Transfected K562 | MBt derived peptide VMATRRNVL (SEQ ID NO: 15) | 7523 |
| HLA-E Transfected K562 | HIV-1 Pol derived peptide PEIVIYDYM (SEQ ID NO: 16) | 7320 |
| HLA-E Transfected K562 | HIV-1 Pol derived peptide RIRTWKSLV (SEQ ID NO: 17) | 6580 |
| HLA-E Transfected K562 | HIV-1 Gag derived peptide RMYSPVSIL (SEQ ID NO: 1) | 8240 |
| HLA-E Transfected K562 | HIV-1 Gag derived peptide TALSEGATP (SEQ ID NO: 3) | 8530 |

Detection of Antigen Specific HLA-E Restricted CD8+ T Cells Using Cytotoxicity Assay Seeing cell proliferation in the long-term stimulated cultures, the inventors wanted to estimate their specific functional activity using cytotoxicity assay. K562/HLA-E peptide pulsed cells induced the activation and the expansion of antigen-specific CD8+ T cell lines, since cells that have proliferated exhibit a high cytotoxic response against the candidate antigens, while no significant activity against an irrelevant antigen (see Table 2).

TABLE 2 specific cytotoxic activity of the expanded CD8+ T cells

| Peptide specific HLA-E restricted | % cytotoxicity against the relevant peptide | | % cytotoxicity against an irrelevant peptide | |
|---|---|---|---|---|
| CD8+ T cell lines | Ratio 10:1 | Ratio 1:1 | Ratio 10:1 | Ratio 1:1 |
| HCMV derived peptide VMAPRTLIL | 75 | 32 | 12 | 8 |
| EBV derived peptide SQAPLPCVL | 82 | 35 | 15 | 10 |
| MBt derived peptide VMATRRNVL | 67 | 28 | 9 | 5 |
| HIV-1 Pol derived peptide PEIVIYDYM | 87 | 35 | 17 | 8 |
| HIV-1 Pol derived peptide RIRTWKSLV | 73 | 28 | 16 | 10 |
| HIV-1 Gag derived peptide RMYSPVSIL | 82 | 33 | 15 | 9 |
| HIV-1 Gag derived peptide TALSEGATP | 86 | 32 | 17 | 10 |

Example 7: Critical Pathogenic Role of IFN-α in Human HIV-1 Infection

Material and Methods

Cryopreserved PBMCs were thawed in RPMI 1640 with 10% fetal bovine serum (FBS) and washed in FACS buffer. Phenotypic staining was performed on $10^6$ cells by incubation with a viability marker (AmCyan live-dead kit from Invitrogen) and with antibodies conjugated to CD3, CD4, CD8, CD45RA, CCR7. Subsequently, cells were washed, fixed with 4% paraformaldehyde for 5 min, washed, and acquired with an AURORA cytometer (Cytek).

Frozen serums were thawed at 4° C. and centrifuged at 4000 G for 10 min at 4° C. IFN-α serum concentrations were measured using the high sensitivity Simoa® technology (Digital ELISA technology) (Quanterix).

Results

Comparison of Central Memory (CM) CD8+ T Cell Distributions in HIV-1-Infected Subjects In study of chronically HIV-1-infected subjects, the following groups were studied:
(i) elite controllers (EC) who naturally suppress HIV-1 in the absence of combined antiretroviral therapy treatment (c-ART)
(ii) non-controllers before (pre-cART) and after cART (post-cART) treatment, and
(iii) a cohort of age-matched healthy donor (HD) subjects.

The relative frequencies of the CM populations within the CD8+ T cell compartments were evaluated in each of the subject groups.

The gating strategy to define this subset is the following. Briefly, singlet cells were defined, followed by gating on lymphocytes and live cells. Among the live cells, CD3+T lymphocytes were identified, followed by the definition of CD8+ subpopulations. Subsequently, the expression of CD45RA and CCR7 was analyzed in the CD8+T lymphocytes. Central memory T cells (TCM) are CD45RA−CCR7+.

Figure 10A:
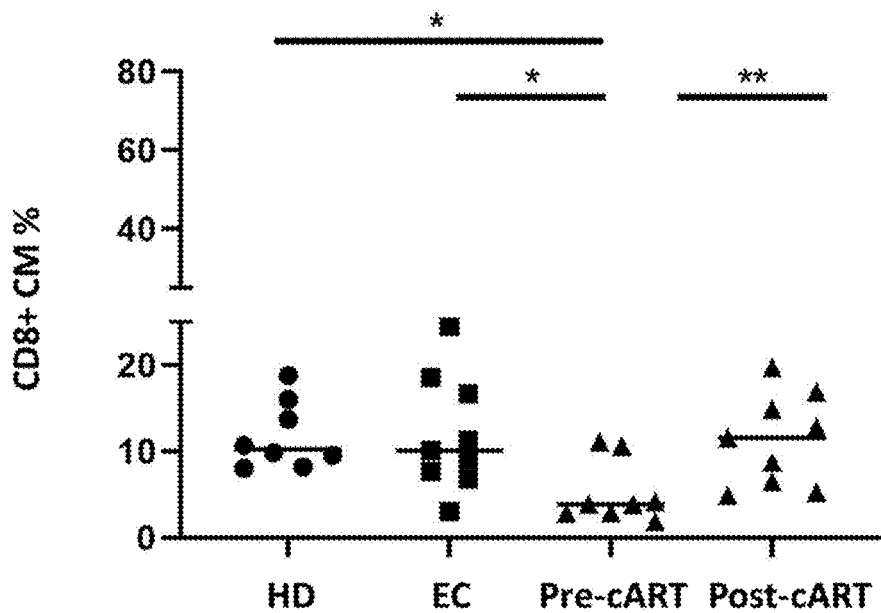
FIG. 10A. Comparison of CM CD8+ T cell distributions and serum IFN-α levels in HIV-1-infected subjects and critical pathogenic role of IFN-α in human HIV-1 infection. Comparison of CM CD8+ T cell distributions in HIV-1-infected subjects.

FIG. 10A shows that the level of CM CD8+ cells was significantly lower in non-controllers before cART than in other groups. Moreover, combined antiretroviral therapy (cART) results in increase of CM CD8+ cells.

Comparison of Serum IFN-α Levels in HIV-1-Infected Subjects

Figure 10B:
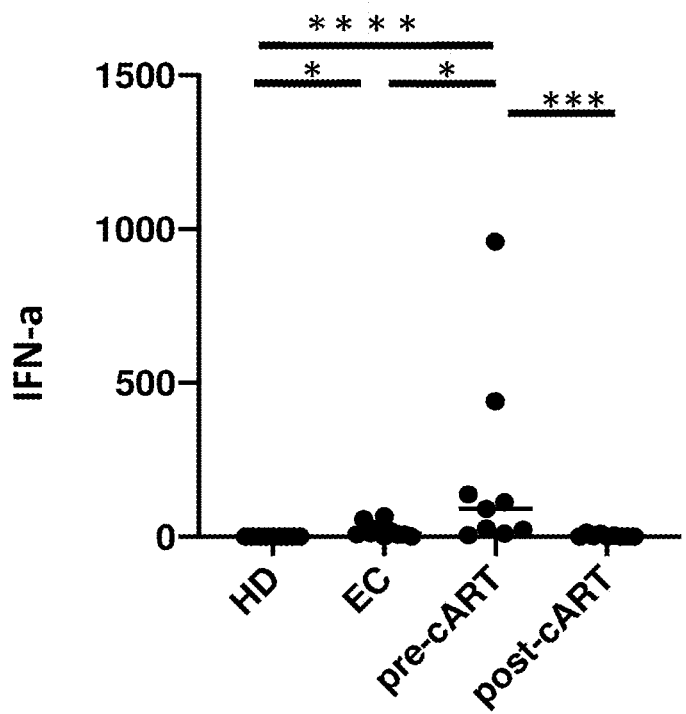
FIG. 10B. Comparison of CM CD8+ T cell distributions and serum IFN-α levels in HIV-1-infected subjects and critical pathogenic role of IFN-α in human HIV-1 infection. Comparison of serum IFN-α levels in HIV-1-infected subjects.

Serum levels of IFN-α was measured in the 4 groups. FIG. 10B shows that the non-controller patients have significantly increased serum IFN-α levels before treatment compared with after treatment.

Figure 10C:
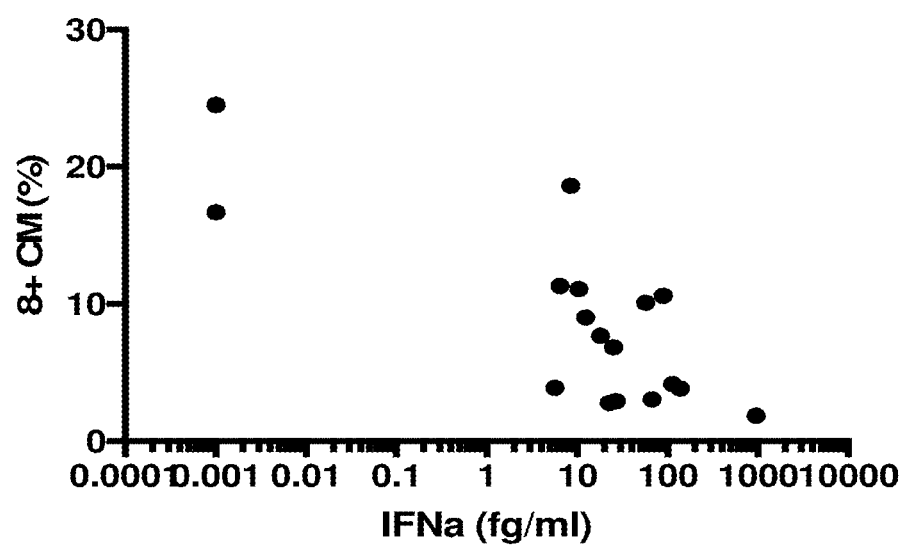
FIG. 10C. Comparison of CM CD8+ T cell distributions and serum IFN-α levels in HIV-1-infected subjects and critical pathogenic role of IFN-α in human HIV-1 infection. Relationship between CD8+CM frequency and serum IFN-α level in non-treated HIV patients (EC and pre-cART group).

IFN-α Inversely Correlates with the Percentage of CM CD8+ Cells in HIV-Infected Patients without Treatment In the population of HIV infected patients (EC pre-cART patients), the inventors explored the potential correlations between the level of CM CD8+ cells and the serum IFN-α levels. In this study, there was a significant negative correlation between the frequency of CM CD8+ cells and serum IFN-α levels (spearman correlation r=−0.667; p<0.005). This reflects the critical pathogenic effect of IFN-α on T cell proliferation in secondary organs (see FIG. 10C).

Example 8: Prophylactic Vaccine to SIV in Macaques with Inactivated SIV and Living *Lactobacillus plantarum*

Figure 11:
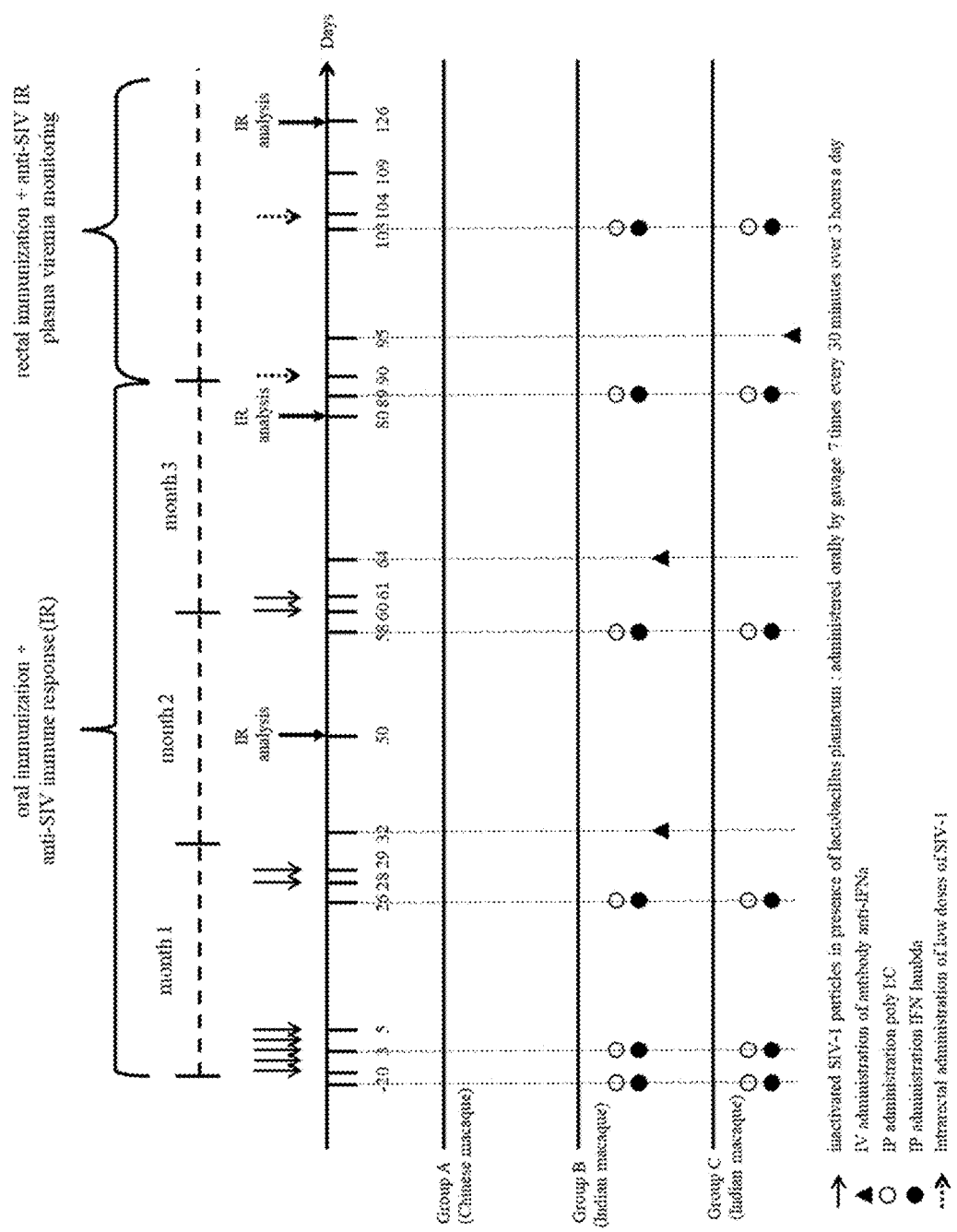
FIG. 11. Schematic representation of the oral immunization protocol in macaques with inactivated SIV and living *Lactobacillus plantarum*.

This protocol comprises two steps described below.
FIG. 11 is a schematic representation of the protocol scheme of step 1.

Step 1: Identification of the Most Efficient Regimen for Induction of Virus Specific CD8+ Suppressive T Cells in Rhesus Macaques (RM)

Immunization protocol is based on the experimental work performed on Chinese rhesus macaques and described in Lu et al. (2012) Cell Rep. 2(6), 1736-46. This protocol is comprised of three steps:
1) oral priming with preparation containing inactivated SIVmac239, as activate principle, and living *Lactobacillus plantarum* (LP), as adjuvant,
2) oral boosting with the same preparation and
3) intrarectal boosting with non-infectious doses of living virus.

Eight male RM, 2 RM of Chinese origin and 6 of Indian origin are included.

Oral priming immunization is carried out on 5 consecutive days. Each day, monkeys are intragastrically administered 30 ml of a preparation containing $4 \times 10^7$ copies/ml of inactivated SIV and $3 \times 10^9$ cfu/ml of living LP in maltodextrin (20%) solution. Then they receive 25 ml of the same preparation intragastrically every 30 min for 3 hours.

Oral boosting immunization is administered at day 28 and day 29 and if necessary at day 60 and day 61.

Intrarectal boost is performed twice by a 2-week interval from day 90. Monkeys of Indian origin additionally receive an intraperitoneal (IP) injection of poly I:C and lambda IFN at day −2, day 3 during the oral priming and two days before each oral boosting, i.e. at day 26 and if necessary at day 58 and one day before IR boosts.

The 6 RM of Indian origin are distributed in two groups (B and C) depending on when the anti-IFNα antibody is added during the immunization. For group B anti-IFNα antibody is administered at day 32, and if necessary at day 64, one day before each IR boosts. For group C, anti-IFNα antibody is administered only five days after the first IR boost. For all macaques, induction of virus specific CD8+ suppressive T cells is monitored at day 50 and if necessary at day 80 and at day 126. Plasma viral loads are followed weekly after the IR boosts.

Step 2: Evaluation of the Vaccine Efficacy by Rectal Challenge with SIVmac239.

Only monkeys who mount virus-specific CD8+ suppressive T cells are challenged intrarectally with high infectious dose of SIVmac239 (100,000 TCID50). Plasma viral loads are followed every week for 6 weeks.

Example 9: Prophylactic Vaccine to HIV in BSLT Mice

Figure 12:
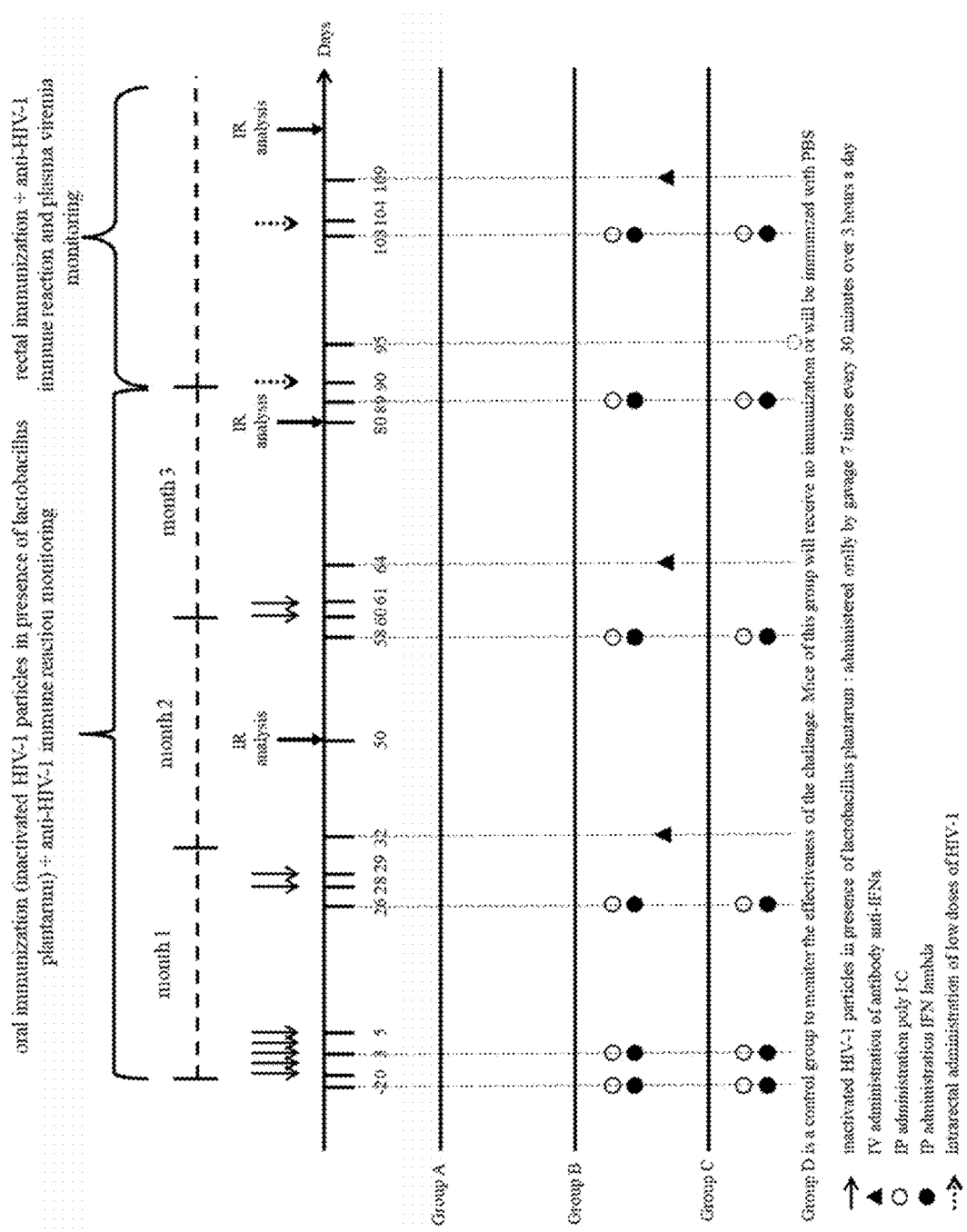
FIG. 12. Schematic representation of the oral immunization protocol in BSLT mice with inactivated HIV and living *Lactobacillus plantarum*.

This protocol comprises two steps described below.
FIG. 12 is a schematic representation of the protocol scheme of step 1.

Step 1: Identification of the Most Efficient Regimen for Induction of Anti-HIV-1 Specific CD8+ Suppressive T Cells in BSLT Mice Immunization protocol is based on the experimental work performed on Chinese rhesus macaques and described in Lu et al. (2012) Cell Rep. 2(6), 1736-46. This protocol is comprised of three steps:
1) oral priming via intragastric route with preparation containing inactivated HIV-1, as activate principle, and living *Lactobacillus plantarum* (LP), as adjuvant;
2) oral boosting via intragastric route with the same preparation;
3) intrarectal boosting with low doses of living virus.

Four groups of 10 mice (A, B, C and D) are included. Group D is a control group to monitor the effectiveness of the challenge. Mice of this group D receive no immunization or is immunized with PBS.

Oral priming immunization via intragastric route consists of daily oral intake of inactivated HIV-1 and living LP in maltodextrin (20%) solution over a period of 5 days. Each day, mice receive the same preparation intragastrically, 3 times every 30 minutes over 1 hour. Mice receive 200 mc1 of the preparation.

Oral boosting immunization via intragastric route is administered at day 28 and day 29 and, if necessary, at day 60 and day 61.

Intrarectal boost is performed twice by a 2-week interval at day 90 and day 104. Group B and C additionally receive an intraperitoneal injection of poly I:C and lambda IFN (100-500 mc1) at day −2, day 3 during the oral priming via intragastric route and two days before each oral boosting via intragastric route, i.e. at day 26 and, if necessary, at day 58 and one day before the IR boosts (day 89 and day 103).

Group B and C differ depending on when the anti-IFNα antibody is added during the immunization. For group B anti-IFNα antibody is administered at day 32 during the oral boost via intragastric route and, if necessary, at day 64 during the oral boost via intragastric route. For group C anti-IFNα antibody is administered only five days after the IR boosts. For all mice, induction of virus-specific CD8+ suppressive T cells is monitored at day 50 and, if necessary, at day 80 and at day 126. Plasma viral loads are followed weekly after the IR boosts.

Step 2: Evaluation of the Vaccine Effectiveness by Rectal Challenge with HIV-1

Two months after the last antibody anti-IFNα administration, only mice which mount virus-specific CD8+ suppressive T cells are challenged intrarectally with high infectious dose of HIV-1 (100,000 TCID50). Plasma viral loads are followed every week for 6 weeks.

The invention claimed is:

1. A method for prophylactically treating acquired immune deficiency syndrome (AIDS) in a subject in need thereof, comprising administering to the subject:
   1) a CD8 therapeutic vaccine specific for at least one human immunodeficiency virus (HIV) antigen,
   2) optionally interferon-alpha blocking agent, and
   3) a type III interferon and/or an agent stimulating the production of type III interferon, wherein the type III interferon comprises at least one IFN-λ selected from the group consisting of IFN-λ1, IFN-λ2 IFN-λ3 and IFN-λ4, and wherein the agent stimulating the production of type III interferon comprises at least one TLR ligand, RIG-I ligand, and/or MDA5 ligand.

2. The method for prophylactically treating according to claim 1, wherein the interferon-alpha blocking agent is selected from the group of: an agent neutralizing circulating alpha interferon, an agent blocking interferon-alpha signaling, an agent depleting IFN-a producing cells, and/or an agent blocking IFN-a production, wherein the agent neutralizing circulating alpha interferon is selected from the group comprising active anti-IFN-a vaccine including antiferon or passive anti-IFN-a vaccine including anti-IFN-a antibodies or anti-IFN-a hyper-immune serum, wherein the blocking agent of interferon-alpha signaling is selected from the group of anti-type I interferon R1 or R2 antibodies or from interferon-alpha endogenous regulators including SOSC1 or aryl hydrocarbon receptors, wherein the agent depleting IFN-a producing cells is an agent depleting plasmacytoid dendritic cells (pDCs), and wherein the agent blocking IFN-a production is an agent blocking the production of IFN-a by pDCs.

3. The method for prophylactically treating according to claim 1, wherein the CD8 therapeutic vaccine elicits or comprises suppressor MHC-1b/E-restricted CD8+ T cells.

4. The method for prophylactically treating according to claim 1, wherein the CD8 therapeutic vaccine elicits or comprises suppressor MHC-1b/E-restricted CD8+ T cells, and wherein the suppressor MHC-1b/E-restricted CD8+ T cells are generated by ex vivo or in vivo induction of HLA-1a-deprived dendritic cells.

5. The method for prophylactically treating according to claim 1, wherein the CD8 therapeutic vaccine elicits or comprises suppressor MHC-1b/E-restricted CD8+ T cells, wherein the suppressor MHC-1b/E-restricted CD8+ T cells are generated by ex vivo or in vivo induction of HLA-1a-deprived dendritic cells, and wherein the HLA-1a-deprived dendritic cells are obtained by an agent inhibiting TAP expression or activity.

6. The method for prophylactically treating according to claim 1, wherein the CD8 therapeutic vaccine is an active vaccine, wherein the CD8 therapeutic vaccine is a live viral vector comprising at least one HIV antigen, and wherein the live viral vector is selected from the group of cytomegalovirus, lentivirus, vaccinia virus, adenovirus or plasmid.

7. The method for prophylactically treating according to claim 1, wherein the CD8 therapeutic vaccine is an active vaccine, and wherein the CD8 therapeutic vaccine is a cytomegalovirus (CMV) vector comprising:
   a first nucleic acid sequence encoding at least one HIV antigen,
   optionally a second nucleic acid sequence comprising a first microRNA recognition element (MRE) operably linked to a CMV gene that is essential or augmenting for CMV growth, wherein the MRE silences expression in the presence of a microRNA that is expressed by a cell of endothelial lineage;
and wherein the CMV vector does not express an active UL128 protein or ortholog thereof; does not express an active UL130 protein or ortholog thereof; does not express an active UL146 or ortholog thereof; does not express an active UL147 protein or ortholog thereof, and wherein the CMV vector expresses at least one active UL40 protein or an ortholog thereof; expresses at least one active US27 protein or an ortholog thereof and/or expresses at least one active US28 protein or an ortholog thereof.

8. The method for prophylactically treating according to claim 1, wherein the CD8 therapeutic vaccine is a cytomegalovirus (CMV) vector, and wherein the CMV vector is a human CMV (hCMV).

9. The method for prophylactically treating according to claim 1, wherein the CD8 therapeutic vaccine is an active vaccine, and wherein the CD8 therapeutic vaccine comprises at least one HIV antigen and a non-pathogenic bacterium.

10. The method for prophylactically treating according to claim 1, wherein the CD8 therapeutic vaccine comprises at least one HIV antigen and a non-pathogenic bacterium, wherein the HIV antigen is selected from the group of virus, virus particles, virus-like particles, recombinant virus, recombinant virus particles, conjugate viral proteins and concatemer viral proteins, and wherein said virus, virus particles or said recombinant virus particles are attenuated or inactivated.

11. The method for prophylactically treating according to claim 1, wherein the CD8 therapeutic vaccine comprises at least one HIV antigen and a non-pathogenic bacterium, wherein the non-pathogenic bacterium is living, and wherein said non-pathogenic bacterium is selected from attenuated or inactivated pathogenic bacteria.

12. The method for prophylactically treating according to claim 1, wherein the CD8 therapeutic vaccine comprises at least one HIV antigen and a non-pathogenic bacterium, and wherein the non-pathogenic bacterium is a *Lactobacillus* bacterium.

13. The method for prophylactically treating according to claim 1, wherein the CD8 therapeutic vaccine comprises at least one HIV antigen and a non-pathogenic bacterium, and wherein the non-pathogenic bacterium is *Lactobacillus plantarum*.

14. The method for prophylactically treating according claim 1, wherein the CD8 therapeutic vaccine is an active vaccine, and wherein the CD8 therapeutic vaccine is an ex vivo generated dendritic, natural killer or B cell population presenting MHC-1b/E-restricted and MHC-II restricted antigens, and wherein the MHC-lb/E-restricted antigen is an HIV antigen.

15. The method for prophylactically treating according to claim 1, wherein the CD8 therapeutic vaccine is a passive vaccine, and wherein the CD8 therapeutic vaccine is an ex vivo generated autologous MHC-1b/E-restricted CD8$^+$ T cell population, and wherein the MHC-1b/E-restricted CD8$^+$ T cell population recognizes an MHC-1b/E-restricted HIV antigen.

16. The method for prophylactically treating according to claim 1, wherein the HIV antigen is derived from any HIV strain, and wherein the HIV antigen is selected from the group consisting of HIV gag, HIV env, HIV rev, HIV tat, HIV nef, HIV pol, and HIV vif antigens.

17. The method for prophylactically treating according claim 1, wherein the HIV antigen is an HIV-derived HLA-E-binding antigen.

18. The method for prophylactically treating according to claim 1, wherein the HIV antigen is a HIV-derived HLA-E-binding antigen, and wherein the HIV-derived HLA-E-binding antigen is selected from the antigens of SEQ ID NO: 1 to SEQ ID NO: 4.

\* \* \* \* \*